United States Patent [19]

Cabib et al.

[11] Patent Number: 5,784,162

[45] Date of Patent: *Jul. 21, 1998

[54] SPECTRAL BIO-IMAGING METHODS FOR BIOLOGICAL RESEARCH, MEDICAL DIAGNOSTICS AND THERAPY

[75] Inventors: Dario Cabib, Timrat; Robert A. Buckwald, Ramat Yishai; Zvi Malik, Kfar Haroe; Yuval Garini, Mizpe Koianit; Nir Katzir, Givat Elah, all of Israel; Dirk G. Soeknsen, Carlsbad, Calif.

[73] Assignee: Applied Spectral Imaging Ltd., Migdal Haemek, Israel

[*] Notice: The term of this patent shall not extend beyond the expiration date of Pat. No. 5,539,517.

[21] Appl. No.: 571,047

[22] Filed: Dec. 12, 1995

Related U.S. Application Data

[63] Continuation-in-part of Ser. No. 392,019, Feb. 21, 1995, Pat. No. 5,539,517, which is a continuation of Ser. No. 107,673, Aug. 18, 1993, abandoned.

[51] Int. Cl.$^6$ .................................................. G01B 9/02
[52] U.S. Cl. ........................... 356/346; 250/461.2; 435/6
[58] Field of Search .................................... 356/346, 300, 356/326; 250/339.02, 458.1, 459.1, 461.1, 461.2; 128/665; 382/128, 129, 133; 435/6

[56] References Cited

U.S. PATENT DOCUMENTS

| | | | |
|---|---|---|---|
| 5,377,003 | 12/1994 | Lewis et al. | 356/300 |
| 5,539,517 | 7/1996 | Cabib et al. | 356/346 |

*Primary Examiner*—Samuel A. Turner
*Attorney, Agent, or Firm*—Mark M. Friedman

[57] ABSTRACT

According to the present invention there are provided spectral imaging methods for biological research, medical diagnostics and therapy comprising the steps of (a) preparing a sample to be spectrally imaged; (b) viewing the sample through an optical device, the optical device being optically connected to an imaging spectrometer, the optical device and the imaging spectrometer obtaining a spectrum of each pixel of the sample by: (i) collecting incident light simultaneously from all pixels of the sample using collimating optics; (ii) passing the incident collimated light through an interferometer system having a number of elements, to form an exiting light beam; (iii) passing the exiting light beam through a focusing optical system which focuses the exiting light beam on a detector having a two-dimensional array of detector elements, so that at each instant each of the detector elements is the image of one pixel of the sample, so that the real image of the sample is stationary on the plane of the detector array, and so that each of the detector elements produces a signal which is a particular linear combination of light intensity emitted by the pixel at different wavelengths, wherein the linear combination is a function of the instantaneous optical path difference; (iv) rotating one or more of the elements of the interferometer system, so that the optical path difference between the two coherent beams generated by the interferometer system is scanned simultaneously for all the pixels of the sample; and (v) recording signals of each of the detector elements as function of time using a recording device to form a first spectral cube of data; and (c) interpreting the first spectral cube of data using a mathematical algorithm.

69 Claims, 22 Drawing Sheets

FIG. 4
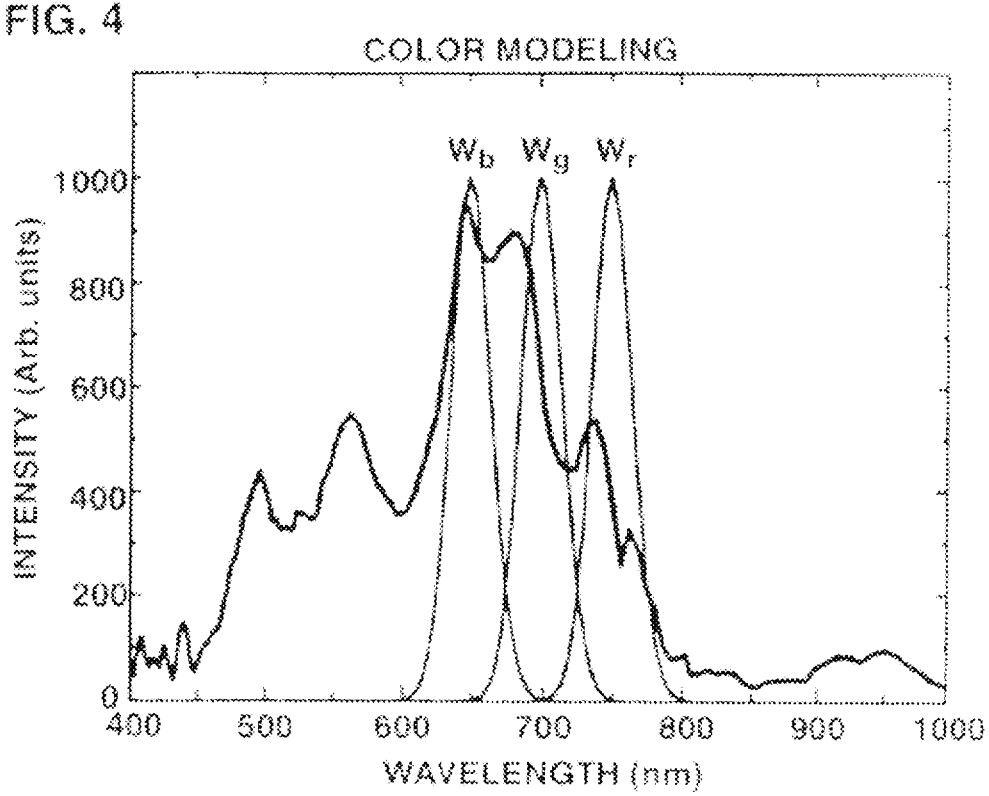
(a)
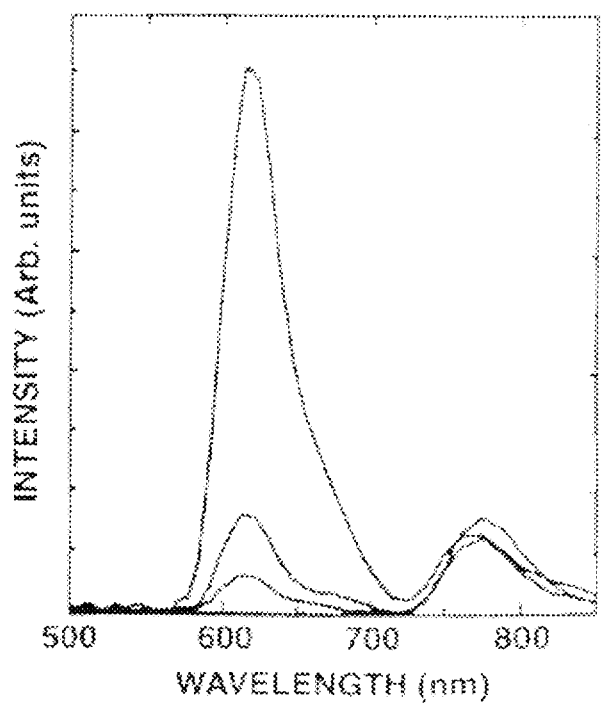
(b)
FIG. 5

(a)

(b)

(c)

(d)

(a)

(b)

(a)

(b)

NM (a)    (b)

(a)

(b)

(c)

(a)

(b)

FIG. 30b    p10
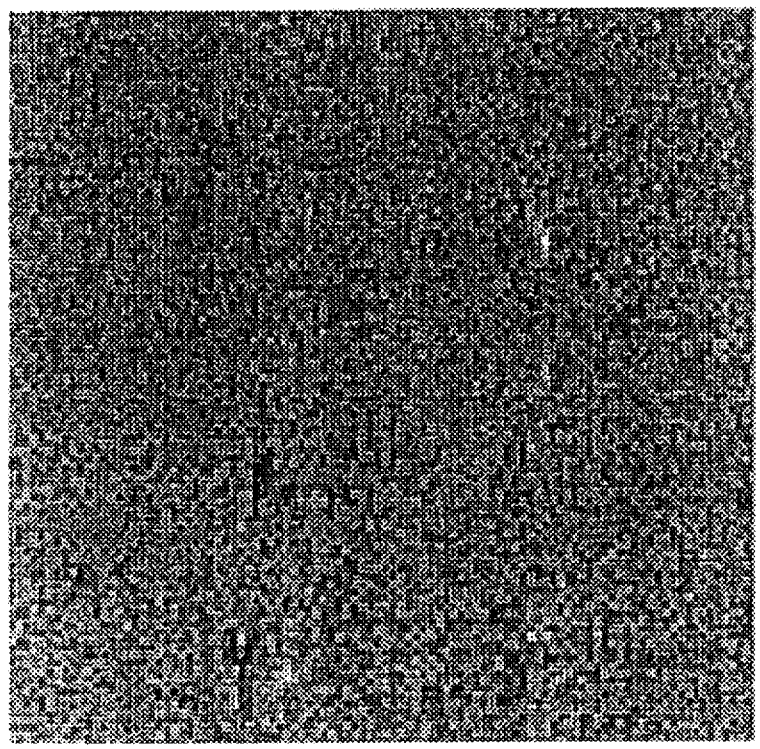
FIG. 30c    p13
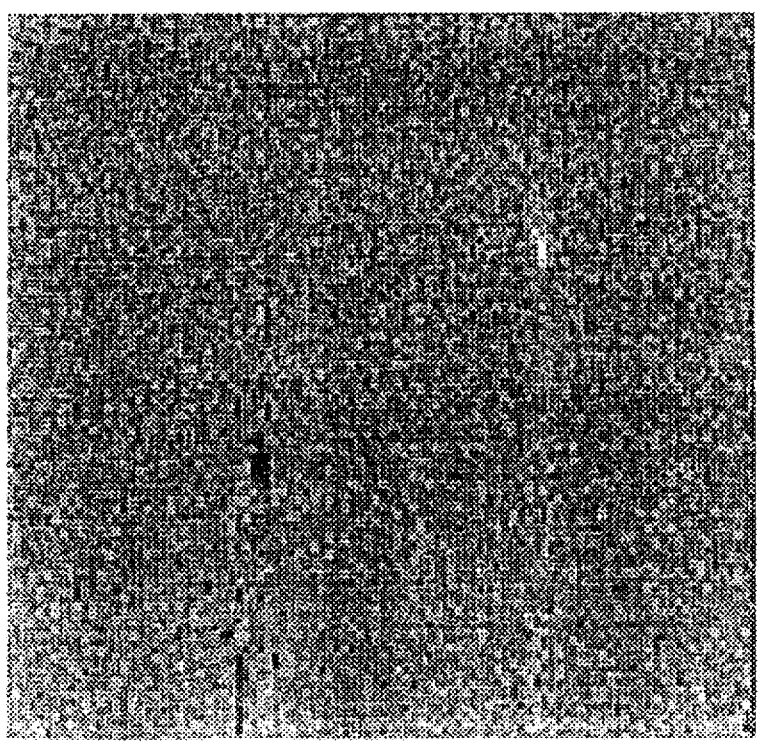

SPECTRAL BIO-IMAGING METHODS FOR BIOLOGICAL RESEARCH, MEDICAL DIAGNOSTICS AND THERAPY

This is a continuation in part of U.S. patent application Ser. No. 08/392,019, filed Feb. 21st, 1995, now U.S. Pat. No. 5,539,517, which is a continuation of U.S. patent application Ser. No. 08/107,673, filed Aug. 18th, 1992, now abandoned.

FIELD AND BACKGROUND OF THE INVENTION

The present invention relates to spectral methods in general and, more particularly, to spectral imaging methods for biological research, medical diagnostics and therapy, which methods are referred to hereinbelow as spectral bio-imaging methods. The methods of the present invention can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions.

A spectrometer is an apparatus designed to accept light, to separate (disperse) it into its component wavelengths, and measure the lights spectrum, that is the intensity of the light as a function of its wavelength. An imaging spectrometer is one which collects incident light from a scene and measures the spectra of each pixel (i.e., picture element) thereof.

Spectroscopy is a well known analytical tool which has been used for decades in science and industry to characterize materials and processes based on the spectral signatures of chemical constituents. The physical basis of spectroscopy is the interaction of light with matter. Traditionally, spectroscopy is the measurement of the light intensity emitted, transmitted, scattered or reflected from a sample, as a function of wavelength, at high spectral resolution, but without any spatial information.

Spectral imaging, on the other hand, which is a combination of high resolution spectroscopy and high resolution imaging (i.e., spatial information) has yet not been used for analyzing biological samples. The closest work so far described concerns either obtaining high spatial resolution information from a biological sample yet providing only limited spectral information, for example, when high spatial resolution imaging is performed with one or several discrete band-pass filters [See, Andersson-Engels et al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

As will be described in great details below, combining spectroscopy with imaging is useful for various biological research and medical applications. One example concerns detection of specific cellular constituents (e.g., proteins, nucleic acid sequences) after being labeled (i.e., tagged) with fluorescent probes. In this direction spectral imaging can be used to identify and map several fluorophores, simultaneously, in one measurement. In fact, the inherently high spectral resolution of spectral imaging is ideally suited for 'sorting out' fluorescent probes (or other chemical constituents) with overlapping spectra. Similarly, spectral imaging enables the detection, at any location in the image, of subtle spectral shifts due to environmental nonuniformities of the sample (e.g., pH and the like).

Conceptually, a spectral bio-imaging system consists of (1) a measurement system, and (2) an analysis software. The measurement system includes all of the optics, electronics and the manner in which the sample is illuminated (e.g., light source selection), the mode of measurement (e.g., fluorescence or transmission), as well as the calibration best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features. However, the high cost, size and configuration of remote sensing spectral imaging systems (e.g., Landsat, AVIRIS) has limited their use to air and satellite-born applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30].

There are three basic types of spectral dispersion methods that might be considered for a spectral bio-imaging system: (i) spectral grating, (ii) spectral filters and (iii) interferometric spectroscopy. As will be described below, the later is best suited to implement the methods of the present invention.

In a grating (i.e., monochromator) based systems, also known as slit-type imaging spectrometers, such as for example the DILOR system: [see, Valisa et al. (September 1995) presentation at the SPIE Conference European Medical Optics Week, BiOS Europe '95, Barcelona, Spain], only one axis of a CCD (charge coupled device) array detector (the spatial axis) provides real imagery data, while a second (spectral) axis is used for sampling the intensity of the light which is dispersed by the grating as function of wavelength. The system also has a slit in a first focal plane, limiting the field of view at any given time to a line of pixels. Therefore, a full image can only be obtained after scanning the grating or the incoming beam in a direction parallel to the spectral axis of the CCD in a method is known in the literature as line scanning. The inability to visualize the two-dimensional image before the whole measurement is completed makes it impossible to choose, prior to making a measurement, a desired region of interest from within the field of view and/or to optimize the system focus, exposure time, etc. Grating based spectral imagers are popular in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using AOTF or LCTF (see below). Similarly to the slit type imaging spectrometers equipped with a grating as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD.

Tunable filters, such as acousto-optic tunable filters (AOTFs) and liquid-crystal tunable filter (LCTFs) have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data. As stated above, no literature has been found by the inventors of the present invention describing high resolution spectroscopy combined with high resolution imaging applied to biomedicine, using an interferometric imaging spectrometer and analysis and display algorithms such as those proposed here. As further mentioned above, there have been papers and patents showing preliminary work in this direction either through low resolution and low sensitivity spectroscopy combined with high resolution imaging, or the opposite, high resolution spectroscopy on one or a few points of a sample. See, for example: (1) In cytogenetic research: Ried (January 1994) Fluoreszenz in situ Hybridizierung in der genetischen Diagnostik, Faculty of theoretical medicine, Ruprecht-Karls University Heidelberg. (2) In drug distribution in cells: Manfait and Charonov (1995) Fluorescence spectral imaging: State of the art and perspectives. Presented at "AFC CYTOMETRIE '95", Reims, France, Sep. 27th–29th, 1995. (3) In tissue cancer detection: U.S. Pat. No. 4,930,516 to Alfano et al.; Andersson-Engels (1990) Proceedings of SPIE, Bio-imaging and Two-Dimensional Spectroscopy, 1205, pp. 179–189; and, Pitris et al. (1995) Paper presented at European Biomedical Optics Week by SPIE, 12–16 Sep. 1995, Barcelona Spain. (4) In cancer characterization at the cell level: Wied et al. (1981) Computer Discrimination of Ectocervical Cells, The International Academy of Cytology Analytical and Quantitative Cytology, Vol 3, p. 225. (5) In ophthalmology: Delori (1995) Appl. Optics Vol. 27, 1113, 1988, and Appl Optics, Vol. 28, 1061, and other papers on slit camera, and fluorescein angiography, for example, Delori et al. (1980) Vision Research, Vol. 20, 1099.

However, these papers and patents differ from the present invention in view of the hardware employed; the combination of both high spatial and spectral resolution achieved; the algorithms used to analyze and display the results; and finally, the chemical physiologic and pathologic indications that it gives a diagnostician, researcher or surgeon on the cellular and/or tissue level.

A method and apparatus for spectral analysis of images which have advantages in the above respects was disclosed in U.S. patent application Ser. No. 08/392,019 to Cabib et al., filed Feb. 21st, 1995 which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed. Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measuring time and/or substantially increasing the signal-to-noise ratio (i.e., sensitivity). Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. patent application Ser. No. 08/392,019, the total time spent summed over all the detectors on a particular pixel is the same, $nT/m^2$. However, whereas in the conventional grating method the energy seen by every detector at any time is of the order of 1/n of the total, because the wavelength resolution is 1/n of the range, in a method according to the invention described in U.S. patent application Ser. No. 08/392,019 the energy is of the order of unity because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. patent application Ser. No. 08/392.019, all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fiber optics for industrial monitoring and medical imaging, diagnosis, therapy and others.

Spectral bio-imaging systems are potentially useful in all applications in which subtle spectral differences exist between chemical constituents whose spatial distribution and organization within an image are of interest. The measurement can be carried out using virtually any optical system attached to the system described in patent application Ser. No. 08/392.019, for example, an upright or inverted microscope, a fluorescence microscope, a macro lens, an endoscope and a fundus camera. Furthermore, any standard experimental method can be used, including light transmission (bright field and dark field), auto-fluorescence and fluorescence of administered probes, etc.

Fluorescence measurements can be made with any standard filter cube (consisting of a barrier filter, excitation filter and a dichroic mirror), or any customized filter cube for special applications, provided the emission spectra fall within the spectral range of the system sensitivity. Spectral bio-imaging can also be used in conjunction with any standard spatial filtering method such as dark field and phase contrast, and even with polarized light microscopy. The effects on spectral information when using such methods must, of course, be understood to correctly interpret the measured spectral images.

There are many experimental methods and specific applications for spectral bio-imaging systems in transmission and in fluorescence microscopy. These methods and applications include but are not limited to the following: (1) for transmission microscopy—measurements of stained histological samples; and (2) for fluorescence microscopy—(i) spectral identification of multiple fluorophores; (ii) detecting microenvironmental changes in subcellular compartments (e.g., pH, $Ca^{++}$ ion concentration) and dyes characterization; (iii) measurement of auto-fluorescence from natural pigments (e.g., chlorophyll); and, (iv) Fluorescence Resonance Energy Transfer (FRET). Other possible applications, include (1) time resolved spectral imaging (by utilizing a gated intensified CCD with an appropriate external trigger) and (2) Raman scattering measurements.

One of the major benefits of the Human Genome Project (HGP) has been the isolation of a large number of nucleic acid probes for diseased genes and other chromosomal regions and structures. This has stimulated interest in DNA diagnostics as the number and types of tests that can be developed is dependent upon these probes. In recent years there has been particular interest in fluorescent in situ hybridization (FISH) which is the process of marking with a fluorescent moiety conjugated to a specific nucleic acid probe complementary to an examined chromosomal region, followed by visualization of the fluorescent moiety by fluorescence microscopy.

There is a clear trend for employing FISH technology in the clinic in parallel to its traditional employment in the basic research laboratory. FISH may be considered an advanced approach to cytogenetics and it is clear that the amount of information about chromosomes that may be gained from FISH far outdistances that obtained from standard karyotyping by DNA banding methods. In addition, diagnostics information may be gained much more rapidly using techniques such as interphase cytogenetics as compared to classical (metaphase) cytogenetics.

According to the present invention provided is a FISH imaging method, capable of simultaneously acquire fluorescence spectra from all pixels of a field of view of a microscope and detect the location of many probes in a single experiment. In conjunction with the availability of chromosome specific probes and novel labeling strategies, the method is able to create a FISH karyotype with each chromosome being painted with a different color (i.e., 24 different colors for a human karyotype). This method results in extremely high sample throughput and allows analysis of an essentially unlimited number of probes.

Another objective of the present invention is to map in a quantitative way white light, ultraviolet or laser induced emission spectra from biological components (e.g., oxygenated and deoxygenated hemoglobin in retinal blood vessels and or melanin pigmentation level in the retina) and, to distinguish cancer from healthy, or otherwise diseased tissue or cells. The signals produced by thus induced emission spectroscopy can be used to characterized different components in tissues. This method further enables the identification and spatial mapping of proteins, sacharides, $AND^+$ and NADH, collagen, elastin and flavin, and various additional metabolic mediators within cells and/or tissues. Using emission light at certain wavelengths and analyzing it by various algorithms, the tissue (or cell) alkalinity or acidity, blood perfusion as well as the presence of a neoplasm in a tissue could be detected, mapped and characterized. The sensitivity of the detection can be enhanced by the use of various fluorescing tags. These tags can be used to tag malignancy (neoplasm) at the cell and/or tissue levels, making this method one of the most rapidly developing areas of cancer diagnostics and eventually therapy. There is a variety of laboratory systems worldwide for the detection of emitted light from biological samples. Nowadays, one of the key issues in the medical field is how to analyze the resulting signals and images from these diagnostic detection systems, which key issue is addressed in the present invention.

There is thus a widely recognized need for, and it would be highly advantageous to have, a spectral bio-imaging methods for medical diagnostics and therapy and for biological research devoid of the above described limitations, which provides advanced means to detect the spatial organization, to quantify and meaningfully display cellular and tissue components and administered probes and drugs, using light transmission, reflection, scattering or fluorescence emission strategies.

SUMMARY OF THE INVENTION

According to the present invention there are provided spectral imaging methods for biological research, medical diagnostics and therapy, which methods are referred to hereinbelow as spectral bio-imaging methods. The methods of the present invention can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high sensitivity and high spatial and spectral resolutions.

According to further features in preferred embodiments of the invention described below, the spectral bio-imaging method comprising the steps of (a) preparing a sample to be spectrally imaged; (b) viewing the sample through an optical device, the optical device being optically connected to an imaging spectrometer, the optical device and the imaging spectrometer being for obtaining a spectrum of each pixel of the sample by: (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a that are having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating one or more of the elements of the interferometer system, so that the optical path difference between the two coherent beams generated by the interferometer system is scanned simultaneously for all the pixels of the sample; and (v) recording signals of each of the detector elements as function of time using a recording device to form a first spectral cube of data; and (c) interpreting the first spectral cube of data using a mathematical algorithm.

According to still further features in the described preferred embodiments the method further comprising the step of: (d) displaying a map of the interpreted spectral cube of data.

According to still further features in the described preferred embodiments the optical device is selected from the group consisting of a microscope, a camera lens, an endoscope, a fundus camera and a funduscope.

According to still further features in the described preferred embodiments the microscope is selected from the group consisting of a reflection microscope, a transmission microscope, a fluorescence microscope, an upright microscope, an inverted microscope, a dark field microscope, a confocal microscope, a standing wave confocal microscope and a reflection contrast microscope.

According to still further features in the described preferred embodiments the collimated light is selected from the group consisting of light transmitted through the sample, light reflected from the sample, light scattered from the sample and light emitted from the sample.

According to still further features in the described preferred embodiments the light emitted from the sample is selected from the group consisting of administered probe fluorescence, administered probe induced fluorescence and auto-fluorescence.

According to still further features in the described preferred embodiments the light originates from a source selected from the group consisting of laser, white light, filtered light, ultraviolet light and a light having a small wavelength range.

According to still further features in the described preferred embodiments the light originates from a multiplicity of light sources, the sources operate simultaneously or successively.

According to still further features in the described preferred embodiments the two-dimensional array is a CCD such as a video rate CCD, a cooled high dynamic range CCD, an intensified CCD or a time gated intensified CCD.

According to still further features in the described preferred embodiments the sample is selected from the group consisting of a cell, a tissue and an organism.

According to still further features in the described preferred embodiments the cell and the tissue are from a human.

According to still further features in the described preferred embodiments the cell is for example a cell collected by a Pap smear, a blood cell, a fetal cell, a cell suspected of being malignant, a cell during interphase, a cell during mitosis and a cell during meiosis.

According to still further features in the described preferred embodiments the tissue is selected from the group consisting of eye retina, a retinal blood vessel, a tumor, skin, cornea, hair, lungs, stomach, intestines, bladder, colon, prostate, cervix, arteries, veins and heart.

According to still further features in the described preferred embodiments the sample is the eye retina and the method is for detecting oxygenated and deoxygenated hemoglobin in the retinal blood vessels and/or for detecting melanin pigmentation level in the retina.

According to still further features in the described preferred embodiments the sample is selected from the group consisting of a cell, a tissue section and an organism; the light is induced by a probe, the probe binds to a specific cellular constituent, the method is for detecting the presence or the level of the cellular constituent.

According to still further features in the described preferred embodiments is the probe includes a conjugated fluorescent moiety and the induction is a fluorescence light emission of the fluorescent moiety.

According to still further features in the described preferred embodiments the probe further includes a nucleic acid molecule, the method is for detecting the presence or the level of a cellular nucleic acid (deoxyribonucleic acid and/or ribonucleic) hybridizing with the nucleic acid molecule.

According to still further features in the described preferred embodiments the probe includes an antibody, the method is for detecting the presence or the level of a cellular protein recognized by the antibody.

According to still further features in the described preferred embodiments the fluorescent moiety is for example SPECTRUMORANGE and SPECTRUMGREEN, are rhodamine and fluorescein derivatives, respectively, Aqua, Texas-Red, FITC, rhodamine, fluorescein, cascade blue and any combination thereof.

According to still further features in the described preferred embodiments the mathematical algorithm is a point operation analysis of the spectrum of each of the pixels in the sample.

According to still further features in the described preferred embodiments the point operation analysis includes mapping the spectrum of each of the pixels in the sample into a scalar according to a transformation function.

According to still further features in the described preferred embodiments the point operation analysis includes mapping the spectrum of each of the pixels of the sample into another spectrum according to a transformation function.

According to still further features in the described preferred embodiments the mathematical algorithm is a morphological analysis, the morphological analysis may follow any spectral analysis such as similarity mapping..

According to still further features in the described preferred embodiments the mathematical algorithm is a similarity mapping analysis for computing for each of the pixels in the sample a spectral difference from a reference spectrum.

According to still further features in the described preferred embodiments the similarity mapping analysis results in generating a gray level or a pseudocolor image, in which bright pixels correspond to a small spectral difference and dark pixels correspond to a large spectral difference.

According to still further features in the described preferred embodiments the similarity mapping analysis results in generating a gray level or a pseudocolor image, in which bright pixels correspond to a large spectral difference and dark pixels correspond to a small spectral difference.

According to still further features in the described preferred embodiments the spectral difference is a scalar defined as the integral over a predefined wavelength range of the absolute value of the difference between the spectrum of each of the pixels and the reference spectrum.

According to still further features in the described preferred embodiments the mathematical algorithm is a classification mapping analysis computing for the spectrum of each of the pixels a spectral difference from several reference spectra.

According to still further features in the described preferred embodiments the classification mapping analysis results in generating a pseudocolors image, in which groups of pixels having a predetermined maximal spectral differences from one of the several reference spectra are colored with a predetermined pseudocolor.

According to still further features in the described preferred embodiments the spectral difference is a scalar defined as the integral over a predefined wavelength range of the absolute value of the difference between the spectrum of each of the pixels and one of the several reference spectra.

According to still further features in the described preferred embodiments the mathematical algorithm is a principal component analysis.

According to still further features in the described preferred embodiments the principal component analysis includes: (a) building a covariant matrix for all of the pixels and the wavelengths of the measurement, including wavelengths of exciting sources when multiple wavelengths are used; (b) diagonalizing the covariant matrix and finding all independent orthogonal spectral base elements; (c) finding which of the base elements tag certain features in the sample.

According to still further features in the described preferred embodiments the mathematical algorithm is a linear combination analysis.

According to still further features in the described preferred embodiments the linear combination analysis includes applying an arithmetical function between corresponding wavelengths of corresponding pairs of pixels belonging to the first spectral cube of data and to a second spectral cube of data, to obtain a resulting third spectral cube of data.

According to still further features in the described preferred embodiments the linear combination analysis is for a purpose selected from the group consisting of averaging two spectral cubes of data, time changes follow-up and spectral normalization.

According to still further features in the described preferred embodiments the linear combination analysis includes applying a given scalar to every wavelength of the spectra of each of the pixels by an arithmetical function, the function is selected from the group consisting of addition, subtraction, multiplication, division and combinations thereof.

According to still further features in the described preferred embodiments the linear combination analysis is used for background subtraction in which a spectrum of a pixel located in a background region of the sample is subtracted from the spectra of the pixels of the sample.

According to still further features in the described preferred embodiments the linear combination analysis is used for a calibration procedure in which a spectrum measured prior to the viewing the sample is used to divide the spectra of the pixels of the sample.

According to still further features in the described preferred embodiments the mathematical algorithm is an optical density analysis.

According to still further features in the described preferred embodiments the optical density analysis is for obtaining an interpreted image which is an optical density map.

According to still further features in the described preferred embodiments the mathematical algorithm computes a Red-Green-Blue color image using predefined wavelength ranges.

According to still further features in the described preferred embodiments the mathematical algorithm computes a ratio between intensities at two different wavelengths for each of the spectra of the pixels.

According to still further features in the described preferred embodiments the mathematical algorithm computes a ratio between intensities at two different wavelengths for each of the spectra of the pixels and paints each of the pixels in a lighter or darker artificial color, according to the computed ratio.

According to still further features in the described preferred embodiments the method is used for spectral identification of multiple fluorophores administered to the sample.

According to still further features in the described preferred embodiments the method is used for detecting microenvironmental changes such as local electrical potential, pH level and intracellular ions concentration in the sample.

According to still further features in the described preferred embodiments the method is used for measuring auto-fluorescence from a natural constituent such as chlorophyll, porphyrins and/or cytoplasmic proteins in the sample.

According to still further features in the described preferred embodiments the method is used for an application selected from the group of applications consisting of biology research, drug development industry, cell and tissue classification in pathology, hematology, urine analysis for the presence of types of bacteria, gene identification and mapping in chromosomes, genetic disease diagnosis, cell organelles anatomy and physiology, chromatin distribution and condensation in a cell nuclei, cytoplasm organelles and constituents mapping, cell membrane mapping, nuclear membrane mapping, mapping of skin cancers, differentiating between melanoma and nevi, port wine stains mapping and, skin imaging before, during, and after a photodynamic therapy treatment.

According to still further features in the described preferred embodiments the cytoplasm constituents are selected from the group consisting of $AND^+$, NADH, flavin and cytochromes.

According to still further features in the described preferred embodiments the method is used for measuring fluorescence resonance energy transfer to determine spatial separation between at least two fluorophores in the sample, at least one of the fluorophores is externally administered to the sample.

According to still further features in the described preferred embodiments the sample is selected from the group consisting of a cell, a tissue and an organism, the method is for identifying and mapping cellular and subcellular details in the sample.

According to still further features in the described preferred embodiments the sample is stained using a method selected from the group consisting of Romanowsky-Giemsa staining, Haematoxylin-Eosin staining and May-Grunwald-Giemsa staining.

According to still further features in the described preferred embodiments the subcellular details are types of chromatin organization in the nucleus, the types are selected from the group consisting of heterochromatin and euchromatin.

According to still further features in the described preferred embodiments the sample is selected from the group consisting of a cell, tissues and organisms, the method is for monitoring life processes in the sample as function of time.

According to still further features in the described preferred embodiments the method is a fluorescent in situ hybridization method comprising the steps of: (a) labeling with at least one fluorescent dye at least one nucleic acid molecule to obtain at least one fluorescently tagged nucleic acid probe; (b) hybridizing the probe in situ with cellular nucleic acids of a biological sample; or, alternatively or additionally (a) hybridizing at least one nucleic acid probe in situ with cellular nucleic acids of a biological sample; (b) labeling each of the at least one probe with at least one fluorescent dye; either way these steps are followed by (c) viewing the biological sample through a fluorescence microscope, the fluorescence microscope being optically connected to an imaging spectrometer, the fluorescence microscope and the imaging spectrometer being for obtaining a spectrum of each pixel of the biological sample by: (i) collecting incident light simultaneously from all pixels of the biological sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the biological sample for the entire duration of the measurement, so that the real image of the biological sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating one or more of the elements of the interferometer system, so that the optical path difference between the two coherent beams generated by the interferometer system is scanned simultaneously for all the pixels of the biological sample; and (v) recording signals of each of the detector elements as function of time using a recording device to form a first spectral cube of data; and (d) interpreting the first spectral cube of data using a mathematical algorithm, the mathematical algorithm is a linear combination for background subtraction and/or classification mapping analysis.

According to still further features in the described preferred embodiments the method is a cell classification method comprising the steps of: (a) preparing a smear of cells for analysis; (b) viewing the smear of cells through a transmission microscope, the transmission microscope being optically connected to an imaging spectrometer, transmission microscope and the imaging spectrometer being for obtaining a spectrum of each pixel of the smear of cells by: (i) collecting incident light simultaneously from all pixels of the smear of cells using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the smear of cells for the entire duration of the measurement, so that the real image of the smear of cells is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating one or more of the elements of the interferometer system, so that the optical path difference between the two coherent beams generated by the interferometer system is scanned simultaneously for all the pixels of the smear of cells; and (v) recording signals of each of the detector elements as function of time using a recording device to form a first spectral cube of data; and (c) interpreting the first spectral cube of data using a principal component algorithm.

The present invention successfully addresses the shortcomings of the presently known configurations by providing a method allowing spectroscopic measurement and data to be collected for every point (i.e., pixel) of a sample independently and simultaneously, it provides both information on materials and molecule types and concentrations as function of position in the sample, and conventional imaging information which allows conventional morphological analysis (as described for example in U.S. Pat No. 4,965,725 to Rutenberg), at the same time. Hence, the present invention can be used for both the detection of spatial organization and quantification of cellular and tissue components, structures, organelles, genetic material, administered fluorescent tagging probes, and the distribution within cells and tissues of administered drugs, using light transmission, reflection, scattering and fluorescence strategies with high spatial and spectral resolution. An additional advantage of the present invention is in the increased simplicity of interpretation of the spectroscopic data. An additional advantage of the present invention is the well known Fellgett or multiplex advantage of Fourier transform spectroscopy over filters, gratings and other types of dispersion techniques, which expresses itself in an increased signal-to-noise ratio in spectral measurements. An integral part of the present invention are a number of mathematical algorithms that the computer software must use to interpret and display the data in a meaningful way.

BRIEF DESCRIPTION OF THE DRAWINGS

The invention herein described, by way of example only, with reference to the accompanying drawings, wherein:

FIG. 4 is shows a definition of pseudo-RGB (Red, Green and Blue) colors for emphasizing chosen spectral ranges. The intensity for each pseudo-color is calculated by integrating the area under the curve, after multiplying it by one of the curves.

FIGS. 5a and 5b show (a) a fluorescence spectral image of a cell stained with propidium iodide using a SpectraCube™ based spectral bio-imaging system attached to an Olympus inverted microscope (IMT2); and (b) a plot of the fluorescence emission spectra from three individual pixels of the image shown in FIG. 5a, according to the methods of the present invention;

FIGS. 8a and 8b show (a) a plasma cell stained by the method of May-Grunwald-Giemsa for staining blood cells; and (b) different subcellular sites (A–E) of the cell of FIG. 8a;

FIGS. 30a, 30b and 30c show (a) a black and white intensity image obtained using the values of the vector product BV$_{20}$ of FIG. 29 as pixel intensities; (b and c) black and white intensity images obtained using the values of the vector products BV$_{10}$ and BV$_{13}$ of FIG. 29, respectively.

DESCRIPTION OF THE PREFERRED EMBODIMENTS

The present invention is of spectral bio-imaging methods which can be used for medical diagnostics, therapy and biological research. Specifically, the present invention can be used to detect the spatial organization and to quantify cellular and tissue constituents, structures and administered components such as probes and drugs, using light transmission, reflection, scattering and fluorescence emission strategies, with high spatial and spectral resolutions. Thus, the present invention enables interpretation and useful display of results in a primarily enhanced imaging form, in order to, for example, study anatomy and physiology of living cells, efficiently map many genes and chromosomes in one single measurement, detect and identify cancerous or otherwise diseased cells and tissues in sections under a microscope or in vivo through a macro lens or through any type of endoscope or fundus camera etc., for example, for the purpose of guiding the surgeon during surgery on the tissue to be removed.

Figure 1:
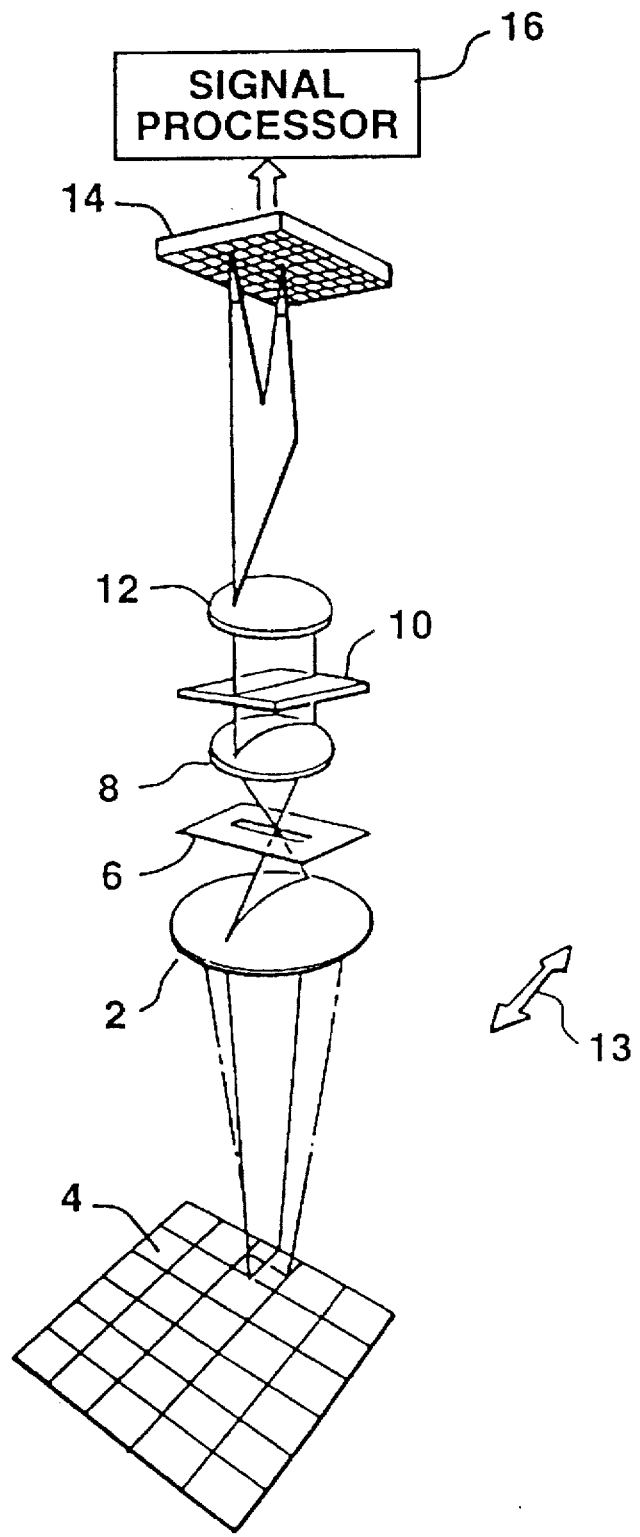
FIG. 1 illustrates a conventional (prior art) slit-type imaging spectrometer.

For purposes of better understanding the present invention, as illustrated in FIGS. 4–30 of the drawings, reference is first made to the construction and operation of a conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system as indicated at 2, for collecting the incident light from a scene, schematically indicated at 4 and focusing the substantially parallel light of the scene 4 onto a first focal plane occupied by a slit 6 to define the field of view. The light exiting from slit 6 is collimated in a collimator lens 8 and is passed through a spectral dispersion element 10 (e.g., a grating) to separate the various wavelengths. The output from spectral dispersion element 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., a raster movement or line scanning indicated by arrow 13) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time. This is necessary to separate the spectra of each pixel.

As mentioned in the background section and hereinabove, the disadvantage of the prior art method illustrated in FIG. 1 is that most of the pixels of one frame are not measured at any given time even though the optical system 2 actually collects energy from all of them simultaneously. As a result, the required frame time is significantly increased, and/or the signal-to-noise ratio (sensitivity) is substantially decreased with respect to a system which does not have the need for such a slit.

Figure 2:
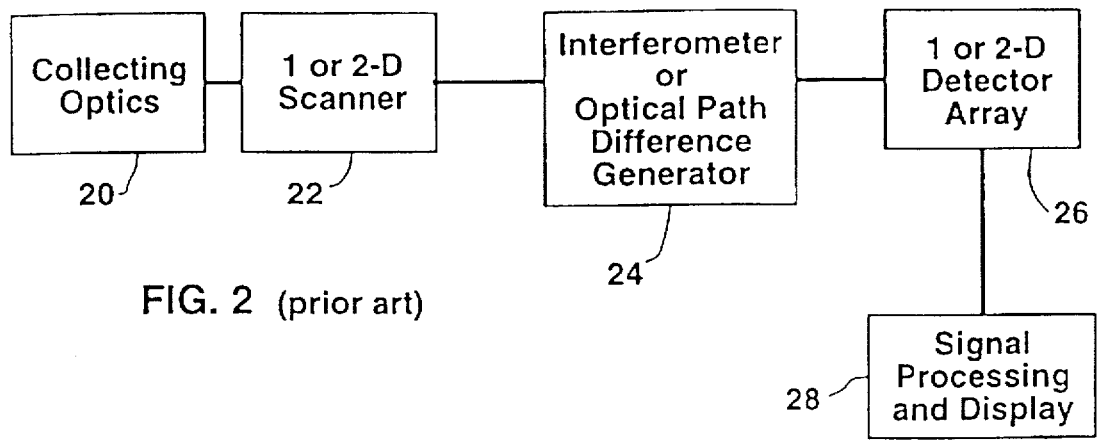
FIG. 2 is a block diagram illustrating the main components of an imaging spectrometer constituted in accordance with U.S. patent application Ser. No. 08/392,019 (prior art)

FIG. 2 is a block diagram illustrating the main components of an improved prior art imaging spectrometer disclosed in U.S. patent application Ser. No. 08/392,019 to Cabib et al., filed Feb. 21st, 1995 which is incorporated by reference as if fully set forth herein. This imaging spectrometer is constructed highly suitable to implement the methods of the present invention.

Thus, the prior art imaging spectrometer of FIG. 2 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. patent application Ser. No. 08/392,019 may be practiced in a large variety of configurations. Specifically, the interferometer used may be combined with other mirrors as described in the relevant Figures of U.S. patent application Ser. No. 08/392,019.

Thus, according to U.S. patent application Ser. No. 08/392,019, alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, and (4) a four-mirror plus beamsplitter interferometer as further described in the cited U.S. patent application.

Figure 3:
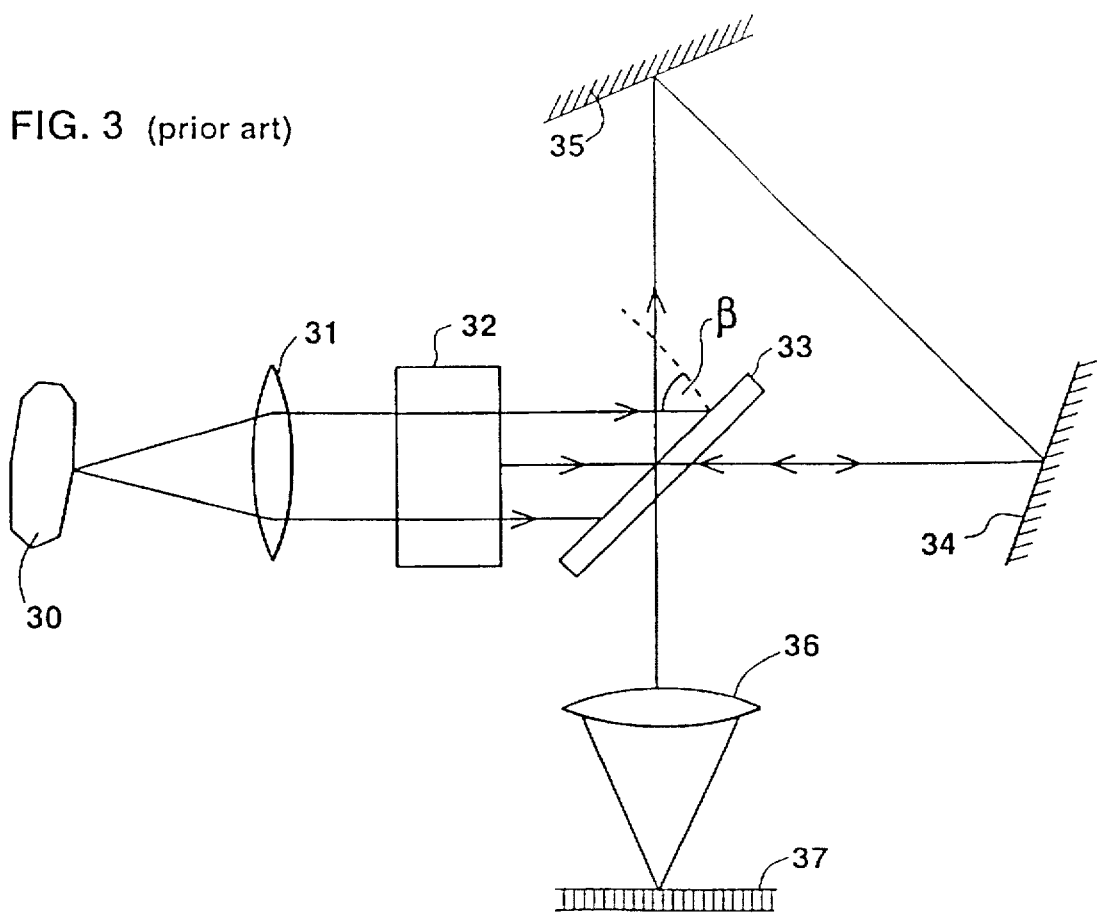
FIG. 3 illustrates a non-moving type interferometer, namely, a Sagnac interferometer, as used in an imaging spectrometer in accordance with U.S. patent application Ser. No. 08/392,019 (prior art)
Figure 6:
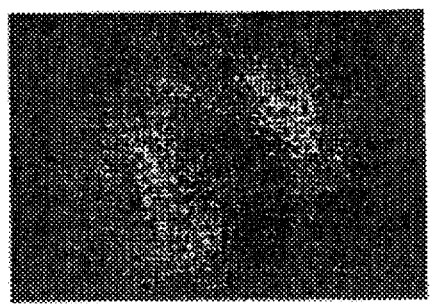
FIGS. 6a, 6b, 6c and 6d show (a) an RGB pseudo-color image of a cell during mitosis, the mitotic cell has been stained with acridine orange; (b) a plot of two of the spectra measured to create the spectral image of the cell, a first spectrum (marked M) from a cytoplasmic region characterized by a monomeric form of acridine orange and a second spectrum (marked D) from a nuclear region characterized by a dimeric form of acridine orange; (c) result of a similarity mapping analysis using the spectrum of the dimeric form of acridine orange as a reference spectrum; and (d) results of a similarity mapping analysis using the spectrum of the monomeric form of acridine orange as a reference spectrum.
Figure 6:
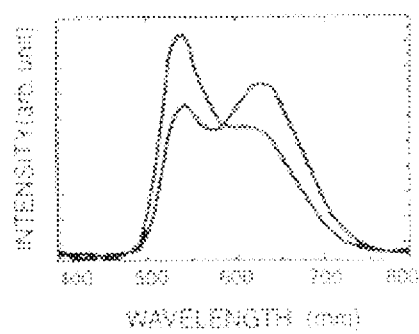
Figure 6:
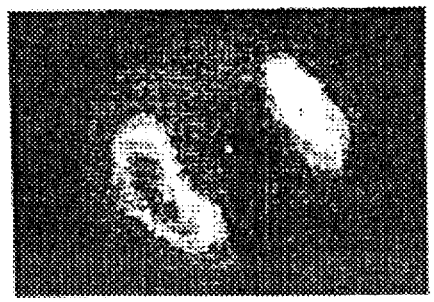
Figure 6:
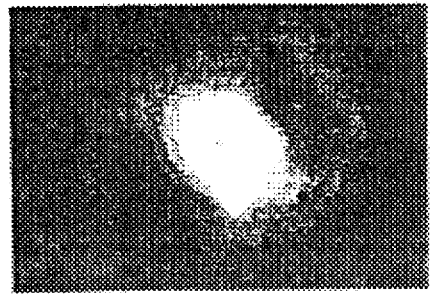
Figure 7:
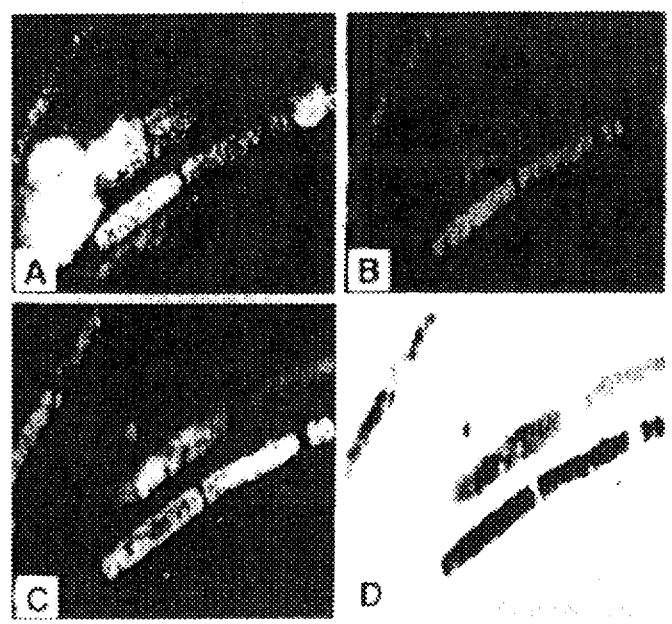
FIGS. 7a, 7b, 7c, 7d and 7e show (a) the total emitted fluorescence from Oedogoniurn sp. alga; (b) similarity mapping analysis with spectrum A of FIG. 7e as a reference; (c) similarity mapping analysis using as reference a faint red fluorescence spectrum of the image in FIG. 7a; (d) similarity mapping analysis using spectrum B of FIG. 7e as a reference; and (e) fluorescence spectra from is four different pixels of the specimen shown in FIGS. 7a–d.
Figure 7:
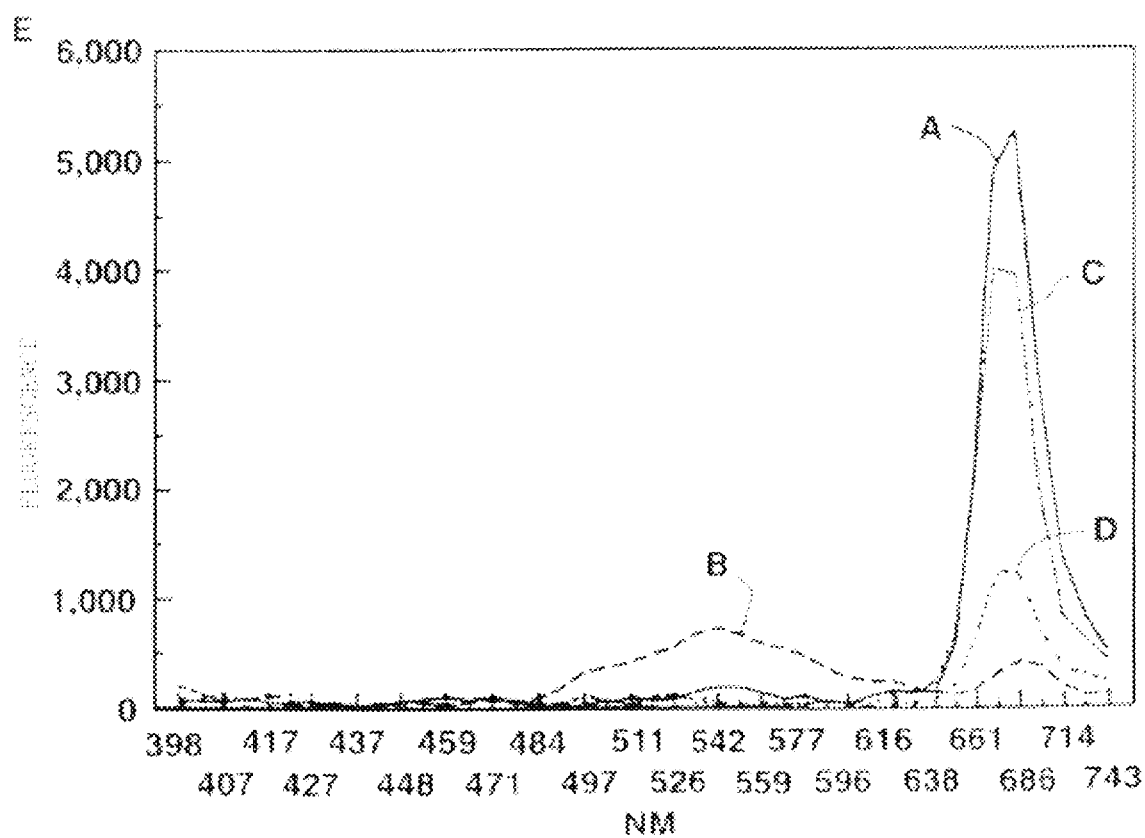
Figure 8:
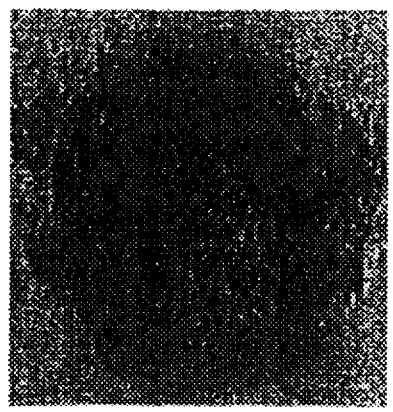
Figure 8:
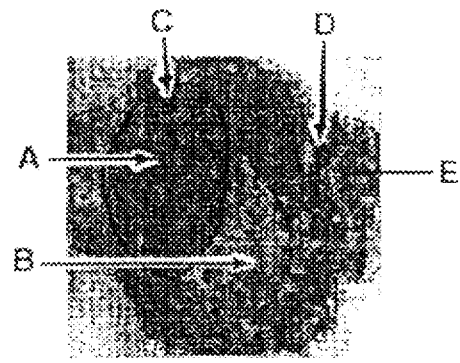
Figure 9:
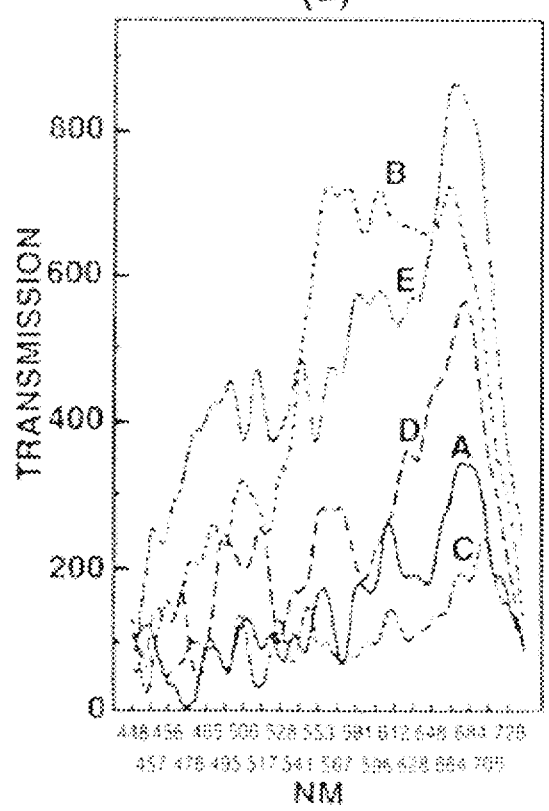
FIGS. 9a and 9b show (a) transmitted light spectra from five individual pixels pointed out by arrows in FIG. 8b; and (b) absorbance of corresponding spectra shown in FIG. 9a calculated relative to incident light recorded outside of the cell of FIGS. 8a and 8b.
Figure 9:
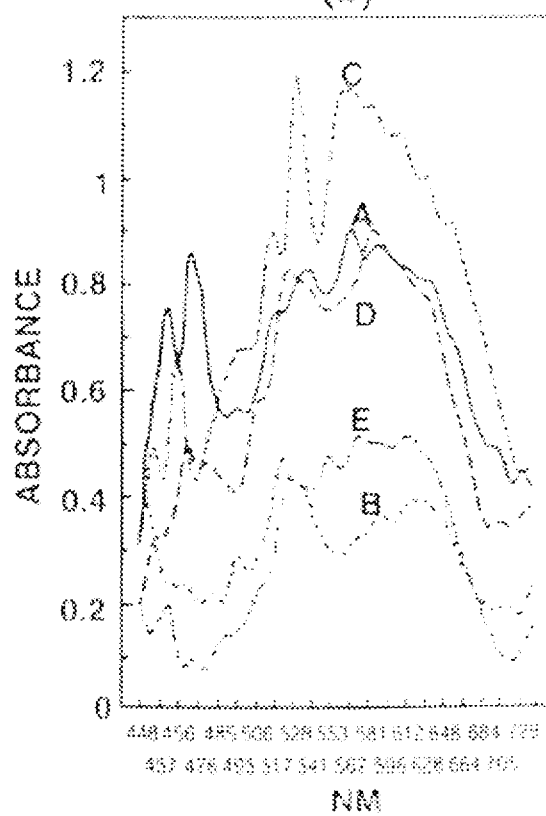
Figure 10:
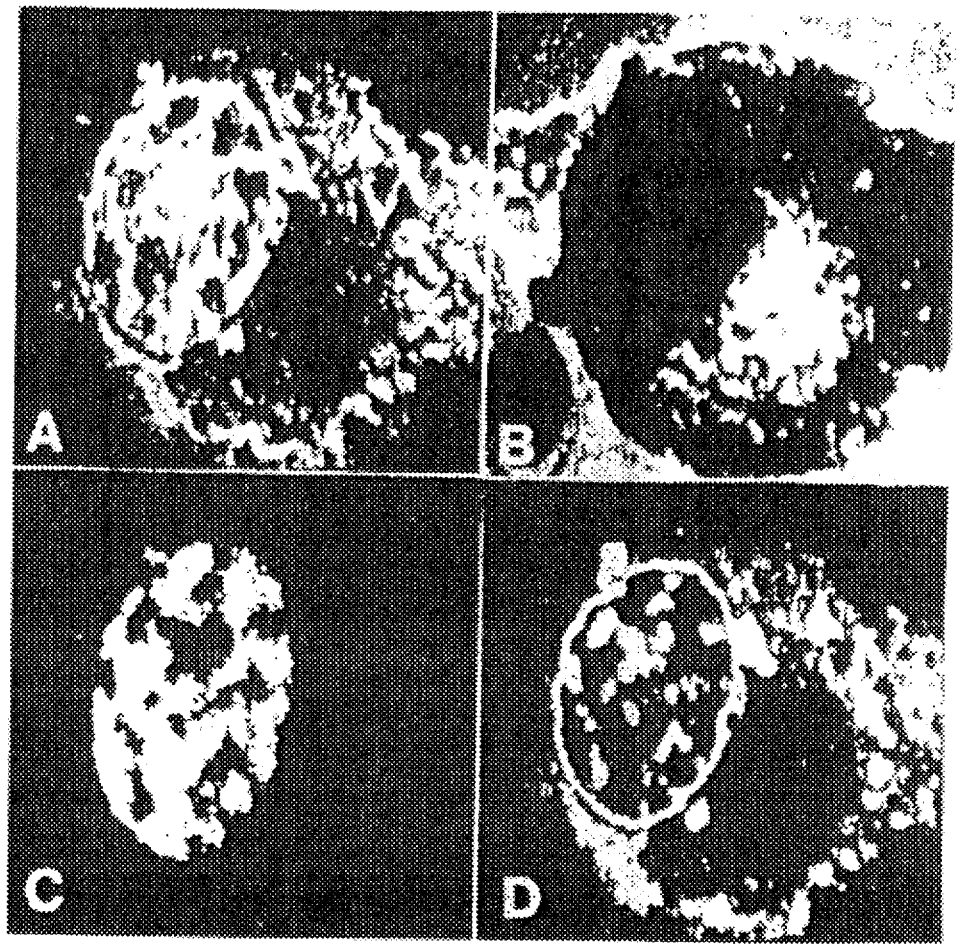
FIGS. 10a, 10b, 10c and 10d show quantitative similarity mapping analyses when spectra A, B, C and D/E shown in FIG. 9a are used, one at the time, as a reference spectrum, respectively.
Figure 11:
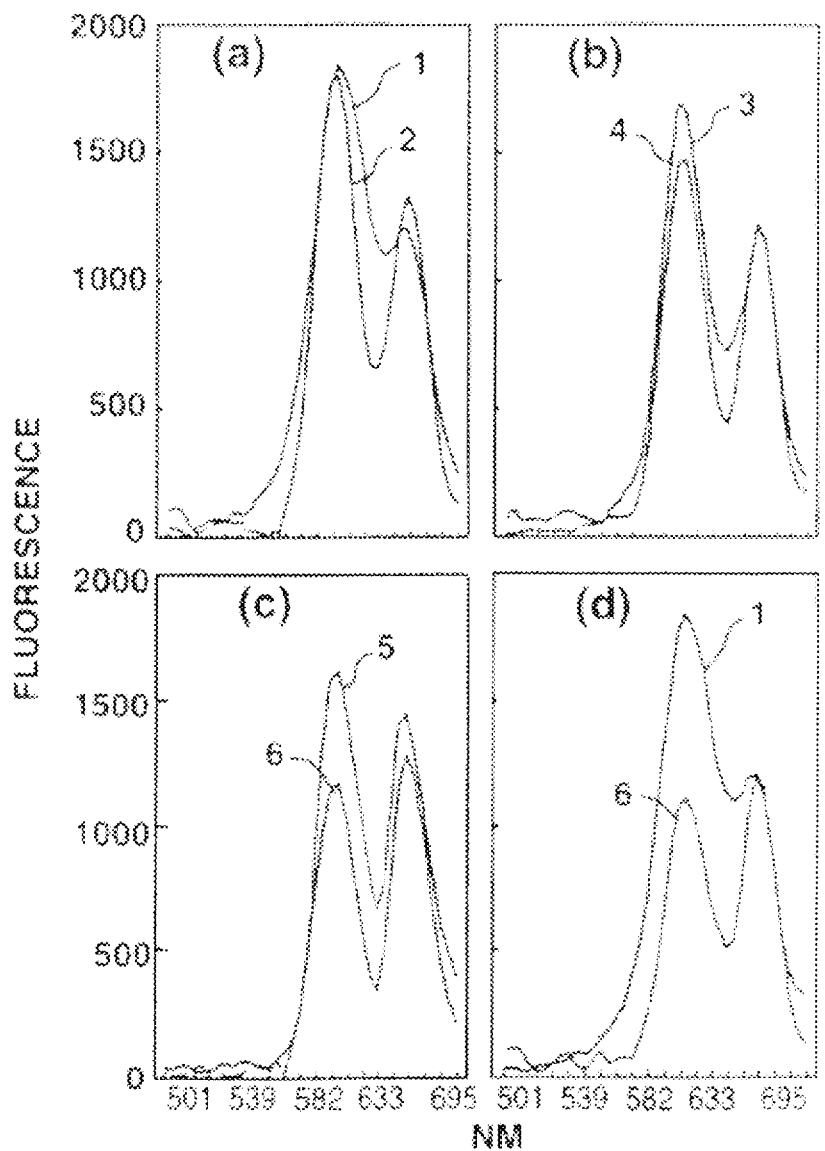
FIGS. 11a, 11b, 11c and 11d show a fluorescence pixel spectra of four different sites of the Paramecium seen in FIG. 12a, wherein living Paramecium were analyzed by the SpectraCube™ system attached to a fluorescence microscope (Olympus BH2 RFC), the Paramecium cells were excited by a green light source (band pass maximum 545 nm), and the red fluorescence was measured by the system.
Figure 12:
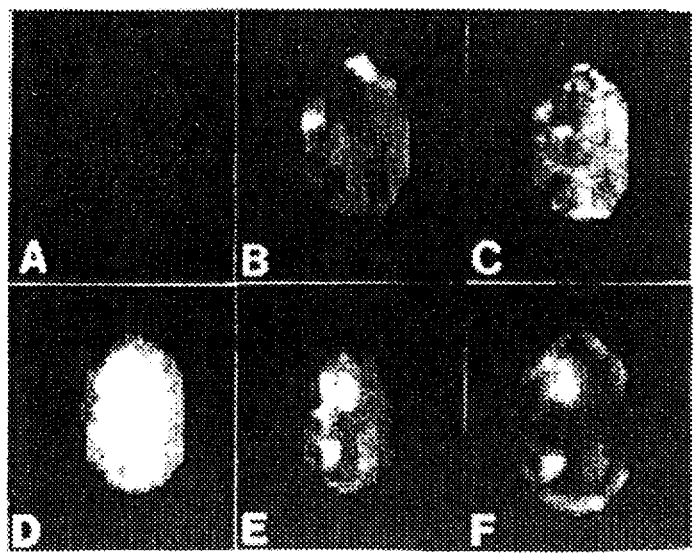
FIGS. 12a, 12b, 12c, 12d, 12e, 12f show fluorescence images of Paramecium due to ingested algae, and analyses thereof wherein (a) Paramecium cells were excited by a green light source (band pass maximum 545 nm), and red fluorescence emission was visualized through a cut-on red filter (590 nm); (b) similarity mapping analysis based on spectrum 1 of FIG. 11a revealed two distinct regions on the upper part of the Paramecium, high content of native algal chlorophyll, and, therefore, possibly representing the cytopharynx and the buccal cavity; (c) vacuolar spots of nearly one pixel each (mapped with spectrum 2 of FIG. 11a), next to the cytopharynx; (d) and (e) mapped with spectra 4 and 5 of FIGS. 11b and 11c, respectively, show large vacuoles in the middle of the cytoplasm, delineating narrow regions of the same compartment; (f) a major cytoproct region mapped with spectrum 6 of FIG. 11d, where digested waste is eliminated from the cell.

FIG. 3 illustrates an imaging spectrometer constructed in accordance with U.S. patent application Ser. No. 08/392,019 utilizing an interferometer in which the OPD varies with the angle of incidence of the incoming radiation. A beam entering the interferometer at a small angle to the optical axis undergoes an OPD which varies linearly with this angle.

In the interferometer of FIG. 3, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\sigma$) to the optical axis undergoes an OPD which is a function of the thickness of the beamsplitter 33, its index of refraction, and the angle $\sigma$. The OPD is proportional to $\sigma$ for small angles. By applying the appropriate inversion, and by careful bookkeeping, the spectrum of every pixel is calculated.

In the configuration of FIG. 3, in a situation where beamsplitter 33 is at 45° with regard to optical axis, the ray which is incident on the beamsplitter at an angle $\beta(\beta=45°)$ goes through the interferometer with an OPD=0, whereas a ray which is incident at a general angle $\beta-\sigma$ undergoes an OPD given by the following:

$$OPD(\Gamma,\sigma,t,n)=t[(n^2-\sin^2(\beta+\sigma))^{0.5}-(n^2-\sin^2(\beta-\sigma))^{0.5}+2\sin\beta\sin\sigma] \quad (1)$$

where, $\beta$ is the angle of incidence of the ray on the beamsplitter (60°); $\sigma$ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution $s$ of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. patent application Ser. No. 08/392,019 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

An imaging spectrometer in accordance with the invention disclosed in U.S. patent application Ser. No. 08/392,019 was developed by Spectral Diagnostics (SD) Ltd., Industrial Park, Migdal Haemek, Israel and will be refined hereinbelow as SpectraCube™. The SpectraCube™ system optically connected to a variety of optical devices was used to implement the methods of the present invention. The SpectraCube™ system has the following characteristics, listed hereinbelow in Table 1:

TABLE 1

| Character | Performance |
| --- | --- |
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

The SpectraCube™ system easily attaches to any microscope or macro lens with, for example, C-mount or F-mount connectors, and can stand in any orientation during the measurement. The system may as well be connected to other magnification means and to various types of endoscopes and cameras. Therefore, spectral images of cells and tissues in various magnification and lighting strategies may be obtained.

DISPLAY AND ANALYSIS OF SPECTRAL IMAGES a. General

As mentioned above, a spectral image is a three dimensional array of data, I(x,y,λ), that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set i.e., a spectral cube.

One possible type of analysis of a spectral cube is to use spectral and spatial data separately, i.e., to apply spectral algorithms to the spectral data and two-dimensional image processing algorithms to the spatial data.

As an example for a spectral algorithm consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., I(x,y,λ)), is visualizing that data structure in a meaningful way. Unlike other types of 3D data such as tomographic data, D(x,y,z), obtained for example by a confocal microscope, where each point represents, in general, the intensity at a different locations (x,y,z) in tree-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x,y) = \int_{\lambda 2}^{\lambda 1} w(\lambda) \cdot I(x,y,\lambda) d\lambda \quad (3)$$

In equation 3, w(λ) is a general weighting response function that provides maximum flexibility in computing a variety of gray scale images, all based on the integration of an appropriately weighted spectral image over some spectral range. For example, by evaluating equation (3) with three different weighting functions, $\{w_r(\lambda), w_g(\lambda), w_b(\lambda)\}$, corresponding to the tristimulus response functions for red (R), green (G) and blue (B), respectively, it is possible to display a conventional RGB color image. It is also possible to display meaningful non-conventional (pseudo) color images. FIG. 4 presents an example of the power of this simple algorithm. Consider choosing $\{w_r, w_g, w_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant.

The concept of point operations can also be extended to spectral images: here each pixel has its own intensity function (spectrum), i.e., an n-dimensional vector $V_1(\lambda)$; $\lambda \in [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \in [\lambda_1, \lambda_n] \qquad (4)$$

Building a gray scale image according to Equation 4 is an example of this type of point operation. In the more general case, a point operation maps the spectrum (vector) of each pixel into another vector according to a transformation function:

$$V_2(l) = g(V_1(\lambda)); l \in [1, N], \lambda \in [\lambda_1, \lambda_n] \qquad (5),$$

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10} I(\lambda)/I_0(\lambda) = -\log_{10} \tau(\lambda) \qquad (6)$$

where $OD(\lambda)$ is the optical density as a function of wavelength, $I(\lambda)$ is the measured spectrum, $I_0(\lambda)$ is a measured reference spectrum, and $\tau(\lambda)$ is the spectral transmitance of the sample. Equation 6 is calculated for every pixel for every wavelength where $I_0(\lambda)$ is selected from (1) a pixel in the same spectral cube for which OD is calculated; (2) a corresponding pixel in a second cube; and (3) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known. It should thus be noted that the term 'level' as used hereinbelow in the claims also refers to the terms 'amount', 'relative amount', 'absolute concentration' and 'relative concentration'.

Additional examples include various linear combination analyses, such as for example: (1) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (2) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

C. Spatial-spectral combined operations

In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (1) classify each pixel in the image as belonging to one of k+1 classes (k cell types plus a background) according to its spectrum; (2) segment the image into the various cell types and count the number of cells from each type; and (3) sum the fluorescence energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. The ideal type of measurement for this type of situation is a spectral image. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; i=1, 2, ..., k , $\lambda \in [\lambda_1, \lambda_n]$, and the measured spectrum at each pixel (x, y) is $s_{x,y}(\lambda)$, $\lambda \in [\lambda_1, \lambda_n]$, then the following algorithm is a possible method of classification (step 1 above):

Let $e^2_i$ be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2 \qquad (7)$$

where $R_\lambda$ is the spectral region of interest. Each point [pixel (x,y)] in the image can then be classified into one of the k+1 classes using the following criterion:

$$\text{point}(x,y) \in \text{class } k + 1 \text{ if } e_i^2 > \text{threshold for all } i \in [1,k], \qquad (8)$$

-continued whereas point(x,y) ∈ class ρ if $e_i^2$ < threshold, and

ρ is such that $\min[e_i^2] = e_\rho^2$

Steps 2 and 3 above (image segmentation and calculation of average fluorescence intensity) are now straightforward using standard computer vision operations on the synthetic image created in accordance with the algorithm described in equations 7 and 8.

Another approach is to express the measured spectrum $s_{x,y}(\lambda)$ at each pixel as a linear combination of the k known fluorescence spectra $s_i(\lambda)$; i=1, 2, ..., k. In this case one would find the coefficient vector $C=[c_1, c_2, ..., c_k]$ that solves:

$$F = \min \sum_{\lambda \in R_\lambda} (s(\lambda) - \hat{s}(\lambda))^2 \quad (9)$$

where $\hat{s}(\lambda) = \sum_{i=1}^{k} c_i \cdot s_i(\lambda)$,

Solving for $$\frac{dF}{dc_i} = 0;$$

for i=1,2, ..., k (i.e., find values of $c_i$ which minimize F) yields the matrix equation $C=A^{-1}B$ (10), where A is a square matrix of dimension k with elements $$a_{m,n} = \left[ \sum_{\lambda \in R_\lambda} s_m(\lambda) \cdot s_n(\lambda) \right], \quad (11)$$

and B is a vector defined as $$b_m = \left[ \sum_{\lambda \in R_\lambda} s_m(\lambda) \cdot s(\lambda) \right], m,n = 1,2, ..., k \quad (12)$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases objects (e.g., cells) present in a spectral image differ from one another in chemical constituents and/or structure to some degree. Using a principal component analysis by producing covariance or correlation matrices enhances these small differences. A brief description of the principal component analysis using a covariance matrice is given below. For further details regarding the principal component analysis, the reader is referred to Martens and Naes (1989) Multivariate Calibration, John Wiley & Sons, Great Britain; and to Esbensen et al., Eds. (1994) Multi variance analysis—in practice. Computer-aided modeling as CAMO, and the Unscrambler's User's guide, Trondheim, Norway.

Thus, the intensities of the pixels of the image at wavelength $\lambda_i$(i=1, ... N) are now considered a vector whose length is equal to the number of pixels q. Since there are N of these vectors, one for every wavelength of the measurement, these vectors can be arranged in a matrix B' with q rows, and N columns:

$$B' = \text{No. of pixels} \begin{array}{c} \overbrace{\begin{array}{ccc} B'_{11} & ... & B'_{1N} \\ \cdot & & \cdot \\ \cdot & & \cdot \\ \cdot & & \cdot \\ B'_{q1} & ... & B'_{qN} \end{array}}^{\text{No. of wavelengths}} \end{array} \quad (13)$$

For each of the columns of matrix B' defined is an average:

$$M_i = \frac{1}{q} \sum_{i=1}^{q} B'_{ji}; i = 1 ... N \quad (14)$$

and a second normalized matrix B defined as:

$$B = \text{No. of pixels} \begin{array}{c} \overbrace{\begin{array}{ccc} B'_{11}/M_1 & ... & B'_{1N}/M_N \\ \cdot & & \cdot \\ \cdot & & \cdot \\ \cdot & & \cdot \\ B'_{q1}/M_1 & ... & B'_{qN}/M_N \end{array}}^{\text{No. of wavelengths}} \end{array} \quad (15)$$

A covariance matrix C is defined for the matrix B: $C=B^T \cdot B$ of dimensions N×N. C is diagonalyzed, and eigenvectors and eigenvalues related by: $C \cdot V_i = \mu_i V_i$ where Vi are N orthogonal unit vectors and $\mu_i$ are the eigenvalues representing the variance in the direction of the i-th unit vector $V_i$. In general, the lowest components represent the highest variability as a function of pixels.

The products $BV_i$(i=1, ... .N) are the projections of the spectral image onto the elements of the orthogonal basis, and can be displayed separately as black and white images. These images may reveal features not obvious from a regular black and white image filtered at a certain wavelength.

Spectral bio-imaging systems are potentially useful in all applications in which subtle spectral differences exist between chemical constituents or organization within an image. The measurement can be carried out using virtually any optical system. Examples of existing imaging devices and respective applications that the present invention can be used with today are:

(1) Microscopes of different types including reflection microscopes, transmission microscopes, fluorescence microscopes, upright and inverted microscopes, dark field microscopes, confocal (normal and standing wave confocal) microscopes, reflection contrast microscopes, etc. These configurations may be used for biology research, drug development industry, cell and tissue classification in pathology (clinical and anatomical), hematology, urine analysis for the detection of types of bacteria, gene identification and mapping in chromosomes (interphase and during mitosis), genetic disease diagnosis, cell organelles anatomy and physiology, chromatin distribution and condensation in nuclei, cytoplasm mapping, cell membrane mapping, nuclear membrane mapping, etc.

In particular, these configurations can be built as an automatic equipment or as a tool for a pathologist to decide whether certain cells from a smear of cells, or a tissue section, either stained or unstained, are diseased or healthy, and if diseased, what type and stage the disease is at. For example, these configurations can be used for Pap smear analysis in cervical cancer, blood smear analysis for leukemias of different types, etc.

(2) Camera lens of different types including normal lens, macro lens, zooms, etc., and ophthalmological cameras for imaging of skin, cornea, hair and other external body tissues, in reflection, auto-fluorescence or administered probe fluorescence or drug induced fluorescence. Typical applications for these configurations include (i) mapping of skin cancer; (ii) differentiation between melanoma and nevi (beauty marks); (iii) port wine stains mapping and mapping other skin pigmentation diseases; (iv) in photodynamic therapy (PDT) skin imaging before, during, and after treatment, to optimize the treatment time duration (minimizing side effects); and (v) corneal diseases.

(3) Endoscopes of different types including laparoscopes, cystoscopes including either flexible or rigid fiber optics, and other endoscopes suited for imaging of any internal body tissue surface such as lungs, stomach, intestines, bladder, colon, prostate, cervix, arteries, veins, heart etc., in all modes of detection such as for example reflection of white light, auto-fluorescence, and laser induced fluorescence, both regular and time resolved; both with single and multiple wavelength excitation. Typical applications for these configurations include cancer tissue mapping for diagnosis and analysis tool for the pathologist and surgeon before, during, and after operation, and to visualize very precisely the diseased tissue borders during operation.

(4) Fundus cameras or funduscopes of different types: (i) to map all types of retinal diseases, such as ischemia, caused by diabetes or other health conditions, both as an analysis and early diagnostic tool, and as a therapeutic tool to decide which pail of the retina is affected and when to treat, as an addition or replacement of fluorescein angiography, which is performed today to map diseased vessels and retinal tissues; (ii) as a tool for the ophthalmologist during laser treatment of the retina to indicate the regions and/or the borders of the tissue to be photocoagulated or ablated, or for other treatments.

As described above, there are many experimental methods and specific applications for spectral bio-imaging systems in transmission, reflection, scattering and fluorescence optics. Hence, throughout, it is intended that the radiation, such as light, to be analyzed can come from a wide variety of sources. For example, the source may emit radiation spontaneously or reflect or transmit radiation from a lamp or other illuminated object. In addition, with proper illumination, such as UV or laser, and with proper means of preventing the illuminating wavelengths from reaching the imaging spectrometer, fluorescence or Raman spectral imaging measurements can be performed, in order to obtain different information about the object or objects in question in each case.

FLUORESCENCE MICROSCOPY a. General

The use of multiple dyes [see, Jain (1989) Fundamentals of Digital Image Processing, Prentice-Hall International], is one of the most powerful and common tools for analyzing tissues and cells. Fluorescence microscopy is therefore one of the most important experimental methods used in light microscopy [Lakowicz (1983) Principles of fluorescence spectroscopy, Plenum Press, New York, London]. The power of fluorescent probes is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see, Mason (editor) (1993) Fluorescent and Luminescent Probes for Biological Activity, Biological Techniques Series, edited by Sattelle, Academic Press Limited, London; and, Ploem and Tanke (1987) Introduction to Fluorescence Microscopy, Oxford University Press, Royal Microscopical Society.

The rapid development of new and more sophisticated multicolor fluorescent dye molecules will continue to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

Spectral bio-imaging provides several important advantages for fluorescence imaging applications over simple filter based approaches. These advantages include the following: (1) measurement of the complete spectrum, providing much more quantitative insight into the actual behavior of dye molecules in the sample of interest; (2) ability to overcome many of the traditional problems arising from undesirable background luminescence; (3) undesirable or unpredictable spectral shifts that occur in the emission spectrum of a fluorescent probe, due to its micro-environment (e.g., temperature), can be taken into account in determining the probe concentration, whereas when the fluorescence intensity is only measured with a band-pass filter, such spectral shifts would not only go undetected but might cause significant errors in analyzing the probe concentration; and, (4) simplification of fluorescence image acquisition and, as will be shown below in details, when used in conjunction with the appropriate spectral analysis algorithms it is possible to separate and map, in a single measurement, many spectrally overlapping fluorescent dyes. In fact, by applying sophisticated data analysis algorithms such as multivariate analysis, principal component regression and other classification algorithms [see, Martens and Naes (1989) Multivariate Calibration, John Wiley & Sons, Great Britain] it is possible to analyze many spectrally related parameters simultaneously.

Spectral bio-imaging provides means for eliminating problems associated with undesirable background luminescence. Fluorescence imaging microscopy is typically performed by using a fluorescence filter cube which ensures that the sample is excited by the desired short wavelengths, and that only wavelengths in a limited spectral band corresponding to the fluorescence emission of the probe reach the detector (e.g., eye, camera, etc.) [Mason (editor) (1993) Fluorescent and Luminescent Probes for Biological Activity, Biological Techniques Series, edited by Sattelle, Academic Press Limited, London]. Since fluorescence intensities are usually several orders of magnitude below the intensity of the excitation source, such background luminescence can never be eliminated perfectly [Benson et al. (1985) Cell Biol. 100, pp. 1309–1323]. The three primary sources for undesirable background luminescence are: (1) radiation from the excitation source that is not completely blocked by the dichroic mirror coating and/or the filter; (2) auto-fluorescence of the sample, and sometimes also from the optical elements, can contribute significantly to the background fluorescence. The effects of sample auto-fluorescence can usually be reduced by selecting fluorescent probes whose absorption and emission bands do not overlap with those of the sample being measured. Similarly, by choosing optical elements that are appropriately coated to reduce auto-fluorescence, the effects of this type of auto-fluorescence can also be minimized; and (3) selection of an inappropriate (or sub-optimal) combination of excitation filter, dichroic mirror and barrier filters.

In spite of the best filtering methods available, undesirable background luminescence makes it often difficult, and sometimes impossible, to bring out the relevant fluorescence signal from its background (noise). A spectral bio-imaging system, on the other hand, is able to use spectral differences between (i) the spectral shape and spectral range of the fluorescent dye and (ii) the spectral shape and spectral range of the background luminescence (including autofluorescence), to eliminate the effects of undesirable background luminescence.

Thus, by applying the appropriate spectral image analysis methods to the emission spectra of fluorescent probes, it is possible to improve the signal-to-noise ratio, and hence the accuracy, of fluorescence imaging measurements. This advantage of a spectral bio-imaging approach is of particular importance for ratio imaging, when quantitation of the results is desired. In addition, a spectral bio-imaging system can save time and effort that is otherwise spent in choosing the optimal filters for a filter based measurement.

An example of how spectral imaging can eliminate undesirable background intensities in a fluorescence measurement is shown in FIGS. 5a–b. FIG. 5a shows the fluorescence spectral image of a cell stained with propidium iodide. This image was acquired using the SpectraCube™ spectral bio-imaging system attached to an Olympus inverted microscope (IMT2). The sample was illuminated by a mercury light source and the fluorescence intensity was imaged through a DMG filter cube (DM580 dichroic mirror, D590 excitation filter and BP545 barrier filter). FIG. 5b is a plot of the fluorescence emission spectrum from three individual image pixels. Note that each of the three spectra has two peaks. The peak at 623 nm is due to the actual fluorescence emission spectrum of propidium iodide, while the second peak, at 775 nm, is just a residual of the excitation light that was not completely eliminated by the excitation or barrier filter. This undesirable background radiation could be eliminated by adding another excitation filter (for example Olympus PB460), or an appropriate barrier filter. However, if this same measurement had been made with a (non spectral) imaging system (without the PB460 filter), the intensity measured at each pixel would be proportional to the integral of the spectra shown in FIG. 5b, including the contribution of the undesirable signal in the 775 nm peak. Correction algorithms exist which could be applied to the traditional CCD image, albeit at the expense of noise, to help this situation [Benson et al. (1985) Cell Biol. 100, pp. 1309–1323]. However, with a spectral bio-imaging system which measures the fluorescence intensity at every pixel as a function of wavelength, it is easy to confine the analysis to only those wavelengths which correspond to the emission of the fluorescent dye of interest (i.e., around the 623 mn peak), then avoiding a contribution to the signal by residual spurious sources, as was done in the image shown in FIG. 5a.

The acquisition of multicolor fluorescence images can be greatly simplified when the power of spectral bio-imaging according to the methods of the present invention, is combined with the appropriate fluorescent markers. In order to fully realize the benefits afforded by spectral bio-imaging, the reader is asked to consider the typical steps involved in using a filter based imaging method to measure the fluorescence from a sample containing multiple probes. First, probes with sufficiently different absorption and emission spectra must be selected. Intodays practice, this requirement limits the number of fluorescent markers in a specimen to between three and five probes. Fluorescence images are then acquired, one image for each dye, by appropriately rotating two filter wheels, one for selecting the excitation wavelength and another for capturing the emission spectrum, or alternatively, rotating one filter wheel aimed at selecting the excitation wavelength, while capturing the emission spectrum by a triple dichroic filter. Approaches in which tunable filters (no moving pails) are used to control the excitation and/or emission wavelength have also been proposed. Recently, multispectral interference filters have also been used to enable imaging multiple fluorophores [Lengauer et al. (1993) Human Molecular Genetics 2, pp. 505–512]. Means of changing the dichroic mirror (e.g., by changing filter cubes) is also required. It is also frequently necessary to readjust the focus of the image at each wavelength and sometimes even the CCD camera exposure time must be changed to achieve higher signal-to-noise ratios. The resulting monochrome images, each corresponding to the emission of a different fluorescent dye, are then pseudo-colored and superimposed (using a digital computer with readily available off-the-shelf software). The resulting image shows the location of several fluorescent markers, each with a different pseudo-color. Since slight changes in the position of the dichroic mirror will cause translational shifts in the digitized images, it is necessary to use multiple wavelength dichroic mirrors [for use of a dichroic with quadruple wavelength band-pass properties see, Hiraoka et al. (1992) Seminars in Cell Biology, Vol. 2, pp. 153–164] or to register the images prior to their superposition. The image registration approach is more common, despite the fact that image registration is a difficult problem which can be time consuming and often produces only marginally satisfactory results. These are technical challenges which must also be addressed when acquiring multi-color fluorescence images [ Waggoner et al. (1989) Part B of Methods in Cell Biology, Vol. 30, Ch. 17, pp. 449–478, edited by Taylor and Wang, Academic Press Inc.].

The spectral bio-imaging methods of the present invention thus overcome one of the fundamental limitations imposed by filter based approaches to fluorescence imaging. By enabling the simultaneous measurement of the emission spectrum of an unlimited number of fluorescent dyes (including dyes whose emission spectra overlap to a great extent, as demonstrated hereinbelow in the Examples section for the Texas-Red and Rhodamine fluorophores), spectral bio-imaging eliminates the need for sequentially acquiring images of the emissions of multiple fluorescent probes. The advantage of using a spectral bio-imaging system is greatest when the used fluorescent probes can be excited by a common excitation source. In this case, a single spectral image acquisition can capture the fluorescence emission of an almost unlimited number of dyes and the need to (1) select non-overlapping dyes; (2) change filter cubes; (3) change excitation or emission filters; (4) optimize the focus and/or exposure time or register the images, is eliminated. The challenge, of course, is to select suitable dyes that can be excited with a common source. Dyes which are excited by fluorescence energy that is transferred to/from one another are thus ideally suited for multi-color fluorescence imaging using a spectral bio-imaging system. Clearly, the use of dyes with similar emission properties will make visual detection (e.g., under the microscope) more difficult; however, this limitation is likely to be solved using the spectral bio-imaging methods of the present invention.

b. Spectral identification of multiple fluorophores

The use of spectral bio-imaging methods according to the present invention enables the simultaneous measurement of many dyes (i.e., fluorophores, fluorescent moieties) in one measurement. There is no restriction on the type of dye, even dyes that overlap spectrally (e.g., Rhodamine and Texas-Red) can be identified as will be exemplified below (see, Example 5) by applying suitable algorithms (e.g., linear combination for background subtraction, etc.) and their occurrence mapped in an image. If many dyes are to be used simultaneously, careful consideration should be given to their excitation wavelength, fluorescence intensity and emission spectrum. When this is done properly, the results can be analyzed quantitatively as well. For example, the relative concentration of several proteins can be mapped in a single measurement using suitable fluorescently tagged antibodies which specifically bind to these proteins. By using standard calibrated dyes, the absolute concentrations can also be determined. One important example where the detection of multiple fluorescent probes can be a significant advantage is FISH (fluorescent in situ hybridization) [Emanuel (1993) Growth Genetics and Hormones 9, pp. 6–12], which is used to analyze genes at the chromosomal level, and find possible genetic defects such as gene amplification, deletion, translocation, rearrangement, etc.

Certain diseases and disorders, including many cancers and birth defects, are genetic disorders caused by defects in one or more genes. Many other diseases are known or believed to have a genetic component(s), that is, there exists genetic defect(s) that does not alone cause the disease but contributes to it, or increases the probability of developing the disease later in life, phenomena known in the art as multifactorial diseases and genetic predispositions. Correlation of visible genetic defects with known diseases would allow doctors to make definitive diagnoses, and permit early detection and treatment of many diseases. Genetic counseling could alert prospective parents and at-risk individuals to the possibility of potentially serious medical problems in the future, permitting appropriate intervention.

More than 5,000 genetic disorders have now been identified, many of which are associated with multiple genetic defects. After the discovery that chromosomes are the carriers of hereditary information, scientists reasoned that it should be possible to document visible defects in chromosomes that were responsible for specific disorders. In the 1960's, staining techniques were developed for microscopy-based classification of mitotic chromosomes spread onto glass slides. For several decades, visual analysis of chromosomes banding patterns has been used to correlate human genetic disorders with observed structural abnormalities in mitotic chromosomes. Chromosomes are typically examined by brightfield microscopy after Giemsa staining (G-banding), or examined by fluorescence microscopy after fluorescence staining, to reveal characteristic light and dark bands along their length. Careful comparison of a patient's banding pattern with those of normal chromosomes can reveal abnormalities such as translocations (exchange of genetic material between or within chromosomes), deletions (missing chromosomes or pieces of chromosomes), additions, inversions and other defects that cause deformities and genetic diseases.

However, many serious genetic diseases, such as for example cystic fibrosis (CF) and many others, are caused by mutations that involve addition, deletion or substitution of only one or a few nucleotides. Such small defects are not detectable by the chromosome banding techniques described above, and for many years cytogeneticists have been working to develop techniques for locating and quantifying minute defects.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes. The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (1) FISH can be used not only on isolated chromosomes and nuclei, but also whole cells within fixed, paraffin-embedded tissue sections; (2) it can detect relatively small defects (ability of detecting smaller defects being constantly increased); (3) it can provide results relatively quickly; (4) its moderate cost allows it to be used in most diagnostic and research laboratories; (5) adaptation can be developed for various probes and specimen types; and, (6) high specificity and sensitivity can be achieved (7) within a short throughput, typically two hours.

Many FISH applications require only that the cytogeneticist look through the eyepieces of a microscope, or at the image on the monitor, to determine whether a fluorescent label is present or absent. With somewhat more complex specimens, a simple count of one or two colored labels may be done. However, the ability to process digital images and extract numerical data from them adds a vast new set of capabilities to FISH techniques. An appropriate imaging method, such as the method of the present invention, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene. Emerging techniques such as multicolor FISH employ color image analysis to detect and quantify multiple (3,4,5 and more) fluorescent probes.

As discussed above, FISH can provide information on the location of the labeled probe, the number of labeled sites on each chromosome, and the intensity of labeling (the amount of genetic material) at each site. Centromeric (repetitive DNA) probes are used to tag and count the number of copies present of each targeted chromosomes. Locus-specific probes are used to map the location of small regions of genetic material. Both types of probes can be used on intact interphase nuclei as well as mitotic chromosome spreads, and can be counted visually. They are routinely used to identify genetic diseases characterized by having too many or too few copies of a specific chromosome, chromosome fragment, or gene. In very early stages of some cancers, long before the cells are recognizably abnormal, there may be an increase in the number of specific genes, phenomenon known in the art as gene amplification, that are detectable using locus-specific probes. Using FISH to detect chromosomal abnormalities in cancerous cells may point out the developmental stage the disease have reached and therefore to select the most suitable treatment(s), many of which are stage specific in their effectiveness. Thereby precious time is saved and patient's suffering is minimized, selecting the most effective stage specific treatment.

It is possible to uniformly label the entire surface of one specific chromosome by isolating the chromosome (using flow cytometry, for example), physically (e.g., by sonication) or enzymatically (e.g., by endonucleases) chopping it up, and generating a set of probes against all of the pieces. Whole chromosome probes, also known as chromosome paints, will fluorescently label all copies of the target chromosome. One important application of chromosome painting is the detection of deletions and translocations between two chromosomes, as characteristically occurs in early stages of certain cancers.

For example, if chromosome A is specifically labeled with a green paint and chromosome B is labeled with a red paint, any translocation of material from A to B will appear as a green area on a red chromosome (and vice versa). Typically, chromosome paints generated from normal chromosomes are used to detect deletions or translocations on abnormal (patient) chromosomes. Reverse chromosome painting uses probes generated from an abnormal chromosome to identify DNA from various normal chromosomes which contributed material to the abnormal chromosome.

Comparative genomic hybridization (CGH) is a variation of reverse chromosome painting in which two cocktails of DNA probes are generated from entire sets of chromosomes. One cocktail is generated from a set of normal chromosomes, and another from a set of abnormal (e.g., tumor) chromosomes. The two sets of probes are generated using different reporter molecules so that, for example, normal DNA will exhibit red fluorescence, and abnormal DNA will exhibit green fluorescence. A normal metaphase spread is hybridized simultaneously with both cocktails, and evaluated using color image analysis. Regions of normal chromosomes that fluorescence more intensely green than red indicate that DNA amplification (multiple gene copies) has occurred at that gene in the patient's abnormal cells. Regions with more red than green fluorescence (decreased green/red ratio) indicate sites of genetic deletions in the patient's chromosomes, and regions with equal green and red fluorescence indicate that no DNA changes have occurred at that site. CGH and related techniques are more complex than previous labeling techniques, yet they offer the ability to detect and quantify more subtle and extensive genetic alterations than were previously possible.

From what has been said above, it follows that karyotyping, translocation/rearrangement detection, chromosome deletion/amplification, and gene mapping will greatly benefit by the use of the sensitive, quantitative, spectral imaging methods of the present invention that builds a whole spectral image at relatively high spectral resolution, instead of a simple color fluorescence image. This is because such methods will decrease the sample preparation time and will be able to distinguish between a hybridized fluorescent probe from one that is residual in the background (by small spectral shifts), and will be able to measure a very large number of probes simultaneously.

Thus one of the objectives of the present invention is to provide a FISH imaging method designed to exploit the advances in probe technology. According to the present invention there is a possibility of greatly increasing the number of probes that can be analyzed in any given chromosome analysis, as well as dramatically increasing the speed and degree of automatization at which this information can be acquired as compared with prior art methods.

The FISH imaging methods of the present invention exploit the advantages of the SpectraCube™ system, that is capable of simultaneously acquire fluorescence spectra from all pixels of the microscope field of view and detect the location of many probes in a single experiment. In conjunction with the availability of chromosome specific probes and novel labeling strategies, the methods being capable of creating a FISH karyotype with each chromosome being painted with a different color (i.e., 24 different colors for a human karyotype). These methods result in extremely high sample throughput and allow analysis of essentially unlimited number of probes.

As delineated above, one of the key concepts of the present invention is the use of many fluorescent probes in FISH assays. Numerous methods are available to label DNA probes for use in FISH, including indirect methods whereby a hapten such as biotin or digoxigenin is incorporated into DNA using enzymatic reactions. Following hybridization to a mitotic chromosome spread or interphase nuclei, a fluorescent label is attached to the hybrid through the use of immunological methods. More recently, fluorescent dyes have been directly incorporated into probes and detected without the use of an intermediate step. Standard FISH dyes include fluorescein, rhodamine, Texas-Red and cascade blue, and multiprobe FISH analysis can be accomplished by labeling different probes with different haptens or fluorescent dyes.

Fluorescence is a form of luminescence which occurs after photons of light are absorbed by a molecule known as a fluorophore at the ground electronic state. The molecule is raised to an excited state as a result of electron transfer to a higher energy orbit. This excess energy is dissipated when the electron returns to the original ground state, releasing a quantum of light. The fluorescence light is of longer wavelength than the absorbed light. This shift is limited, causing the emission to be close to the excitation wavelength. Because of this, the fluorophores which can be excited in one spectral range emit in a similar spectral range. For example if the excitation is in the blue range the emission is expected in the green. So if one wants to use many different probes which emit different spectra it is evident that they must be close in wavelength, and also often overlap; as a consequence, spectral resolution is of critical importance to be able to discriminate between the different probes.

According to the methods of the present invention, individual probes are assigned a pseudocolor and the information is displayed on a computer screen. The use of multicolor fluorescence opens up a possibility of extending FISH into important clinical applications which may benefit from multiple probes. Examples include aneuploidy and chromosome structural studies, detection of marker chromosomes and complete FISH karyotypes. Since multiple information may be gained from a single hybridization, throughput is increased and internal standards may be used in order to assess gene dosage effects or to determine the extent of deletions.

The methods of the present invention, utilizes detection of fluorescence excited by a white or coherent monochromatic light source in few narrow spectral bands and a sensor with cooled CCD. Thus, multiple spectra, each representing a different DNA probe, may be simultaneously measured. This, in turn, increases the speed and accuracy of image acquisition, compared to conventional approaches which take multiple snapshots of chromosomes and then reconstruct the image, a process which is time consuming and generates artifactual results. Hence, the present invention represents a significant progress over the state-of-the-art cytogenetic imaging, because it allows more sensitive, rapid and accurate detection of multiple probes.

C. Detecting micro-environmental changes

The use of fluorescent dyes (e.g., when attached to an antibody) is not limited to identifying the existence of certain chemical compounds (e.g., proteins). Some dyes can also be used to probe actual chemical and physical parameters. For example, a dye whose spectrum changes when it gains or loses a hydrogen atom can serve as a pH indicator. Dyes exhibiting spectral changes due to the local electrical potential, pH level, and intracellular ions concentration (e.g., sodium, magnesium, zinc, free calcium, etc.) are currently used in a variety of applications. For example, see, Tsien (1994) Chemical and Engineering news 34, pp. 34–44.

The use of environmentally sensitive dyes is closely related to ratio imaging, a common analysis method [Bright et al. (1987) BioTechniques 5, pp. 556–563]. For some of the dyes that are in use today, environmentally related spectral changes occur in only part of the spectral range. By measuring the ratio of fluorescence emission in two spectral ranges, one can thus study environmental effects, independent of sample thickness, illumination nonuniformity, etc.

The ability of the spectral bio-imaging methods of the present invention to measure the complete spectrum, rather than using current techniques to measure the fluorescence at two (or three) discrete wavelengths, has several advantages for ratio imaging applications. Measurement of the complete spectrum significantly improves the accuracy and sensitivity of ratio imaging. For example, one can use the complete spectrum to measure the ratio of two integrated intensities in two different spectral ranges, and at the same time eliminate all the background intensity by integrating only over the relevant spectral range. It is also possible to use more sophisticated algorithms for analyzing the spectral data, such as determining the environmental parameters of interest by fitting the measured spectral data to reference spectra stored in a library. Because spectral analysis is performed at every point in the image, a full morphological analysis of the sample is possible (as described for example in U.S. Pat. No. 4,965,725 to Rutenberg). Spectral bio-imaging thus provides the capability to map (i.e., display as an image) physical and chemical parameters of interest; potentially enabling more innovative and effective research.

By using spectral bio-imaging techniques, it may be possible to use environmentally sensitive dyes which do not lend themselves to analysis using other ratio methods. The detection of dyes sensitive to several environmental parameters (e.g., voltage and pH) could also be achieved by using appropriate analysis algorithms.

An example of a method using the SpectraCube™ system to detect the fluorescence emission of micro-environmentally sensitive dyes is shown in FIGS. 6a–d. FIG. 6a shows an RGB pseudo-color image of a cell during mitosis, the mitotic cell has been stained with acridine orange. Acridine orange is a dye whose fluorescence emission changes with the form of the dye. In the monomeric form, in which the dye molecules are highly diluted in solutions (i.e., low concentrations) the fluorescence maximum is around 530 nm. The dimeric (and polymeric) fluorescence, on the other hand, which is typical for concentrated solutions peaks at 640 nm [see, chapter 6 in W. T. Mason (editor) (1993) Fluorescent and Luminescent Probes for Biological Activity, Biological Techniques Series, edited by Sattelle, Academic Press Limited, London]. FIG. 6b is a plot of two spectra selected from the thousands of spectra measured in the spectral image of FIG. 6a. Spectrum M was selected from a cytoplasmic region in which acridine orange is monomeric, whereas, spectrum D was selected from a nuclear region in which acridine orange is dimeric. The two spectra correspond to the fluorescence emission of a point on a chromosome (spectrum D) and a point on the cytoplasm (spectrum M) of the cell. The acridine orange dye exhibits a spectral shift as a result of energy transfer between the molecules of acridine orange and the surrounding chemical environment. FIGS. 6c and 6d show the results of two similarity mapping analysis (see above) that were performed, using the spectra of the monomeric form (M) and dimeric form (D) of acridine orange, respectively, as reference spectra. This algorithm facilitates the quantitative distinction between different forms of the dye molecules thereby enabling additional insights about the structure and environment of the cell. FIG. 6c show the results of a similarity mapping analysis using spectrum D of FIG. 6b as a reference spectrum. This analysis revealed the accumulation of the dimeric form of acridine orange in the poles of the mitotic cell examined, where the majority of is nucleic acids are concentrated. FIG. 6d shows the results of a similarity mapping analysis using spectrum M of FIG. 6b as a reference spectrum and reveals the remaining cytoplasm of the cell. The images shown in FIGS. 6c–d thus highlights spectral differences due to the fluorescence of the monomeric form of acridine orange (in the cytoplasm) and the dimeric form (at the chromosomes). Thus, the methods of the present invention are highly suitable to reveal fluorescence shifts induced by cellular constituents (i.e., administered probe induced fluorescence).

d. Measurement of auto-fluorescence from natural pigments

Chlorophyll is a natural pigment exhibiting auto- (i.e., natural) fluorescence [Haliwell (1981) Chloroplast metabolism—the structure and function of chloroplast in green leaf cells, Clarendon, Oxford, U.K.]. The fluorescence spectrum of chlorophyll has been studied extensively, in part because it is more complicated than the spectrum from a typical fluorescent dye [Parson (1988) Photosynthesis and other reactions involving light, Biochemistry (Ed. Zubay) 2nd edition, pp. 564–597, Macmillan New York], and also because chlorophyll auto-fluorescence is important for many applications. For example, the measurement of chlorophyll auto-fluorescence can be used to probe cell metabolism and to track photosynthesis. Auto-fluorescence occurs also for porphyrins, native cytoplasmic proteins and other compounds. The ability of a spectral bio-imaging system to measure spectral differences in different parts of a cell provides important insights into the functions of the cell organelles in a living cell. An example of a chlorophyll spectral imaging is shown in FIGS. 7a–d. The algae Oedogonium sp. was examined by fluorescence microscopy. Excitation was in the green spectral range (540 nm), and the emission in the red spectral band was measured by the SpectraCube™ system. FIG. 7a reveals the total emitted fluorescence from the specimen. Both the red chlorophyll fluorescence (on the right) and the relevant green excitation light from cell debris in the specimen (on the left) can be clearly seen. The individual algae cell exhibiting red fluorescence are only partially visible. The fluorescence spectra from four different pixels of the specimen are shown in FIG. 7e. Spectrum A, with an emission peak at 685 nm, was measured from a point in the central algae in which the red fluorescence dominates. Spectrum B, on the other hand, corresponds to point of cell debris exhibiting green emission, with a peak at 542 mn. Spectra C and D correspond to two additional pixels on the algae. As shown in FIG. 7b, by using spectrum A as reference spectrum for a similarity mapping analysis it was possible to precisely locate, and determine the relative concentration of chlorophyll in the algae, including portions of the algae obscured by debris. This pseudo-colored FIG. shows that the chlorophyll, although dispersed, is located in the center of the cell. FIG. 7c is the result of a similarity mapping analysis using as a reference spectrum a point in the image in which the red fluorescence is faint. These results demonstrate the existence of different chlorophyll intensities at different cellular sites, for example, some of the fluorescence occurs at the periphery of the cell membrane. Thus, by using the similarity mapping algorithm, it was possible to visualize the characteristics fluorescence emitted from specific subcellular regions in the cell. FIG. 7d highlights the spongy structure of the cell debris when a similarity mapping analysis using the green spectrum from the cell debris as a reference spectrum (spectrum B in FIG. 7e) was applied. This last analysis also revealed the algae cell wall, which reflects a green emitted light. In addition, this similarity showed the location of unicellular algae.

The study of auto-fluorescence has many other important applications. For example, studies of natural skin fluorescence have identified 'spectral fingerprints' corresponding to different tissue constituents and histological organization of the tissue. The use of tissue spectral fingerprints to identify normal from abnormal tissue has been studied extensively. See, for example, Marchesini et al. (1991) Photochemistry and Photobiology 53, pp. 77–84; Bottiroli et al. (1994) Lasers in Surgery and Medicine; and, Profio (1984) IEEE Journal of Quantum Electronics QE-20 pp. 1502–1506. The potential clinical utility of spectral bio-imaging in such medical diagnostics applications appears to be significant.

e. Fluorescence Resonance Energy transfer (FRET)

FRET is a fluorescence method which enables the determination of the spatial separation between two fluorophores. In FRET, two different fluorophores, designated as 'donor' and 'acceptor' are used. This pair of fluorophores is chosen carefully so that when the donor is excited, it can either fluoresce or transfer the energy being absorbed by it to the second fluorophore (the acceptor), causing it to fluoresce. Thus, it is possible to distinguish the donor from the acceptor because of differences in the emission spectrum.

The physical separation between the donor and acceptor is determined from the fact that the efficiency of the energy transfer strongly depends on the distance between the two fluorophores (typically, the efficiency is proportional to the inverse of the sixth power of the separation distance). When these two fluorophores are attached to two different types of molecules, or to the same molecule in two different states, measuring FRET using a spectral bio-imaging system (attached to a microscope) greatly facilitates the ability to distinguish between different molecules (or molecular states) while simultaneously measuring their spatial distribution. A detailed discussion of energy transfer phenomena in microscopy can be found in the arts literature [see, Herman (1989) Fluorescence Microscopy of Living Cells in Culture, part B, Chapter 8, pp. 219–243, edited by Taylor and Wang, Academic Press Inc.; and, Jovin and Arndt-Jovin (1989) Cell structure and function by microspectrofluorometry, Chapter 5, Academic Press Inc.].

FRET is performed by measuring three parameters: (i) the intensity at the donor emission peak when exciting at the donor absorption peak; (ii) the intensity at the acceptor emission peak when exciting at the donor absorption peak; and (iii) the intensity at the acceptor emission peak when exciting at the acceptor absorption peak. These three parameters are then corrected and analyzed to give the separation distances and location of the two fluorophores being studied.

Using a spectral bio-imaging system in particular the SpectraCube ™ system, not only improves the measurement results, but also simplifies the measurement. In fact, by using a spectral bio-imaging approach, only two measurements are required since both the donor and acceptor emission bands can be measured simultaneously when excitation is in the donor absorption band.

Using spectral bio-imaging, the FRET method might be further developed. For example, one might select for FRET an acceptor fluorophore which is sensitive to changes in the environment, and at the same time that molecular distances are measured, use ratio imaging methods to monitor microenvironmental changes. In a further example, FRET can be used with two different acceptors, (with different emission spectra) providing information about two separation distances and fluorophore locations simultaneously. Dual acceptor experiments are very hard to perform with traditional methods. The use of spectral bio-imaging can improve the accuracy of the FRET results, simplify the experimental procedure and enable more powerful analysis methods.

TRANSMISSION MICROSCOPY

Light microscopy is one of the most fundamental techniques for the visualization of cells and tissues in biology and pathology. Transmission microscopy suffers greatly from the inherently low contrast of cell organelles and structural details. Many methods have been developed to improve this contrast, among them staining and spatial filtering. The use of spectral bio-imaging methods of the present invention is one of the most straightforward methods to increase the apparent contrast of cells and tissues examined under a transmission microscope, thereby improving dramatically the identification and discrimination capabilities of this popular microscopic method. The basic approach proposed here is to measure a spectral image, and to then use this large amount of information in conjunction with spectral and morphological analysis methods and algorithms in order to identify and map cellular and subcellular details.

In order to facilitate the histological examination of biological specimens, a variety of staining techniques were developed during the last century using organic stains which specifically bind to different macromolecules in the cells, though the molecular basis of the staining techniques has been and still is empirical. Other image contrast enhancement methods include the use of spatial filtering techniques such as dark field and polarization methods [see, Kam (1987) Quarterly Reviews of Biophysics, 20, pp. 201–259]. The most common staining techniques are the Romanowsky-Giemsa stain, and Haematoxylin-Eosin. The Romanowsky-Giemsa staining procedure uses a combination of two dyes, one of which is Azure-B (trimethyl methionine), a thiazin dye, and the second being Eosin Y (hydroxyxanthene bromide). The thiazines are cationic dyes and therefore bind to acidic cellular constituents, whereas Eosin is an anionic dye and tends to bind to basic cellular constituents. It is widely accepted that the use of these two components creates the so-called Romanowsky-Giemsa effect, which is expressed as the development of a specific purple color, a new dye complex, in some stained sites. The molecular basis of the azure-B-Eosin complex is obscure. Some authors think that azure-B binds to anionic structures such as the phosphate groups of DNA, and that Eosin simultaneously binds both with an adjacent cationic site on the DNA and with the azure-B. In a more recently proposed model of the azure-B-Eosin complex, Friedrich and colleagues [Friedrich et al. (1990) Histochemistry 93, pp. 247–256] have suggested that azure-B first binds to phosphodiester residues of the DNA molecule. The authors have hypothesized that the phenyl group of the Eosin molecule is the portion that binds to the azure-B molecule (which lies in a single plane). The color purple is a result of a red shift of the Eosin absorption peak, which in turn is caused by the dielectric polarization of bound Eosin. The very existence of such an azure-B-Eosin complex is still questioned by others

[see, Friedrich et al. (1990) Histochemistry 93, pp.247–256; Bottiroli et al. (1994) Lasers in Surgery and Medicine; Profio (1984) IEEE Journal of Quantum Electronics QE-20 pp. 1502–1506; Herman (1989) Fluorescence Microscopy of Living Cells in Culture, part B, Chapter 8, pp.219–243, edited by Taylor and Wang, Academic Press Inc.; and, Jovin and Arndt-Jovin (1989) Cell structure and function by microspectrofluorometry, Chapter 5, Academic Press Inc.]. Whatever the technique, with staining it is possible to distinguish between subcellular compartments of the cell, and especially to distinguish the chromatin organization in the nucleus. It is well established that the ratio between heterochromatin, stained dark blue, and euchromatin, stained pink, is one of the major determinants in the evaluation of cells in tissue sections. Nevertheless, the results obtained from stained specimens remain, to some degree, a matter of experience, art, and subjective interpretation. In order to diminish the effect of the scientist's experience, there have been attempts to study the spectroscopic characteristics of the interaction between organic stains and macromolecules, and thus to evaluate the so-called Romanowsky-Giemsa Effect of DNA staining.

Spectral imaging applied to transmission light microscopy can greatly improve the quantitative measurement of size, shape and textural features of cells and tissues. This technique is known as morphometry, which is a rapidly growing field in biology and pathology [Erler et al. (1993) Modern Pathology, 6, pp. 612–618]. Morphometric spectral image analysis enables the evaluation of subtle cytological and histological features to yield useful ultrastructural and medical information for diagnostic and prognostic evaluation [Hytiroglou et al. (1992) Cancer 69, pp. 88–2121]. The ability to measure, quantitatively, the ratio of heterochromatin to eucluomatin in stained tissue, as well as identifying different cell organelles by using spectral bio-imaging according to the methods of the present invention is demonstrated hereinbelow and in Example 2.

The advantage of spectral bio-imaging for cell biology is in the ability of this technique to determine, point by point, spectroscopic information in a given stained cell. Each pixel of the cell image provides accurate information on the transmitted light, at the given point, and this is immediately calculated into the absorption spectrum. FIG. 8a shows a plasma blood cell stained by the method of May-Grunwald-Giemsa for blood cells. FIG. 8b shows different subcellular sites of the cell, and the pixels from which four spectra were collected which are pointed out by arrows. Pixel A points to heterochromatin; pixel B points to a light blue stained area of the cytosol; pixel C points to euchromatin; pixel D to a cytoplasmic vesicle; and, pixel E to a point in the cytosol. These spectra (A through E) are five out of ten thousand that exist in this spectral image. FIG. 9a shows the transmitted light spectra from these five pixels of the cell image. These spectra are uncorrected with respect to the incident illuminating light source. One can see that the transmitted light from euchromatin and heterochromatin are of low intensity, and show some spectral differences (compare spectra A and C in FIG. 9a). On the other hand, the point spectra taken from the cytosol (B) show specific spectral changes, especially light intensity differences. FIG. 9b shows the absorbance of the corresponding spectra which were calculated relative to the incident light recorded outside of the cell. It can be seen that each subcellular compartment (A through E) in the stained cell has spectral characteristics which are responsible for the range of colors seen by ones eyes in the image. Nevertheless, the eye is limited in its ability to demarcate and separate the different color-macromolecule complexes on the basis of their colors. The SpectraCube™ based system combined with the methods of the present invention allows for the comparison of a chosen spectrum from the image with the other ten thousand different spectra composing the entire image. Thus, each point in the image is characterized by a certain level of similarity to the chosen (i.e., reference) spectra. The mathematical algorithm called similarity mapping described above creates a gray level image from the original spectral image. In principle, by using this algorithm (and many other similar algorithms can be examined), one can locate all those pixels in the image which have similar characteristics to the chosen reference pixel. This technique enhances the eye's ability to differentiate between fine details in the stained cell. Such an image may be defined as a quantitative result which relates to a particular image.

FIGS. 10a–d show four different quantitative similarity mapping images reconstructed by using the spectra of FIG. 8a. FIG. 10a shows a similarity map reconstructed by mapping with spectrum A of FIG. 9a, as a reference spectrum. The fine structure of euchromatin areas in the nucleus is markedly enhanced. One can detect a euchromatin network tightly connected all over the nucleus, and even on the upper side of the nuclear envelope. In the center of the nucleus there is a particularly bright site, which may represent the nucleolus, and this conjecture is supported by the similarity map shown in FIG. 10c. FIG. 10b shows a similarity map built up with the reference spectrum B of FIG. 9a. Two main features may be noted in this Figure, both connected to membranous borders, the one in the center of the cell, and the other demarcating the outer cell membrane. The newly formed image may support the idea that the central bright array in the cytosol is a large Golgi complex, and this interpretation is supported by the similarity map in FIG. 10d, demonstrating peripheral vacuoles surrounding the Golgi area. The nuclear heterochromatin is shown in FIG. 10c, after mapping with the reference spectrum C of FIG. 9a. The image is complementary to that shown in FIG. 10a, but on the other hand, shows some unexpected connections between the different complexes of the nuclear heterochromatin. Finally, FIG. 10d, achieved by the mapping of the combined spectra of D and E of FIG. 9a, reveals vesicular structures in the cytosol, basically cytoplasmic vacuoles. Surprisingly, this similarity map demarcates the nuclear envelope, which is another membrane surrounding a subcellular compartment.

On the basis of these spectral imaging results of May-Grunwald-Giemsa stained cells, it is obvious that each point (or what is defined as a pixel) has its specific absorbance and transmittance spectra which can be classified into several categories. At this stage of research, there are some indications for a spectral component which may correlate well with what is called "the purple Romanowsky-Giemsa complex". The absorbance spectra of heterochromatin (FIG. 10c) shows clearly an outstanding absorbance peak at 540 nm which is in good accordance with what was described as the "purple Romanowsky-Giemsa complex" [see, Friedrich et al. (1990) Histochemistry 93, pp. 247–256; Bottiroli et al. (1994) Lasers in Surgery and Medicine; Profio (1984) IEEE Journal of Quantum Electronics QE-20 pp. 1502–1506; Herman (1989) Fluorescence Microscopy of Living Cells in Culture, part B, Chapter 8, pp. 219–243, edited by Taylor and Wang, Academic Press Inc. (1989); and, Jovin and Arndt-Jovin (1989) Cell structure and function by microspectrofluorometry, Chapter 5, Academic Press Inc.]. The spectral cytoplasmic features (spectrum B of FIG. 9a), when used for similarity mapping, allow the clear demarcation of components which one believe represent the nuclear envelope, Golgi cisternae, cytoplasmic vacuoles, and the outer cell membrane. Nevertheless, stained cells, dried in the air, may show a superposition of cytoplasmic layers which apparently reduce resolution. For the future development of spectral imaging, the use of aldehyde-fixed cells which will enable to focus on specific depths of the cell and thus to markedly enhance the possibilities of this technique, is suggested.

In some cases, spectral images acquired using transmission methods and unstained tissue may provide useful information, similar to that found in fluorescence microscopy techniques. One of the advantages of combining spectral bio-imaging and transmission microscopy is the ability to use a 'clean' measurement technique, i.e., no need for working with potentially toxic dyes or fixation agents.

Thus, according to the present invention there is provided a spectral bio-imaging method characterized by high spatial and high spectral resolutions, the method includes the steps of (a) preparing a sample to be spectrally imaged; (b) viewing the sample through an optical device, the optical device being optically connected to an imaging spectrometer, the optical device and the imaging spectrometer being for obtaining a spectrum of each pixel of the sample by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating one or more of the elements of the interferometer system, so that the optical path difference between the two coherent beams generated by the interferometer system is scanned simultaneously for all the pixels of the sample; and (v) recording signals of each of the detector elements as function of time using a recording device to form a first spectral cube of data; and (c) interpreting the first spectral cube of data using a mathematical algorithm. The method may further include the step of (d) displaying a map of the interpreted spectral cube of data. The optical device may be any one, but not limited to the ones mentioned herein above. The collimated light may be light transmitted through the sample, light reflected from the sample, light scattered from the sample or light emitted from the sample. The light emitted from the sample may be of administered probe fluorescence, administered probe induced fluorescence or auto-fluorescence. The light may originate from any source and may be of any type, for example, laser, white light, filtered light, ultraviolet light and/or a light having a small wavelength range. The light may originate from a multiplicity of light sources, the sources may operate simultaneously or successively. The two-dimensional array may be a video rate CCD, a cooled high dynamic range CCD, an intensified CCD or a time gated intensified CCD. The sample may be any biological sample such as a cell, a tissue or a whole organism, all may be from any species including a human. The cell may be of any type including a cell collected by a Pap smear, a blood cell, a fetal cell, a cell suspected of being malignant, a cell during interphase, a cell during mitosis or a cell during meiosis. The tissue may be of any type including eye retina, a retinal blood vessel, a tumor, skin, cornea, hair, lungs, stomach, intestines, bladder, colon, prostate, cervix, arteries, veins or heart.

Further according to the present invention the sample may be a cell, a tissue section or an organism; the light is induced by a probe, the probe binds to a specific cellular constituent, the method is for detecting the presence or the level of the cellular constituent. The probe may include a conjugated fluorescent moiety and the induction is a fluorescence light emission of the fluorescent moiety. The probe may further include a nucleic acid molecule such as deoxyribonucleic acid and/or ribonucleic acid, the method is for detecting the presence or the level of a cellular nucleic acid hybridizing with the nucleic acid molecule. The probe alternatively may include an antibody, the method is for detecting the presence or the level of a cellular protein recognized by the antibody. The fluorescent moiety may be any fluorescent moiety used for biological applications, yet, as is understood to one ordinarily skilled in the art, the fluorescent moiety may further be any fluorescent moiety yet to be discovered suitable for biological applications.

The mathematical algorithm may be selected from the algorithms described hereinabove, may be any combination of the algorithms described above and, as is clear to one ordinarily skilled in the art, the mathematical algorithm may be any presently known or yet to be developed, which algorithm is suitable for analyzing and/or displaying spectral images.

The methods of the present invention may be used for spectral identification of multiple fluorophores administered to the sample; detecting micro-environmental changes such as but not limited to local electrical potentials, pH levels and intracellular ion (e.g., ionic forms of hydrogen, sodium, magnesium, zinc and calcium) concentrations in the sample; measuring auto-fluorescence from a natural constituent such as chlorophyll, porphyrins and/or cytoplasmic proteins in the sample; for measuring fluorescence resonance energy transfer to determine spatial separation between at least two fluorophores in the sample; for identifying and mapping cellular and subcellular details such as but not limited to types of chromatin organization in the nucleus of a cell in the sample; for monitoring life processes in the sample as function of time; for fluorescent in situ hybridization including fluorescent in situ chromosome painting; and for cell classification.

Reference in now made to the following examples, which together with the above descriptions, illustrate the invention.

EXAMPLE 1

SPECTRAL IMAGE ANALYSIS OF THE DIGESTIVE CYCLE OF PARAMECIA FED WITH ALGAE, USING A SIMILARITY MAPPING ALGORITHM

This example demonstrates how spectral imaging reveals life processes in cells, performed by measuring several spectral cubes at different times in the life cycle of a cell, and by similarity mapping highlighting the position in the cell of a specific chemical or organelle, for each examined time.

This then reveals movement or chemical changes, energy exchanges, or metabolic reactions between the organelles of the cell as function of time. The reason why the present invention is ideally suited for the study of life processes is because by measuring spectra at high resolution and sensitivity, it can easily follow small chemical changes characterizing cells and tissues, which changes being related to life processes themselves.

FIGS. 11a–d show two spectra of chlorophyll in *Paramecium vulgaris* of four individual cellular locations (i.e., pixels). Living Paramecium were analyzed using the SpectraCube™ system attached to a fluorescence microscope (Olympus BH2 RFC). The Paramecium cells were excited by a green light source (band pass maximum 545 nm), and the red fluorescence was measured by the system. Spectra 1 and 2 show a very slight difference in their fluorescence peaks at 630 nm and 695 nm. The relative intensities of these two peaks change as a function of localization within the cell, as shown in spectra 3-6.

The crude chlorophyll auto-fluorescence image of the algae ingested by the *Paramecium vulgaris* is demonstrated in FIG. 12a. Only slight changes in the intensity of the red chlorophyll fluorescence can be seen through the *Paramecium vulgaris* cytoplasm. Using the previously-described similarity mapping algorithm it was possible to display cellular structures which present some degree of spectral differentiation. Five fluorescence spectra of pixels chosen from the periphery and the middle of the *Paramecium vulgaris* cell (FIG. 11a) served as basis for comparison of all the other pixel spectra, and the results are shown in five different enhanced images. Each of these spectra was compared by similarity mapping to all the other pixel spectra. These results are presented in FIGS. 12b–f.

As shown in FIG. 12b, similarity mapping using spectrum 1 of FIG. 11a as reference, revealed two distinct regions (in white) on the upper part of the *Paramecium vulgaris*. These spectra revealed a high content of native algal chlorophyll, and, therefore, most probably represent the cytopharynx and the buccal cavity. As shown in FIG. 12c, similarity mapping using spectrum 2 of FIG. 11a as reference reveal tiny spots of about one pixel each, next to the cytopharynx and cytosol, representing migrating vacuoles. As shown in FIG. 12d, similarity mapping using spectra 3 or 4 of FIG. 11b as reference, revealed large vacuoles in the middle of the cytoplasm, consisting of degraded algae, as characterized by a low 630 nm peak. The image in FIG. 12e, achieved with by similarity mapping using spectrum 5 of FIG. 11c as reference, revealed narrow delineated regions of the same compartment as in FIG. 12d, representing nearly the same 630/695 ratio. Thus, FIG. 12e is an advanced stage of algal degradation by the same phagolysosome compartments. The similarity map shown in FIG. 12f, achieved by using spectrum 6 of FIG. 11d as reference, shows a major region near the outer pellicular system, most probably representing the cytoproct, where digested waste is eliminated from the cell. Such waste contains the lowest amount of native chlorophyll and the highest pheophytin content.

Figure 13:
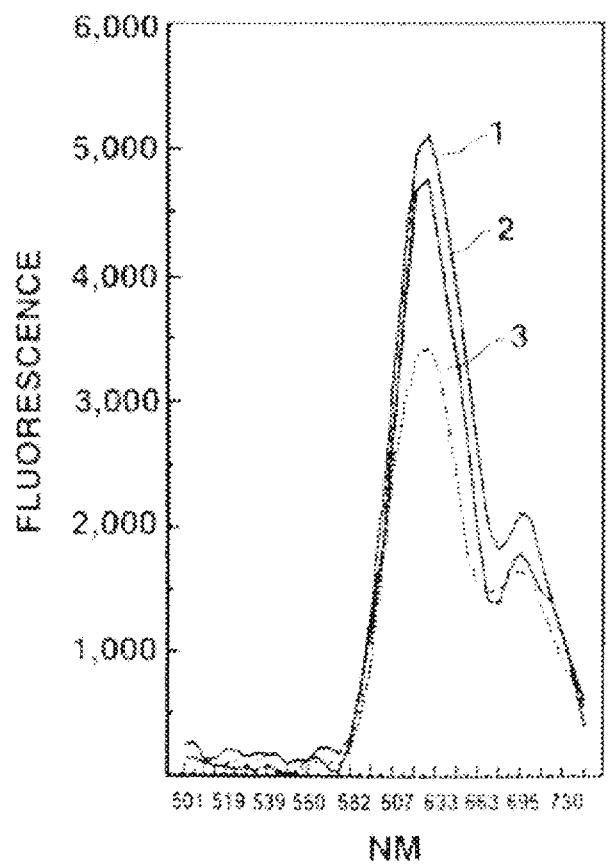
FIG. 13 is a fluorescence spectra of algal chlorophyll in the perialgal vacuoles of two mating Paramecia bursaria shown in FIG. 14. Different individual pixel spectra of upper (1) and lower (2) perialgal vacuoles of mating Paramecia; spectrum (3) was taken from a pixel in a middle contact region of the two cells shown in FIGS. 14a–c.
Figure 14:
FIGS. 14a, 14b and 14c show (a) fluorescence of algal chlorophyll in a perialgal vacuoles of two mating Paramecia bursaria; (b) similarity mapping image of perialgal vacuoles and native chlorophyll content in mating Paramecia (mapped with spectrum 2 of FIG. 13), one cell contains a larger food vacuole and the other, a smaller one, and therefore they correspond to type I and type II cells, respectively; (c) the low intensity spectrum 3 of FIG. 13 was used for mapping and represents the reflected red light in the cytoplasm of the cells.

FIG. 13 reveals the red fluorescence spectra of algal symbionts living in the perialgal vacuoles of two mating *Paramecia bursaria*. Spectra 1 and 2 are of the upper and the lower vacuoles of the mating Paramecia, respectively. These two spectra show a high 630 nm peak and a very low 695 nm peak. The same spectra, of an enhanced 695 nm peak, were recorded in any pixel of the perialgal vacuoles, without spectral changes at any site in the cell. FIG. 14a reveals a similarity mapping image of the perialgal vacuoles and the native chlorophyll content in the mating Paramecia, using spectrum 1 of FIG. 13 as a reference spectrum. The process of sexual mating in Paramecia begins by the attachment of the two mating cells, type I and type II, which commonly adhere at the buccal region of their bodies. The two cells shown in FIG. 14b, one containing a larger perialgal vacuole than the other as mapped using spectrum 2 of FIG. 13 as reference, correspond to type I and type II cells, respectively [Morris et al. (1994) Appl Spectroscopy 48, 857–866]. When using the low-fluorescence intensity spectrum 3 of FIG. 13 as reference for similarity mapping, shown in FIG. 14c, one can see the cytoplasm of the two mating cells. The lack of chlorophyll decomposition clearly indicates the symbiotic state of algae in these cells.

Hence, Example 1 demonstrates the ability of Fourier transform mutipixel spectroscopy combined with suitable algorithms to reveal spectral information from a single living cell. The spatial information reveals both the fluorescence intensity and full spectrum point-by-point information with which localized biochemical information can be unveiled using a similarity mapping algorithm. Pixel by pixel information could not be obtained as easily by using conventional microfluorometry or by using narrow band filters. Ratio imaging based on changeable filters has intrinsic limitations as it demands primary spectral information, which is not easily available. Another limitation is the need to adjust a small number of suitable filters. Thus filter-based imaging will not give ready access to the wavelength and space dependent intensity of a sample. On the other hand, tunable filter devices for spectral imaging, are inappropriate for biological methods [Morris et al. (1994) Appl Spectroscopy 48, 857–866]. The method of confocal scanning laser microscopy combined with prism-optical spectrometry [Trepte et al. (1994) J. Microscopy 176, 238–244] has the capacity to reveal pixel spectral information, but until now has not been developed for similarity mapping and image reconstruction based on multipixel spectral information.

Figure 15:
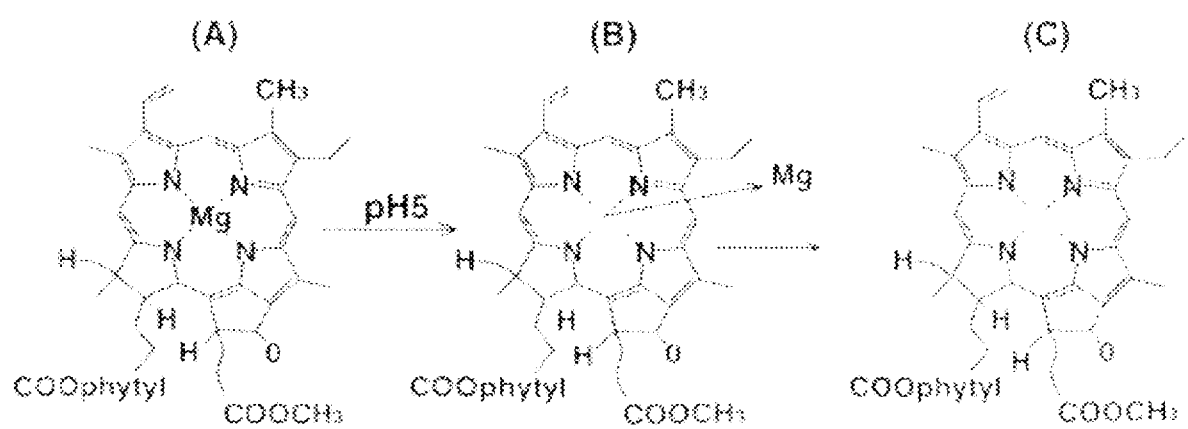
FIG. 15 show steps in the degradation of chlorophyll α into pheophytin and opening of the tetrapyrrole ring.
Figure 16:
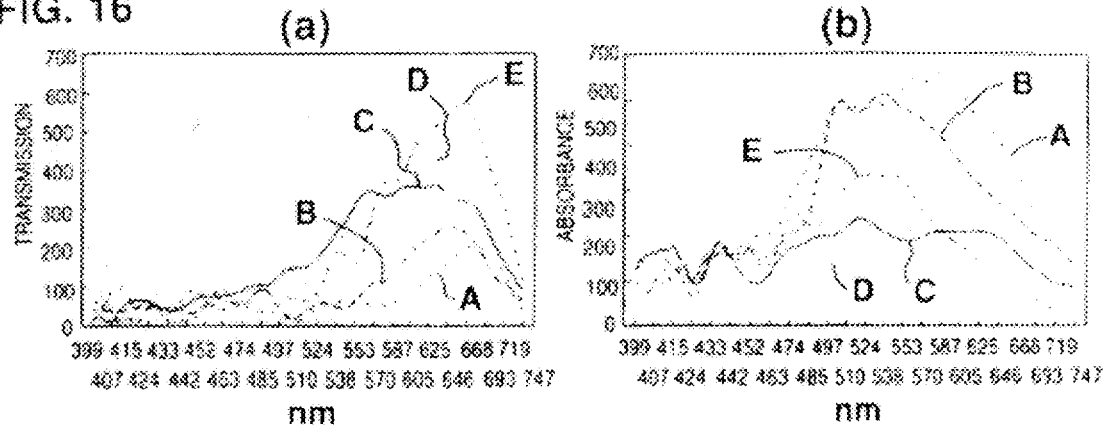
FIGS. 16a and 16b show a multipixel transmittance (a) and absorbance (b) spectra of five different cellular sites (i.e., individual pixels) of May-Grunwald-Giemsa stained erythoblast cell.
Figure 17:
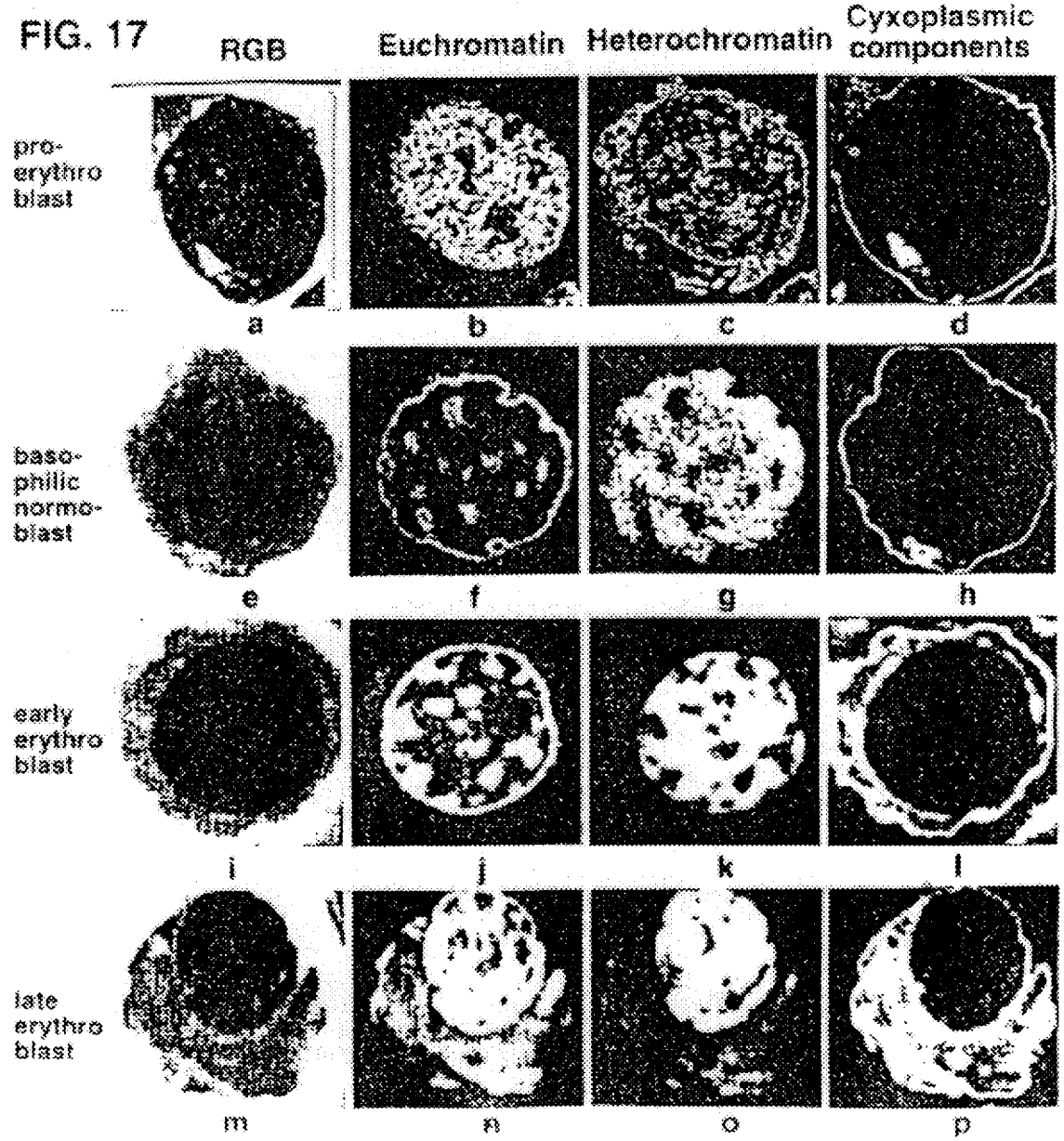
FIGS. 17a, 17b, 17c, 17d, 17e, 17f, 17g, 17h, 17i, 17j, 17k, 17l, 17m, 17n, 17o and 17p show RGB (a, e, i, m) images and similarity mapping results obtained from spectra of euchromatin (b, f, j, n), heterochromatin (c, g, k, o) and of cytoplasmic components (d, h, l, p) of a proerythroblast (a–d), a basophilic normoblast (e–h), an early erythroblast (i–l) and a late erythroblast (m–p)
Figure 18:
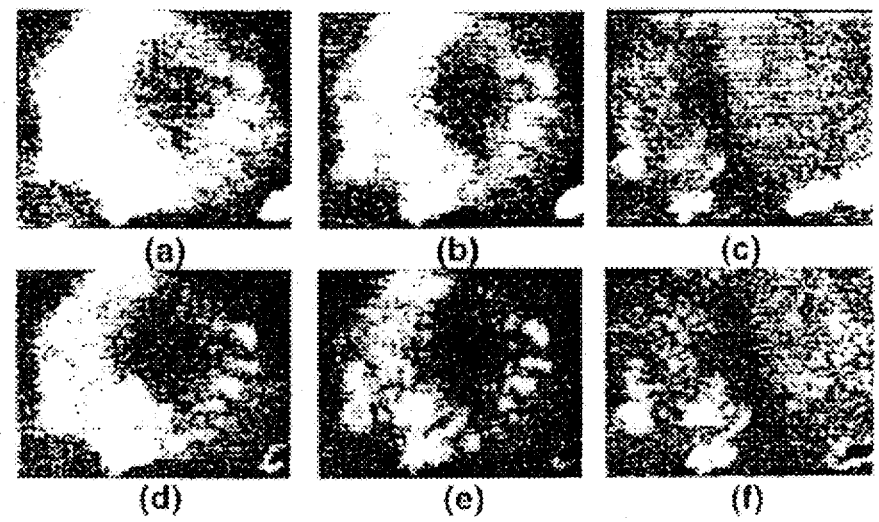
FIGS. 18a, 18b, 18c, 18d, 18e and 18f show subcellular localization of endo-PP fluorescence during photosensitization in B-16 melanoma cells. The cells were cultured with 5-ALA for 20 hr, thereafter the cells were exited with 400 nm light and red fluorescence was imaged and analyzed using a similarity mapping analysis with reference spectra of FIGS. 19a–c.
Figure 19:
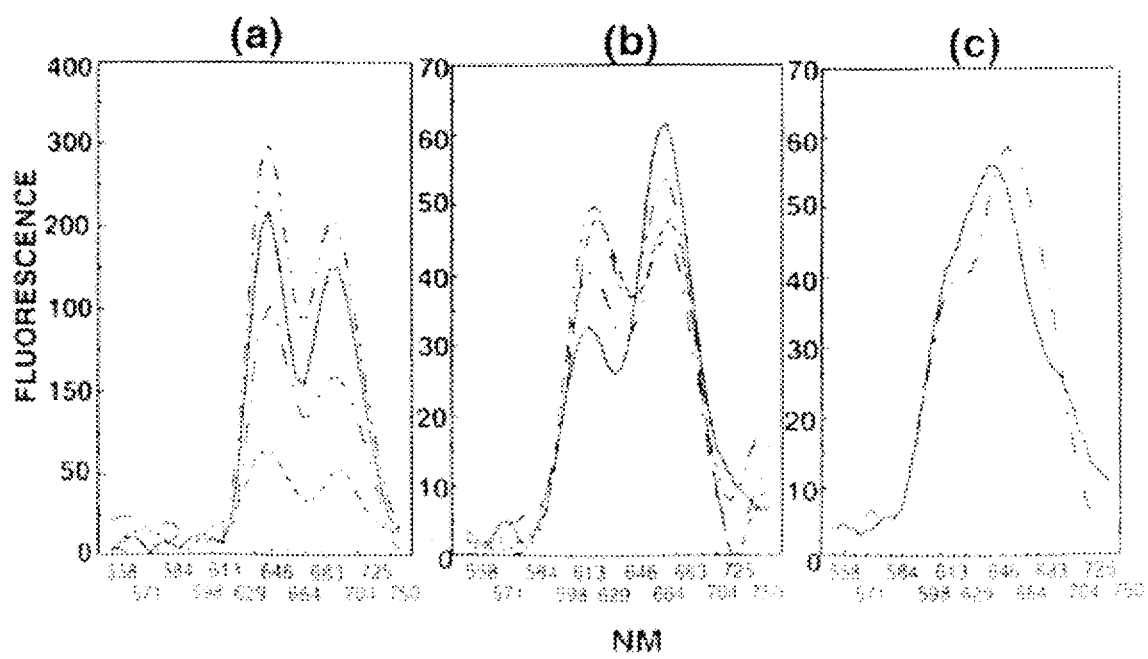
FIGS. 19a, 19b and 19c show four, four and two individual pixel fluorescence spectroscopy from the cells shown in FIGS. 18a, 18b and 18c, respectively.
Figure 20:
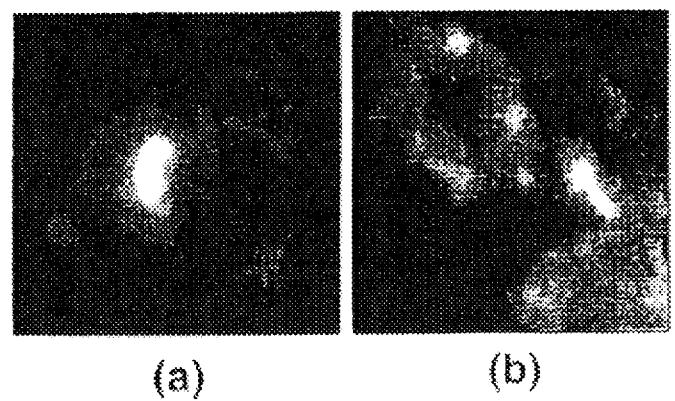
FIGS. 20a and 20b show compartmental localization of fluorescence of exogenous PP in single melanoma cell incubated with PP in a serum-enriched medium, wherein (a) shows red fluorescence of a control melanoma cell after incubation with exo-PP; and (b) shows red fluorescence distribution after 1 min light irradiation (4 J/cm$^2$) of a similar cell as in (a).
Figure 21:
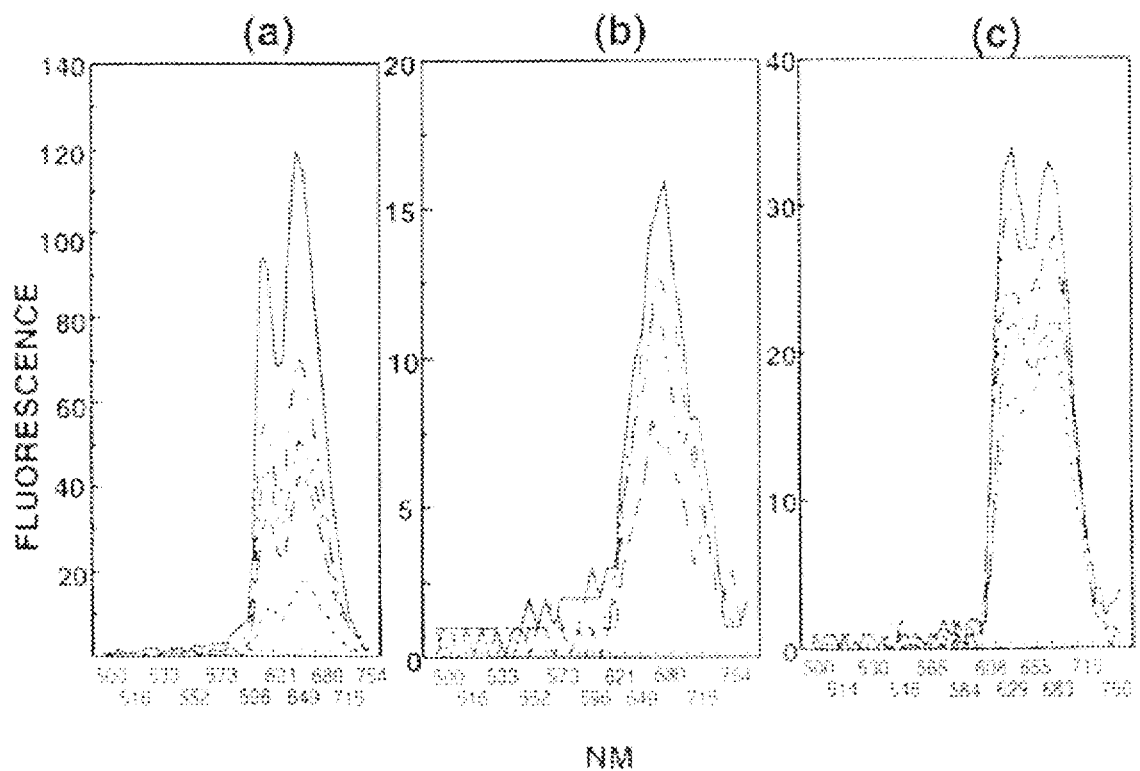
FIGS. 21a, 21b and 21c show single pixel fluorescence spectroscopy of the cell in FIGS. 20a, 20b and of an additional image of the cell taken after incubation in dark for five minutes wherein (a) shows five single pixel spectra from different sites (i.e., individual pixels) of fluorescent subcellular sites in the cell shown in FIG. 20a; (b) shows four spectra from the cell of FIG. 20b after light irradiation; and (c) shows four spectra from subcellulai sites of the cell after post incubation in the dark for an additional five minutes.

In this Example, the potential of Fourier transform multipixel spectroscopy was applied to visualization of the compartmentalized chlorophyll degradation process in single living cells. The biochemistry of the food cycle in *Paramecia vulgaris* consists of two main processes, the first of which is, as is the general rule of any endocytotic vesicle, acidification of the ingested content by proton pumping into the vacuole. In the next step, lysosomal fusion with the endocytotic vesicle forms the endolysosome in which hydrolytic enzymes hydrolyze the ingested algae. The combination of low pH and hydrolytic lysosomal activity degrades the native chlorophyll into pheophytin, as illustrated in FIG. 15 (molecules A and B). Loss of magnesium from the chlorophyll is the basis of a spectral fluorescence shift from 630 nm to 695 nm. Further hydrolytic activity of lysosomal enzymes opens the tetrapyrrole ring and forms a linear structure which is not fluorescent (FIG. 15 molecule C). These three situations in the results were demonstrated hereinabove, and have located cellular sites where such changes take place. Using the spectral information, it was possible to localize sites of native chlorophyll, of pheophytin, and sites of low fluorescence which represent the end of the degradation cycle.

Images obtained by spectral mapping and image reconstruction of any identifiable spectrum of the chlorophyll or pheophytin contain spatial information and the localization of biochemical processes. Thus, spectral image analysis using the methods of the present invention are ideal to delineate metabolic processes in living cells in which spectral changes take place during enzymatic reactions.

EXAMPLE 2

CHROMATIN CONDENSATION IN BONE MARROW NORMOROBLASTS AND MEGALOBLASTS: IMAGING BY MULTI-PIXEL SPECTRAL ANALYSIS AND SIMILARITY MAPPING.

Standard analysis of blood cells is based on staining with either May-Grunwald-Giemsa or Romanowsky techniques which employ the dyes azure-B and Eosin. Spectroscopic microanalysis has been shown to enhance the data which can be obtained from cells stained by conventional methods. Thus, by a spectral subtraction technique, Galbraith et al. have shown that the differential coloration of various cell structures can be explained in terms of varying proportions of dye components [Galbraith et al. (1980) J-Microsc. 119(3): 313–30]. Friedrich et al. have shown that Romanowsky-Giemsa stained cell nuclei have a sharp and intense absorption band at 552 nm, the so-called Romanowsky band, which is due to the Eosin chromophore of the dye complexes. Other absorption bands were assigned to the DNA-bound azure-B cations [Friedrich el al. (1990) Histochemistry 93(3): 247–56]. The Eosin anions are mainly bound by hydrophobic interaction to the azure-B framework of the electrical neutral DNA-azure-B complexes. The Eosin absorption is red shifted by the interaction of Eosin with the azure-B framework of DNA-azure-B-Eosin complexes [Friedrich et al. (1990) Histochemistry 93(3): 247–56]. By adopting computerized spectroscopic microanalysis of nuclear chromatin granularity, Spina et al. showed a significant distinction between benign and malignant breast cells [Spina et al. (1992) Virchows-Arch-B-Cell-Pathol 62(2): 119–24]. The principle of this approach was based on analysis of the abrupt transition from eurochromatic to heterocluomatic foci of high contrast gradient, as a parameter for coarseness in smears stained by the May-Grunwald-Giemsa technique. In this technique, computer-assisted subtraction between two image lowpass filters was used, thus retaining only high contrast gradient values on the digitized image.

During maturation of the red cell precursors, both nucleus and membrane show a series of qualitative morphologic changes. The earliest recognizable member of the red-cell series, the proerythroblast, has cytoplasmic basophilia, nucleololi, fine reticular or stippled nuclear chromatin and a large cell size, generally characterizing primitive cells. The proerythroblast gives rise to a sequence of nucleated cells, the erythroblasts, which progressively develop increasingly condensed nuclear chromatin, lose their nucleoli and their cytoplasmic basophilia and acquire a rising hemoglobin content. This sequence is subject to an arbitrary division into stages, which are usually three: (I) Basophilic or early erythroblast, or normoblast A; (II) Polychromatic or intermediate erythroblast, or normoblast B; (III) Orthochromatic or late erythroblast, or normoblast C [Hayhoe and Flemans (1992) Hematological Cytology, 3rd ed. p. 11, Wolfe Publishing Ltd. London]. The nucleus in the orthochromatic normoblast is small and pyknotic and the cytoplasm is slightly polychromatophilic. Nuclear maturation abnormalities in either proerythroblasts or normoblasts are observed in various conditions, such as vitamin B12 or folate deficiency, myelodysplastic syndrome, chemotherapy effect, etc.

The purpose of this example is to show the SpectraCube™ system combined with the methods of the present invention abilities to acquire multipixel spectroscopic information from nuclei of human erythropoietic bone marrow cells and to correlate the spectroscopic data with chromatin condensation. Thus, correlations between nuclear chromatin structure and differentiation will be possible on a spectroscopic basis independently from the geometry and spatial orientation of the nuclei.

Multipixel spectra of May-Grunwald-Giemsa stained erythroblasts was analyzed. Typically $10^4$ spectra from a single cell were obtained, each representing a different cellular site (i.e., pixel) of the cell. Two complimentary data sets were obtained for each pixel: transmittance and absorbance spectra. FIGS. 16a and 16b, respectively, present the transmittance and absorbance spectra of five different cellular sites (i.e., pixels) of a single cell. Spectrum A is of heterochromatin, spectrum B is of euchromatin, spectrum C is of a cytoplasmic organelle (i.e., blue cytoplasm), spectrum D is of cytoplasm (i.e., pink cytoplasm), and spectrum E is of Golgi apparatus. The transmittance spectra of cell nuclei (for example spectrum A of FIG. 16a) from different erythroid differentiating cells depict a similar pattern: low light transmitance of heterochromatin in the region of 450–700 nm, accompanied with maximum absorbance at 550 and 570 nm, as shown in spectrum A of FIG. 16b. The sharp absorbance peak at 550 nm may be attributed to the so called Romanowski-DNA complex. Thus, specific spectral details on a subcellular level were obtained. The spectra of euchromatin (for example spectrum B in FIGS. 16a and 16b) in the erythroid cells showed a higher green and red light transmittance capacity and absorbance in the spectral region of 550–720 nm. These general characteristic spectral appearance varied from one nuclear site to another.

The cytoplasm stain-binding attributes showed a different pattern, in general it depicted a higher light transmitance capacity and blue shifted absorbance spectra (for example spectra C and D of FIGS. 16a and 16b). Golgi-like regions (spectrum E in FIGS. 16a and 16b) and other cytoplasmic arrays revealed localized spectral patterns.

As shown in FIGS. 17a–p, the spectra of euchromatin, heterochromatin and of cytoplasmic components (spectra A, B and D of FIG. 16a, respectively) were used as reference spectra for similarity mapping analysis with the rest $10^4$ spectra of original images of four cells representing four stages of erythropoiesis (i.e., differentiation stages of erythrocytes). As delineated above, similarity mapping function calculates the difference between area-integrals of one chosen spectrum to all the other spectra of the spectral cube. The reconstructed image is composed of more or less bright pixels according to a gray scale, which reveals the degree of similarity between the two. Thus, in this example, the brighter the pixel, the more the two spectra are alike. FIGS. 17a, 17e, 17i and 17m present the original RGB images of proerythroblast, basophilic normoblast, early erythroblast and late erythroblast, respectively. Note that by examining the original RGB images no differences, but to some extent the nucleus size (compare FIGS. 17m and 17i), are visible among the four different erythroblastic cells. FIGS. 17b, 17f, 17j, 17n are eucluomatin similarity mapping results of the four cells in which as a reference spectrum employed was spectrum B of FIG. 16a, and reveal nuclear arrays of euchromatin (white regions). FIGS. 17c, 17g, 17k, 17o are heterochromatin similarity mapping results of the four cells in which as a reference spectrum employed was spectrum A of FIG. 16a, and reveal nuclear arrays of heterochromatin (white regions). Note that as the cell examined is more differentiated the amount of euchromatin is decreased and the amount of heterochromatin increased. Further note that comparing the arrangement of euchromatin and heterochromatin in the examined cells reveal a complementary image (compare for example FIGS. 17f and 17g). The euchromatin and heterochromatin images of proerythroblast (FIGS. 17b and 17c, respectively) reveal that the major nuclear area is composed of the stained-euchromatin complexes arranged in small patches disconnected from each other. FIGS. 17f and 17g show a basophilic erythroblast. The spectral maps of euchromatin, in comparison to heterochromatin (FIG. 17f as compared with FIG. 17g, respectively) show marked differences from the proerythroblast pattern, in area size, condensation and distribution. The alterations of nuclear morphology and chromatin packaging along differentiation of early and late erythroblasts are further shown in FIGS. 17j, 17k, 17n and 17o. Note that euchromatin (FIG. 17n) and heterochromatin (FIG. 17o) images of late erythroblast show maximal condensation of chromatin into lobes. As shown in FIGS. 17b, 17f, 17j and 17n, euochromatin images detected also nuclear envelope. FIGS. 17d, 17h, 17l and 17p were obtained by similarity mapping to a cytoplasmic reference spectrum (spectrum D of FIG. 16a). cytoplasmic vacuoles (e.g., Golgi apparatus, spectrum E of FIG. 16a) showed a similar spectroscopic staining depiction (not shown). These images shows a Golgi like structure and the outer border of the cell.

Thus, spectral image analysis and spectral mapping using the SpectraCube™ and a similarity mapping algorithm in accordance with the present invention, resolved the gradual chromatin condensation into chromosomal arrays taking place prior to nuclear expulsion. This spectral imaging method is ideal to highlight minor changes of the condensed chromosomal arrays and their borders. The sharp border of the highly condensed chromatin domains in the early and in the late erythroblast made a specific distinction from the rest of the nucleoplasm (FIGS. 17k and 17o). These structures possibly correspond to specific organization of individual or grouped chromosomes.

Using the SpectraCube™ system combined with the methods of the present invention, thus enabled to monitor developmental changes occurring in a healthy tissue. Since various malignancies are also characterized by unique developmental features, the SpectraCube™ system and the methods of the present invention can be adopted to monitor these characterizing features and thus to assist in for example early diagnosis (e.g., existence and stage) of such malignancies.

EXAMPLE 3

5-AMINOLEVULINIC ACID MEDIATED PHOTODINAMIC THERAPY OF MELANOMA TUMORS: LIGHT-SENSITIZER INTERACTIONS DETERMINED BY SPECTRACUBE™ SPECTRAL IMAGING SYSTEM USING THE SIMILARITY MAPPING ALGORITHM.

Photodinamic therapy (PDT) of malignant melanoma has remained only partially understood [Marcus (1992) Photodynamic Therapy-Basic Principles and Clinical Applications. Edited by Henderson and Dougherty. Marcel Dekker, New York. pp. 219–268]. A strong correlation between the degree of tumor pigmentation and the degree of regression has been found, with the lighter tumors responding much better than darker tumors [Nelson et al. (1988) J Natl. Cancer Inst., 80, 56–60]. It was concluded [Favilla et al. (1991) Br. J Ophthalmol., 75, 718–721] that pigmented melanoma in humans does not respond satisfactorily to PDT, whereas amelanotic melanoma (such as of the iris) do respond positively. On the other hand, the remarkable effectiveness of 5-aminolevulinic acid (ALA) induced PDT of skin lesions and the results of experimental melanoma PDT mediated by ALA [Malik et al. (1987) Biol. Cell, 60, 33–40] have opened up new possibilities for the development of melanoma PDT. It was shown [Malik and Lugaci (1987) Brit. J. Cancer, 56, 589–595; Malik et al. (1989) J. Photobiol. Photochem. B, 4, 195–205; and, Hanania and Malik (1992) Cancer Lett., 65, 127–131] that protopoiphynin (PP) biosynthesized in leukemic cells from the natural precursor 5-ALA is a highly potent photosensitizer for the destruction of cancer cells even by low light-doses. 5-ALA-PDT has been applied successfully to human patients for the selective eradication of skin tumors, especially basal cell carcinoma, as well as for internal solid tumors [Peng et al. (1992) Int. J. Cancer, 52, 433–443]. Topical 5-ALA application, or its systemic injection, has been shown as highly selective both in demarcating the tumor and in its photodestruction [Kennedy and Pottier (1992) J Photochem. Photobiol. B., 14, 275–292; and, Peng et al. (1992) Int. J. Cancer, 52, 433–443]. These results are a direct consequence of the markedly elevated PP biosynthesis and accumulation in the fast-dividing transformed-cells in comparison to the surrounding normal tissue. 5-ALA-PDT can be considered a safe and powerful tool in selective tumor treatment and one of the challenges is to develop it for melanoma. It was demonstrated that the stimulation of endo-PP biosynthesis in B16 melanoma cells was markedly enhanced by chemical inducers of poiphyria in order to facilitate efficient photodynamic cell killing [Malik et al. (1987) Biol. Cell, 60, 33–40].

In the present example revealed are primary photochemical processes and photobiological reactions on single cells accumulating endogenous PP in comparison to treatment with exogenous PP. Spectral image analysis of the PP fluorescence showed multiple pixel changes in one cell; at least 100×100 (i.e., 10,000) different spectra were derived from a single cell. By the use of the spectral imaging and similarity mapping algorithm, as shown below, it was possible to locate point spectral changes and intracellular photosensitization targets in a single cell.

For this purpose, Murine melanoma cells, line B16 clone F10 were cultured in RPMI-1640 medium supplemented with 10% fetal calf serum and antibiotics [Malik et al. (1987) Biol. Cell, 60, 33–40], either in tissue culture plates or on Thermanox coverslips (Nunc, Napeivile Ill.), in a humidified atmosphere with 5% $CO_2$ at 37° C. For passage, cells were detached with trypsin EDTA and recultured twice a week. The protocol for stimulation of endogenous PP production by the is melanoma B16 cells consisted of: (1) an induction phase, followed by (2) a biosynthesis phase. The induction phase was accomplished by the treatment of the cells with DMSO for 48 hr. This was followed by phase (2)—incubation with 5-ALA (0.3 mM) for 24 hr in serum depleted medium. The pH of the 5-ALA-medium was adjusted to 7.0. After phase (2) the cells were pelleted, rinsed with PBS, and the extraction of porphyrins was carried out as described below. For experiments with exogenous porphyrins, Protoporphyrin IX (Sigma) was dissolved in NaOH 1N, diluted to 10 mM in phosphate buffer and added to the melanoma culture media for 24 hr. The same was done with Photofrin II (QLT) for localization experiments.

Melanoma B16 cells, accumulating porphyrins as described above by the action of DMSO and 5-ALA, were irradiated for 1–5 min, using a Philips 'black-light' source, emission 320–450 nm, with a maximum at 380 nm, and delivering 20 W/m². The cells were irradiated with light doses of 1–4 $kJ/m^{-2}$. Illumination was measured by a Quantum Radiometer Photometer Model LI-185 (Lambda Instrument Corp., Lincoln, Northeast, U.S.A.).

The subcellular localization of endogenous protoporphyrin (endo-PP) during photosensitization in B-16 melanoma cells was analyzed by the SpectraCube™ system according to the methods of the present invention. The melanoma cells were incubated with ALA and then the fluorescence of endo-PP was recorded in individual living cells by 3 modes: (1) the conventional fluorescence image; (2) a 100×100 pixel fluorescence spectral image; and, (3) a processed image formed by operating a spectral similarity mapping and reconstructing the image from point spectral information. As shown in FIG. 18a, a raw fluorescence image revealed vesicular distribution of endo-PP all over the cytosol. This pattern of endo-PP localization possibly reflects mitochondrial and lysosomal, as well as endoplasmic reticulum cisternael accumulation. These intracellular organelles were shown to be the main targets during photosensitization. FIG. 19a shows four PP fluorescence spectra, each derived from a different cellular site of the cell shown in FIG. 18a and each has one peak at 635 nm and another one at 705 nm. The relative intensities of these two peaks did not change position from one site to another in the intracellular compartments of the treated cell. One fluorescence spectrum, shown in FIG. 19a (solid line), was chosen from one vesicle in the cell in FIG. 18a. The image in FIG. 18d was reconstructed by similarity mapping using the chosen spectrum (solid line in FIG. 19a) as reference. As shown in FIG. 18d, the reconstructed image revealed the demarcation of membrane and vesicle fluorescence. Shown in FIG. 18b, during 1 min of light exposure, the endo-PP in single cells was bleached, fluorescence intensity decreased and the different measured spectra, shown in FIG. 19b, revealed a left handed shift to 625 nm and 670 nm. The intensity-ratio between these two peaks revealed a mixed situation from site to site in the cell. Similarity mapping using the solid line spectrum of FIG. 19b as reference, formed a new image shown in FIG. 18e basically similar to the one shown in FIG. 18d. As shown in FIG. 18c, after a longer light irradiation interval (3 min), the fluorescence image of the cell was markedly affected. As sown in FIG. 19c, the spectra taken from two different points in the cell of FIG. 18c, showed one peak at 650–670 nm. The fluorescence image (FIG. 18c), or, shown in FIG. 18f, the image resulted from similarity mapping using the spectrum shown in a solid line in FIG. 19c as reference, in which image no sharp organelle structures could be seen, are conceivably a result of cellular damage. Thus, spectral alterations could point to two main effects: one, the formation of photoproducts [Konig et al. (1993) J. Phtochem. Photobiol. B: 18, 287–290] at the subcellular level as the most probable outcome of photosensitization, and, on the other hand, the possibility of pH changes during photoirradiation can not be excluded.

Endogenous PP which is biosynthesized in different subcellular compartments and is accumulated in the mitochondria is shown by the present example to be retained in a hydrophilic environment. Light exposure has produced two effects: formation of some photoproducts and pH changes in the microenvironments. The effects and contributions of the microenvironment; hydrophobicity, hydrophilicity, acidity, versus formation of photoproducts [Konig et al. (1993) J. Phtochem. Photobiol. B: 18, 287–290] are difficult to separate by micro-fluorescence spectroscopy on single living cells.

A quite different intracellular compartmental localization was visualized in single melanoma cells incubated with exogenous PP (exo-PP) in a serum-enriched medium. FIG. 20a reveals the fluorescence image and specific localization of exo-PP in a perinuclear region, most probably covering the Golgi complex and the nuclear envelope. In addition, fluorescence could be seen in other sites of the cytosol and also faintly on the outer membrane. As shown in FIG. 21a, spectra of five individual pixels of the cell shown in FIG. 20a revealed two unique characteristic fluorescence peaks that did not differ from pixel to pixel and only the intensity was changed. One can see that the main fluorescence peak is located at 670 nm, while the minor peak is at 625–630 nm. As shown in FIG. 20b, photosensitization of one minute of the exo-PP, induced immediate damage and relocalization. The central localization of the exo-PP changed to an overall circular localization surrounding the nuclear-envelope. As shown in FIG. 21b for four individual pixels, the 630 nm peak disappeared completely, and the fluorescence shifted to 650–670 nm. As shown in FIG. 21c for four individual pixels, post incubation in the dark for an additional 5 min revealed a partial recovery of fluorescence. The new spectra showed two peaks at 630 and 670 nm at the different subcellular sites.

Hence, these results indicate that the exo-PP added to serum-enriched culture media was taken up via endocytosis, and delivered through the endocytotic-endosomal route to the Golgi complex. The assumption on endosomal localization is supported by spectral analysis showing the influence of acidic pH on the spectra. Similar findings on the pH effect on porphyrin fluorescence spectra was demonstrated by Pottier [Pottier (1990) J. Photochem. Photobiol. B: Biol., 6, 103–109]. Some of the exo-PP is localized in outer membranes. Light irradiation affected the red fluorescence, revealing formation of photoproducts from the exo-PP. Post incubation in the dark changed the point characteristics of the spectra and specific localization was found now on the nuclear envelope. One may suggest that the marked spectral shifts reflect porphyrin location in less acidic environments and photoproducts formation. Spectral imaging enabled to visualize and determine subcellular spectral changes in single cells, a method which markedly differs from conventional fluorescence spectroscopy of a cell population. Thus, fine spectral shifts in cytoplasmic organelles as well as localization of photoproducts could be revealed by the method of the present invention.

EXAMPLE 4

EFFECT OF EPIBIONTS ON THE MICRO DISTRIBUTION OF CHLOROPHYLL IN CORALS AND ITS DETECTION BY FLUORESCENCE SPECTRAL IMAGING.

Hermatypic (reef building) corals harbor in their tissues endosymbiotic algae, known as zooxanthellae. The zooxanthellae contribute their photosynthetic products to the host coral [Muscatine et al. (1989) Proc. R. Soc. Lond. B 236: 311–324; Lewis and Smith (1971) Proc. R. Soc. Lond. B. 178: 111–129] and can absorb its wastes as dissolved inorganic nutrients. Muscatine and D'Elia [Muscatine and D'Elia (1978) Limnol. Oceanogr. 23: 725–734] have shown that absorption and retention of ammonium in hermatypic corals is enhanced by light, indicating its assimilation by the zooxanthellae. Changes in ammonium concentration affect the population density of zooxanthellae [Muscatine et al. (1989) Proc. R. Soc. Lond. B 236: 311–324]. Bythell [Bythell (1988) Proc. 6th Int. Coral Reef Sym. Australia. 2: 535–540] demonstrated that there is a net uptake of ammonium by zooxanthellae, and that any ammonium produced from catabolic breakdown of amino acids must be recycled within the symbiotic association. He suggested that the low availability of nitrogen imposed severe limits on the productivity of the association.

The zooxanthellae acquire some of the nitrogen and phosphorus rich wastes produced by their cnidarian host's catabolic activities [Johannes et al. (1970) Limnol. Oceanogr. 15: 579–586]. The internal cycling of ammonium furnishes some of the nitrogen requirements of the association. This way of conserving and recycling nitrogen is essential for survival in oligotrophic waters. However, since recycling only prevents losses but not provide additional nitrogen for growth and reproduction, external sources are also required to support these demands.

The population density of zooxanthellae is limited by nutrient supply [Hoegh-Guldberg and Smith (1989) Mar. Ecol. Prog. Ser. 57: 173–186; and, Cook and D'Elia (1987) Symbiosis 4: 199–212]. Comensals living in close association with the corals may also contribute catabolic nitrogen to the association, inducing increase in zooxanthellae density in their close vicinity. Meyer and Schultz [Meyer and Schultz (1985) Limnol. Oceanogr. 30: 157–166] have suggested that fish resting over coral heads may increase tissue biomass and zooxanthellae concentration by elevating nutrient levels in the form of excreta.

Corals also harbor a variety of invertebrates; some are sessile and attached to the coral skeleton, other burrow within it or are overgrown by the coral tissue and skeleton. The coral inhabiting crab *Cryptochirus coralliodytes* is found in pits in massive coral skeletons and is common in faviidae corals in Eilat, Israel. Potts [Potts (1915) Papers from the department of Marine Biology: 33–69] described the morphology of these crabs and the structure of their pits. However, the nature of the relationship between the crab and its host is unclear. It is suggested that the coral epibionts may contribute their excreta to the adjacent algae including zooxanthellae.

Barnacles comprising the sub family Pyrgamatinae are obligatory symbionts of corals. Although some authors argue that there is exchange of material between the coral and the barnacle, such a relationship has not yet been demonstrated. Cook et al. [Cook et al. (1991) Hydrobiologia 216/217: 285–290] showed that phosphorus excreted by the barnacle *Savignium milleporum* is absorbed by the zooxanthellae of its host *Millepora dichotoma*.

Species of the mussel Lithophaga borrow into the skeleton of living corals [Kleemann (1980) Reef. J. moll. Stud. 46: 13–54]. They use the living coral skeleton as a growing refuge and they take their food by filtration from the overlying sea. It was also showed that ammonium excreted by *Lithophaga simplex* living in *Astreopora myriophthalmia*, is absorbed by the zooxanthellae of the host coral.

It was therefore hypothesized that the symbiotic epibionts waste nurtures the surrounding area. This should result in higher zooxanthellae density in the close vicinity of the symbiont, as indicated by an increase in chlorophyll concentration. It is difficult to measure algal density at such minute distances and as far as known changes within this distance have yet to be demonstrated.

In this example described is the use of the methods of the present invention enabling to address this problem experimentally. Thus, the SpectraCube™ system was used to detect changes of chlorophyll concentration over a small area.

When chlorophyll molecules are excited by light, a photon is emitted in a process known as auto-fluorescence. The light emitted by fluorescence from a molecule is redder than that which exited it, the difference in wavelength representing the lost of vibrational energy. The emission spectrum of chlorophyll a fluorescence in vivo has its main band at about 685 nm. Most photosynthetic pigments are known to fluoresce in solution, however in vivo, chlorophyll a fluorescence is dominant because the other pigments transfer their absorbed energy to chlorophyll a with relatively high efficiency. Measurements of this fluorescence provide a tool for the detection and estimation of chlorophyll a [Kirk (1983) Light and photosynthesis in aquatic ecosystems. Cambridge University. Cambridge. p. 401]. When cnidarian tissues excited at either 365 nm or 405 nm, it emit at different wavelengths due to fluorescence substances in their tissue. However, the source of fluorescence at wavelengths greater than 650 nm is chlorophyll in zooxanthellae [Mazel (1985) Mar. Ecol. Prog. Ser. 120: 185–191]. Hardy et al. [Hardy et al. (1992) Mar. Ecol. Prog. Ser. 88: 247–255] measured chlorophyll fluorescence in order to demonstrate decrease in chlorophyll concentration in corals prior to visible bleaching.

For this purpose specimens were collected in the Red Sea in front of the Interuniversity Institute of Eilat. The following corals and their associates were used for the fluorescence analysis: *Favites halicora* with the pit crab *Cryptochirus coralliodytes*; *Goniastrea retiformis* with *Lithophaga lessepsiana*; and the hydrocoral *Millepora dichotoma* with the barnacle *Savignium milleporum*. The corals were brought to the laboratory and kept in aerated sea water. All measurements were performed within two days of collection. Zooxanthellae were isolated from corals by WaterPik [Johannes et al. (1970) Limnol. Oceanogr. 15: 579–586].

Fluorescence spectral imaging of isolated zooxanthellae was performed by the SpectraCube™ system attached to an epifluorescence microscope. Spectral similarity maps were created by selecting a pixel with a relatively high emission in each fluorescence map, and then comparing all other pixels in the fluorescence map to this pixel. Pixels with similar emission values to the selected pixel appear as bright dots, and the degree of similarity of the other pixels is expressed by the shade of the dots.

Spectral images of living corals were obtained by placing the corals in sea water and viewing them by the SpectraCube™ system equipped with a close up lens. The corals were illuminated with an Oriel Xenon Lamp, 250 watts. Broad band excitation light 380 nm to 580 nm (excitation filter BG-39, Schott, Germany) was used, the filter was placed between the light source and the corals, and an emission filter 590 nm (OG-59, Schott, Germany) between the coral and the spectral imaging camera.

Chlorophyll fluorescence values obtained at each pixel on the corals are dependent on chlorophyll concentration in a specific site and on the topography of it. The surface topography of the corals has a major effect on the intensity of excitation and emission light. In order to eliminate this effect, the excitation value of each pixel was adjusted to the highest excitation value in the series (standard normalization of spectra). Transacts were drawn along the images, crossing the symbiont animals. The intensity values of excitation and red emission of each pixel were measured. By choosing any red fluorescence pixet along the transact and comparing it to the other pixels, the computer program created a continuos normalized three-dimensional spectral presentation of wave length (Z axis) along the transact (X axis) and fluorescence intensity (Y axis). The 3D presentation showed the relative fluorescence intensity along the transact with the correction due to topographic effects on excitation.

Pixels were chosen at random on the image next to the symbiont animal, and four consecutive pixels were added.

The range between the first and the fifth pixel, at each serie, was 2.4 mm. The ratio between the emission and the excitation of each pixel was defined as the relative fluorescence index (RFI=emission/excitation). The normalized values of every 5 consecutive pixels were normalized again by relating them to the highest value pixel in the same series, resulting in relative values of each 5-pixel series.

Figure 22:
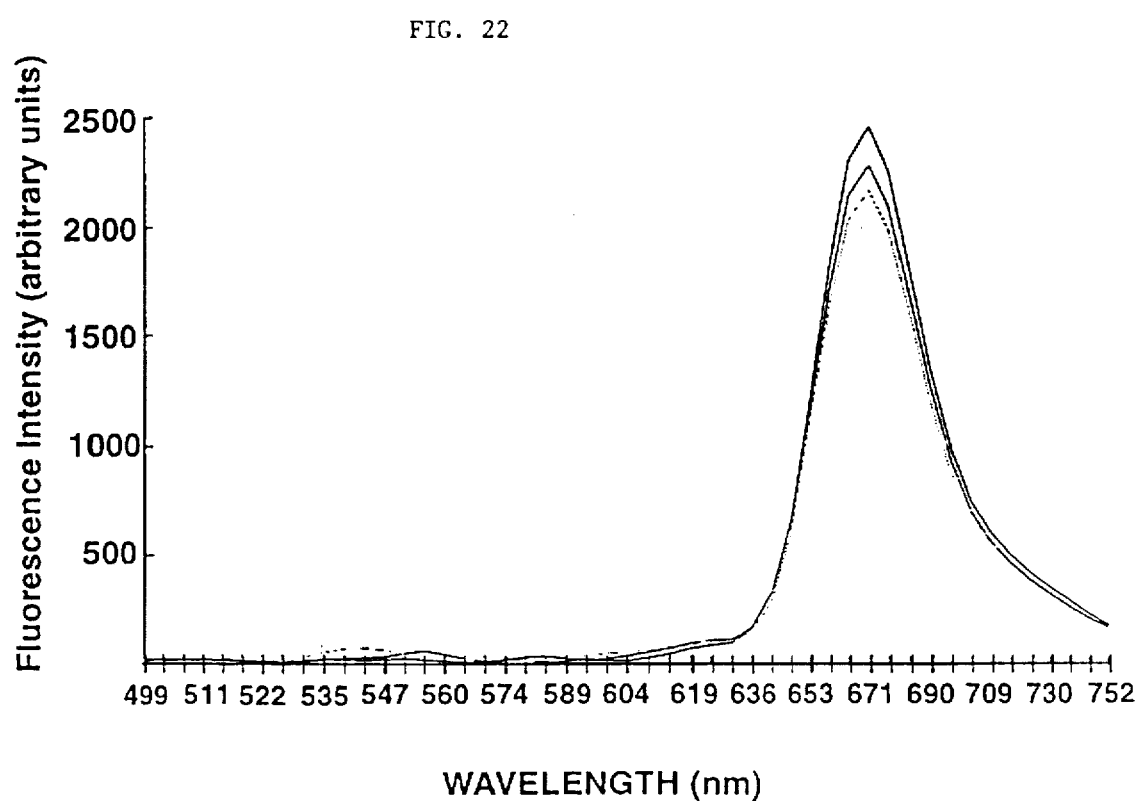
FIG. 22 shows a spectral graph of three random pixels of zooxanthellae fluorescence map showing emission peak at 671 nm.
Figure 23:
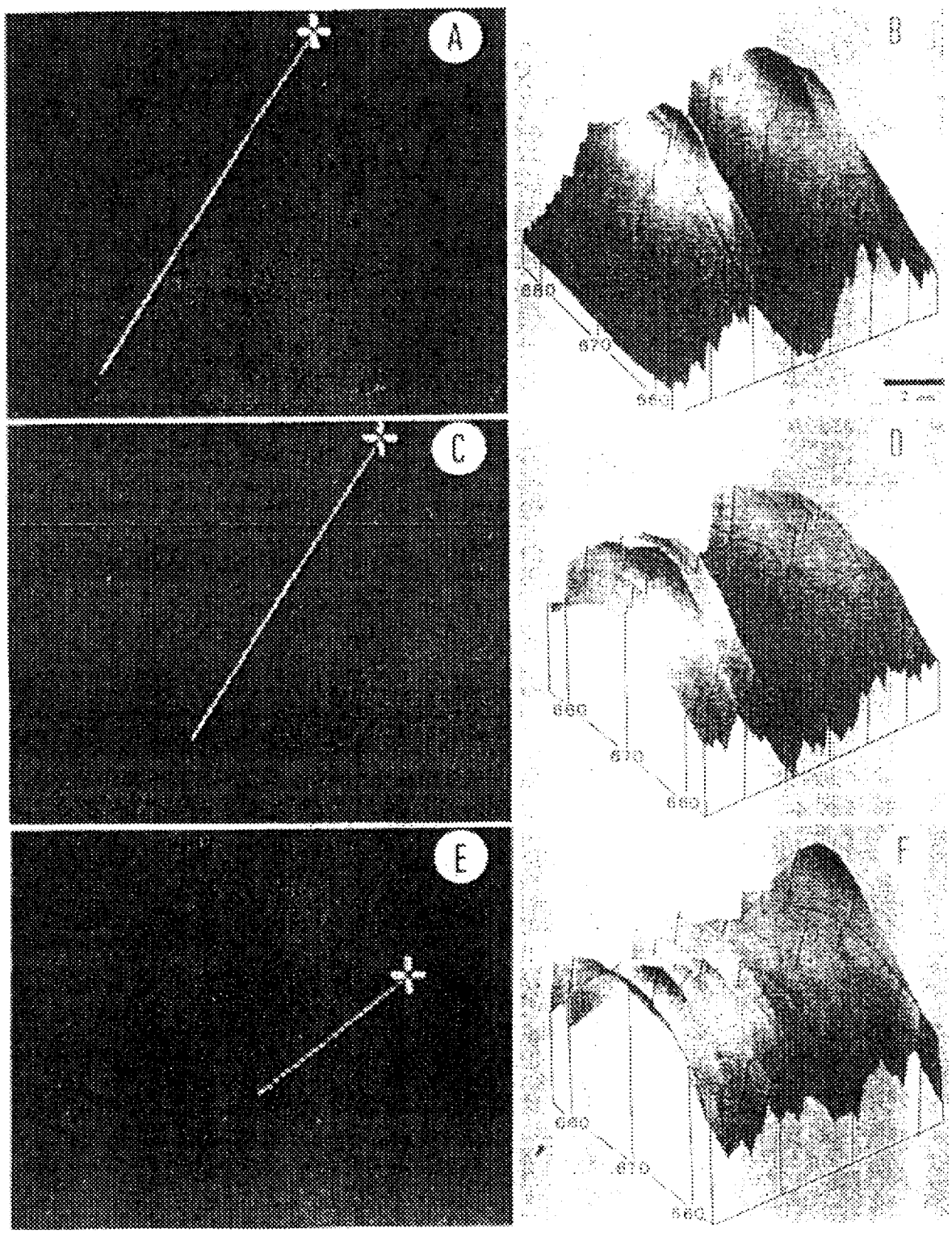
FIGS. 23a, 23b, 23c, 23d, 23e and 23f show (a), (c) and (e) multipixel fluorescence maps of three corals before normalization; and (b), (d) and (f) tri-dimensional diagram normalized relative to intensity of emission, between 654 nm and 685 nm, along transact shown on the fluorescence images (a), (c) and (e), respectively; (a) and (b) Favites halicora; (c) and (d) Goniastrea retiformis; (e) and (f) Millepora dichotoma.
Figure 24:
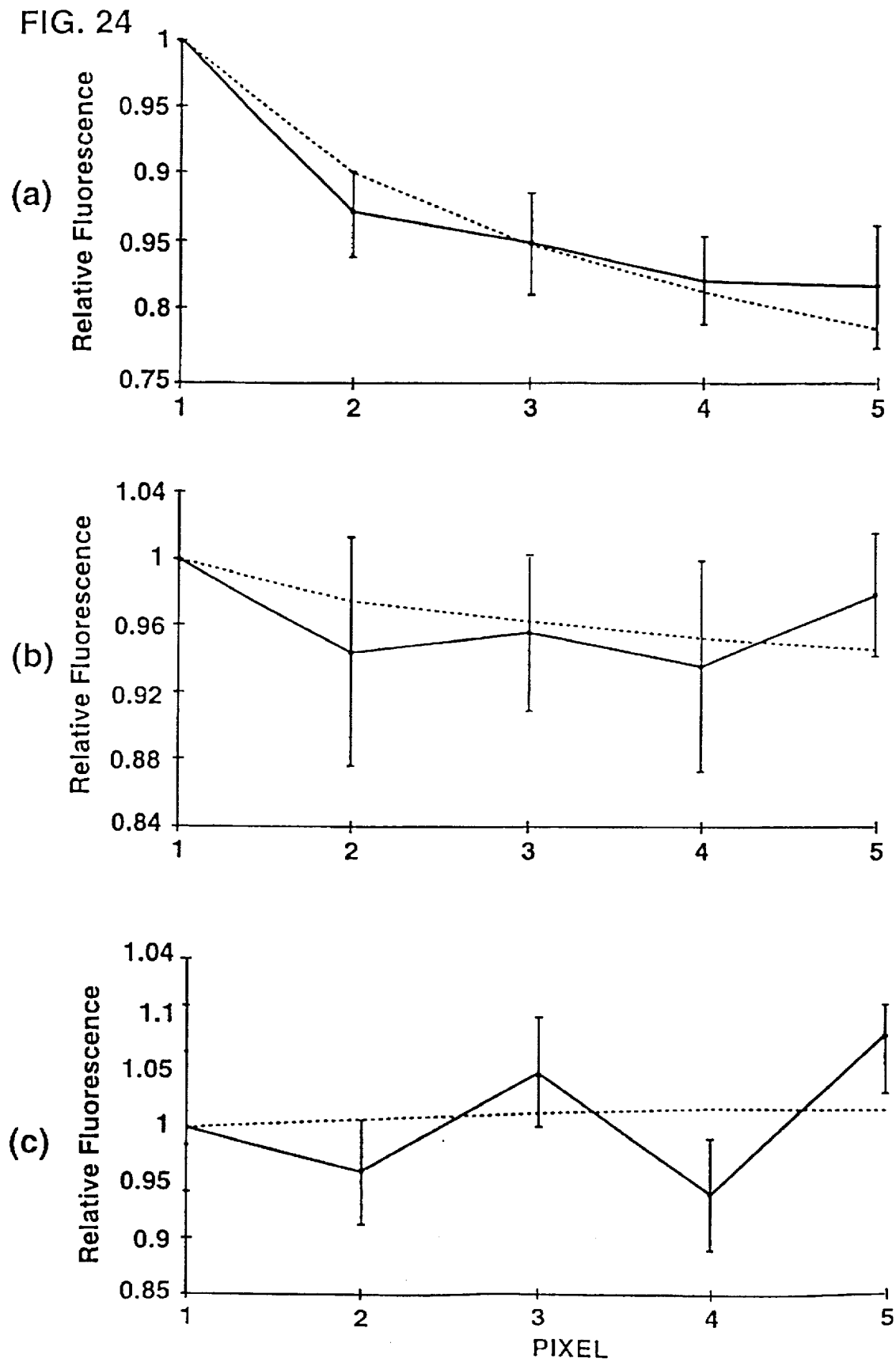
FIGS. 24a, 24b and 24c show regression curves of fluorescence values which are relative to pixels adjacent to symbiont (a) Favites halicora; (b) Goniastrea retiformis; and (c) Millepora dichotoma; the average of values measured from pixels found at the same distance along several radiating transacts are presented; the distance between the first point and the fifth point is 2.4 mm; vertical bars-±S.E.; dashed line-regression curve; regression results are Favites halicora r$^2$=0.905, Goniastrea retiforimis r$^2$=0.066, Millepora dichotoma r$^2$=0.062.
Figure 25:
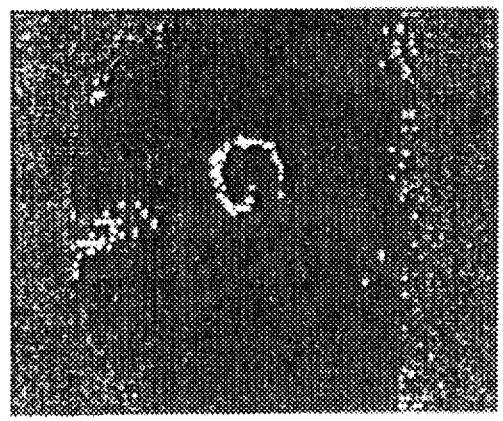
FIGS. 25a, 25b and 25c show spectral similarity maps of three corals (a) Favites halicora; (b) Goniastrea retiformis; and (c) Millepora dichotoma; all pixels were compared against a selected pixel with high fluorescence; similarity is indicated by a gray scale; bright pixels—high similarity, dark—low similarity.
Figure 25:
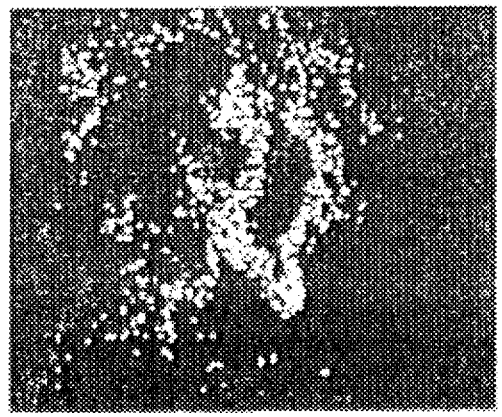
Figure 25:
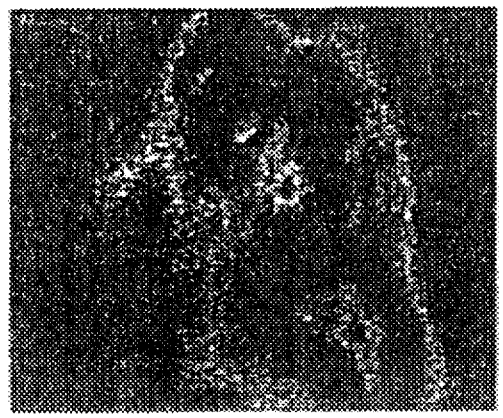
Figure 26:
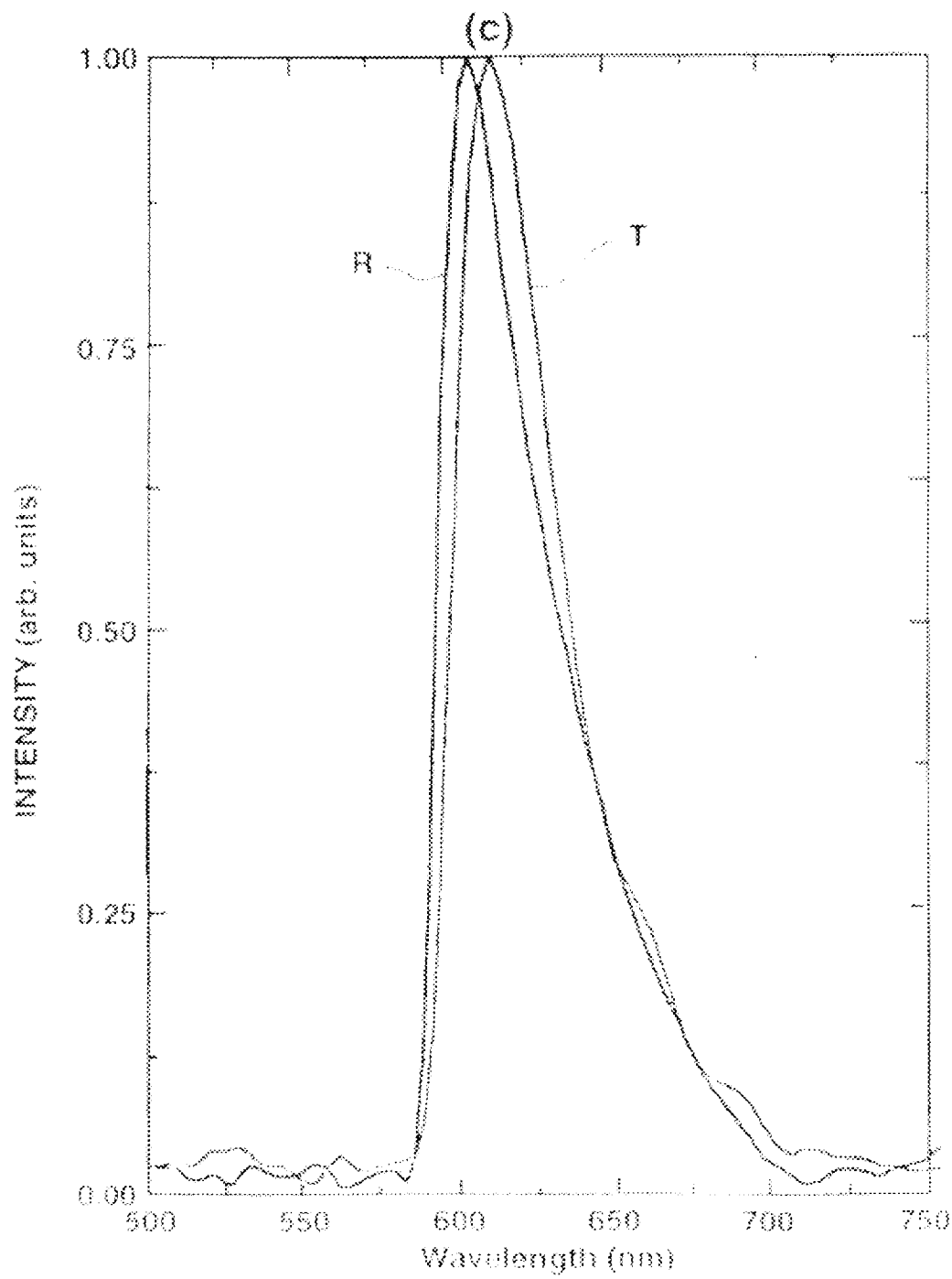
FIGS. 26a, 26b and 26c show interphase FISH performed with two different probes attached to Texas-Red and Rhodamine wherein (a) is an original image, the way it looks thorough a microscope; (b) is the same sample, after being measured and processed by the method of the present invention; and (c) are the fluorescence spectra of the Texas-Red and Rhodamine fluorophores.

In order to determine the fluorescence spectra of zooxanthellae, two isolated algae were used. As shown in FIG. 22, the spectrum curve of three random pixels upon a fluorescence map of the two zooxanthellae demonstrate the chlorophyll fluorescence peak at 671 nm.

The fluorescence of three corals carrying epibionts were analyzed. FIGS. 23a, 23c and 23e present the multipixel fluorescence map of the three host corals before normalization, and the transact used for spectral analysis. The transect crossed the symbiont. FIGS. 23b, 23d and 23f present the relative-intensity fluorescence, in the range of 654 nm and 685 nm, normalized as described above. Maximum emission was at 670 nm, typical for chlorophyll a. In *Favites halicora* (FIG. 23b) the highest fluorescence levels were found at the pit margins and there is a decline in fluorescence intensity along the transect moving away from the pit, indicating high chlorophyll concentration in the pit margins. There was however no emission from the pit itself. In *Goniastrea retiformis* and *Millepora dichotoma* (FIGS. 23d and 23f, respectively) there was no clear pattern of fluorescence along the transect. There was no emission from the mussel's siphon area and from the barnacle's orifice.

FIGS. 24a—c show the results of analysis of the average values of 9–11 pixels found at the same distance along several radiating transects. The values are relative to the pixels adjacent to the symbionts. Regression curves (dashed lines) are presented as well. Only in the case of Favites and Cryptochirus (FIG. 24a) can a clear gradient of fluorescence could be detected.

As shown in FIGS. 25a–c, spectral similarity maps were constructed for the three corals. As mentioned, the computer technique for similarity mapping compares a single chosen specific spectrum to the rest of spectra composing the original image. By calculating the differences between the reference algorithm to all others, it creates new images of spectral similarities as shown in FIGS. 25a–c. The highest relative fluorescence spectrum with the highest RFI value was chosen and used for spectral similarity mapping. FIG. 25a emphasizes the high chlorophyll concentration around the crab's pit. In *Goniastrea retiformis* (FIG. 25b) there is a higher fluorescence in the vicinity of the mussels (4 mm) siphon which was not revealed by relative-intensity fluorescence transect (FIG. 23d). In *Millepora dichotoma* (FIG. 25c) there is a similar pattern of localized chlorophyll fluorescence in the vicinity of the symbiont (3 mm), mainly on the hydrocoral tissue which covers the plates of the barnacles, but it is less clear then in *Goniastrea retiformis* shown in FIG. 25b.

Thus, in the present example the distribution of chlorophyll fluorescence in three coral species carrying invertebrates symbionts using the methods of the present invention was demonstrated. These results indicate a high concentration of chlorophyll a next to the pit of the symbiotic crab Cryptochirus. There is a significant decrease in chlorophyll along the transect. In this case the change of chlorophyll concentration does not originate from a change in zooxanthellae concentration. The high chlorophyll level on the pit margins derives from bluegreen algae, which are the dominant group of algae that exists in pit walls. In the cases of *Goniastrea retiformis* and *Millepora dichotoma* there is no significant difference in chlorophyll concentration due to the symbiont animal. However, the spectral similarity maps enabled to detect changes in zooxanthellae concentration also in the cases of *Goniastrea retiformis* and *Millepora dichotoma*. The advantage of the similarity maps is that they permit one to compare between all pixels in the map at a time. All symbionts may nurture the surrounding algae with their excreta. In the case of *Favites halicora* the bluegreen algae compete with the zooxanthellae for the nutrition supply and therefor appear to be the dominant group around the symbiont. In the case of *Goniastrea retiformis* and *Millepora dichotoma* the zooxanthellae concentration is affected by the symbionts. The difference between the quantitative effects of the symbionts in *Goniastrea retiformis* and *Millepora dichotoma* may be due to the difference in the symbionts' sizes as well as the shape of their host corals. This is the first time that such an effect of symbiont animals on their host corals has been reported.

Hence, the use of the spectral imaging methods of the present invention, permitted to distinguish such changes. These methods enabled the measurement of fluorescence from a small surface area and to relate it to the concentrations of pigments in this area. The resolution was only limited by the magnification of the optic system in use. Spectral image analysis generated multipixel spectra >$10^4$ and enabled algorithmic comparisons and calculations with these spectra. In contrast to this experimental system, selected area fluorescence measurement is able to reveal only a limited array of spectral information, and does not permit spectral mapping and image reconstruction [Geze et al. (1983) J. Photochem. Photobiol. B. 20: 23–35]. Another advantage of the methods of the present invention is that most spectroscopic methods for measurement of pigments in cells are destructive, and measurements of concentration is usually done after extraction in solvents, whereas the methods employed in this example, enabled the measurement of pigments in amino. In corals, the tissue is usually removed by using a WaterPik [Johannes and Wiebe (1970) Limnol. Oceanogr. 15: 822–824] and extracts then analyzed. Removing the tissue by WaterPik prevents the examination of a small coral surface area, and the spatial limits of the samples are not clear, whereas while using the present methods the coral remained undamaged and could be returned to the water after measurements were taken.

EXAMPLE 5

IMPROVED FLUORESCENT IN SITU HYBRIDIZATION (FISH) USING SPECTRACUBE™ AND A LINEAR COMBINATION ALGORITHM

Spectral bio-imaging using the SpectraCube™ system combined with the methods of the present invention enhances the usefulness of FISH by allowing the simultaneous detection of a large number of probes, in a single measurement and with high accuracy. As a consequence, the efficiency and the reliability of detection of genetic abnormalities by FISH are greatly increased.

As detailed above, fluorescent in situ hybridization (FISH) plays an increasingly important role in many research and diagnostic areas. Since its first introduction in the 70's the FISH technique has made significant progress, enabling the detection and identification of single gene sequences, partial chromosome sequences and even whole chromosomes (i.e., chromosome painting). The many applications of FISH range from early detection of diseases, to prenatal diagnosis, aneusomy and others, to discover and thereafter treat genetic diseases and abnormalities.

Due to the high sensitivity and selectivity of FISH, which is based on hybridization of homologous nucleic acid sequences, even short sequences as small as 1 kilobase (kb) can be observed (and this will probably improve with time to enable the detection of sequences as short as 15–30 base pairs and, as a consequence, of point mutations). FISH can be applied both to interphase and cells during mitosis (or meiosis in the case of sex cells) and even to whole tissues, enabling a broad range of applications both in the fields of cytogenetics and pathology. FISH is improving hand in hand with the improvements of DNA probes, fluorescent dyes, fluorescence microscopy, high performance CCD cameras and imaging techniques.

The ability to detect many probes simultaneously has already been shown in the literature to make FISH an efficient diagnostic tool [Rudkin and Stollar (1977) Nature 265, 172–173]. However, the existing methods are cumbersome and difficult to use. As will be exemplified hereinbelow, the detection of many probes is greatly improved by the SpectraCube™ system combined with appropriate algorithms, because of its spectral resolution and sensitivity. To illustrate this capability, the reader is now referred to FIGS. 26a–c, which include an example of an interphase FISH measurement performed with chromosome 1 and chromosome 17 specific DNA probes tagged with the fluorophores Texas-Red and Rhodamine, respectively, whose fluorescence spectra are very similar. The chromosome 1 probe was a midsatellite probe for the subtelomeric region of the chromosome and was tagged with Texas-Red linked to the DNA probe via biotin post hybridization. The chromosome 17 probe was an α satellite probe for the centromeric region of the chromosome and was tagged with Rhodainine, linked to the second DNA probe via digoxigenin post hybridization. FIG. 26a shows the original image, the way it looks to the eye through the microscope; FIG. 26b shows the same sample, after being measured and processed by the SpectraCube™ system; and, FIG. 26c shows the fluorescence spectra of the Texas-Red (marked as T) and Rhodamine (marked as R) fluorophores.

As seen in FIG. 26c, the spectral peaks of Texas-Red and Rhodamine differ merely by 15 nm, and therefore it would be very difficult to distinguish between them using a filter-based system.

Looking at a color FISH image through a microscope as shown in FIG. 26a, the confidence level of recognizing the correct number of dots (marked 1–4) and of probe types appearing in the image is not particularly high. As shown in FIG. 26b, the SpectraCube™ system, on the other hand, taking advantage of the spectrum measured for each pixel, is able both to verify the existence of the dots, to count them exactly, and to discriminate between the different pairs with a high level of confidence, due to the small spectral difference between them. By artificial coloring of Texas-Red and Rhodamine fluorescence, as shown in FIG. 26c the location of probe specific fluorescence could be determined with high accuracy wherein dots 1 and 2 are of Texas-Red and dots 3 and 4 are of Rhodamine.

FIGS. 27a–b are an example of FISH measurement after hybridization of a nuclear DNA in interphase with six different probes. FIG. 27a shows the original image; FIG. 27b shows the SpectraCube™ measurement, spectral processing and artificial color display of all the detected pairs; and, FIG. 27c the spectra of the six chromophores after hybridization (marked according to the chromosomes each of which labels: 1, 8, 10, 11, 17 and X), as detected through a triple dichroic filter using the SpectraCube™ system. (For details regarding flourophores, probes and chromosomes the reader is referred to the description, Table 2 below and Cluoma Corp. Cat. No. 61502).

It is apparent from FIG. 27a, showing the original RGB image of the interphasic cell nucleus, that it is difficult to distinguish the colors from one another by eye or even by using a simple RGB color measurement. An experienced observer may, in the best case, detect three different colors of the six. FIG. 27b, however, shows the same sample shown in FIG. 27a, after processing the spectral data with proprietary classification algorithms for background subtraction and classification (see, details above), and the resulting dots have been highlighted with artificial colors as follows: brown-B1; cyan-C; blue-B2; yellow-Y; green-G; and red-R, while the background was given a black-B3, artificial color. As observed, it is possible to see all the six pairs of fluorophores and to easily differentiate among the pairs.

Figure 27:
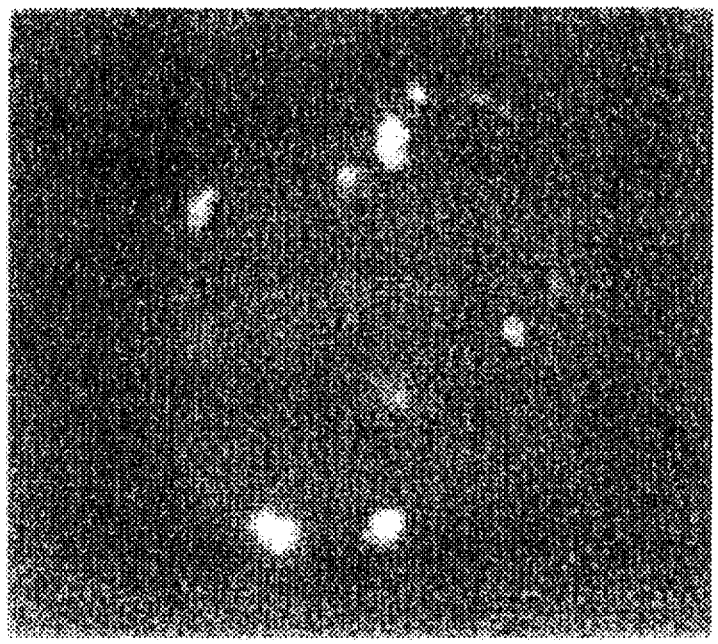
FIGS. 27a, 27b and 27c show interphase FISH performed with six different probes each labeled with a different fluorophore wherein (a) is an original image, the way it looks thorough a microscope, cells were counter stained with DAPI; (b) is the same sample, after being measured and processed by the methods of the present invention; and (c) are the fluorescence spectra of the six fluorophores.
Figure 27:
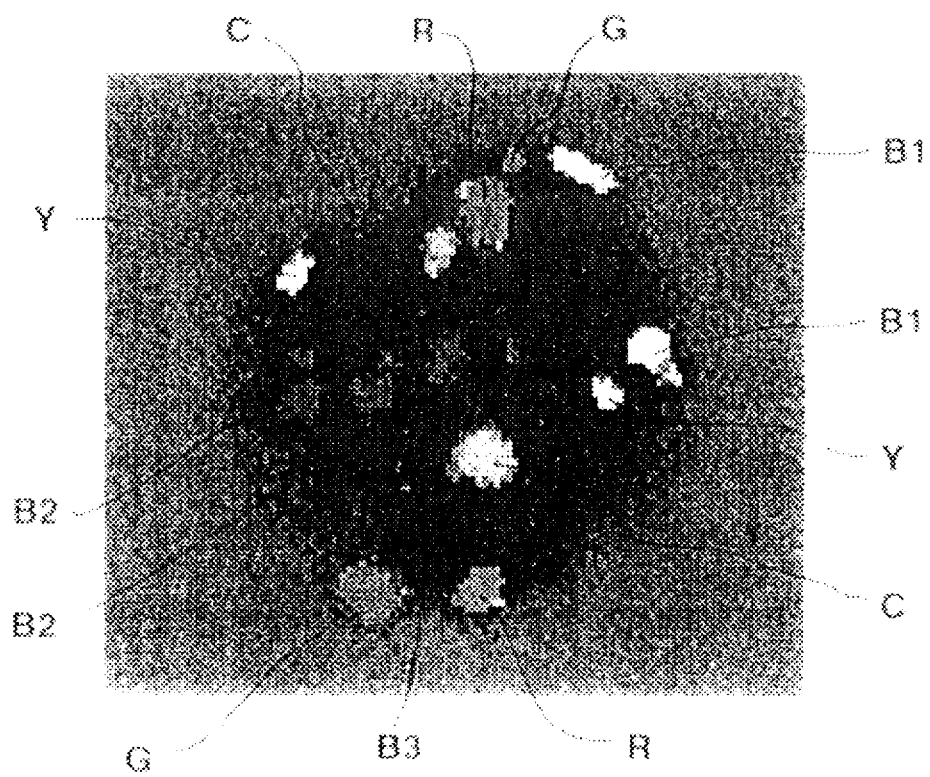

It should be further noted that one pair, the one highlighted in blue (B2), can hardly be noticed by eye, or by using a color camera; however, it is detected after applying a background subtraction algorithm on the spectral cube (compare FIG. 27 a with 27b).

The probes used are five α satellite probes for the centromeric regions of chromosomes 8, 10, 11, 17 and x, and a midsatellite probe for the subtelomeric region of chromosome 1. The fluorophores used to label each of the above chromosomes and the DAPI counter stain (backg.), their emission peak and artificial displayed color classification are summarized in Table 2.

TABLE 2

| Chromosome | Fluorophore | Emission peak | Displayed color |
|---|---|---|---|
| 8 | SPECTRUMORANGE | 588 nm | Brown (B1) |
| 10 | SPECTRUMGREEN | 538 nm | Cyan (C) |
| x | Aqua[1] | 480 nm | Blue (B2) |
| 1 | Texas-Red[2] | 615 nm | Yellow (Y) |
| 17 | FITC[3] | 525 nm | Green (G) |
| 11 | Texas-Red[2] + FITC[3] | 615, 525 nm | Red (R1) |
| backg. | DAPI[4] | | Black (B3) |

[1] obtained as labeled deoxynucleotides from Vysis, Downers Grove, IL, U. S.;
[2] conjugated via anti-digoxigenin antibody to pre hybridized digoxigenin containing probes;
[3] fluorescein-5-iso-thiocyanate, conjugated via anti-biotin antibody to pre hybridized biotin containing probes;
[4] 4',6-diamidino-2-phenylindole used for counter staining.

Figure 27C:
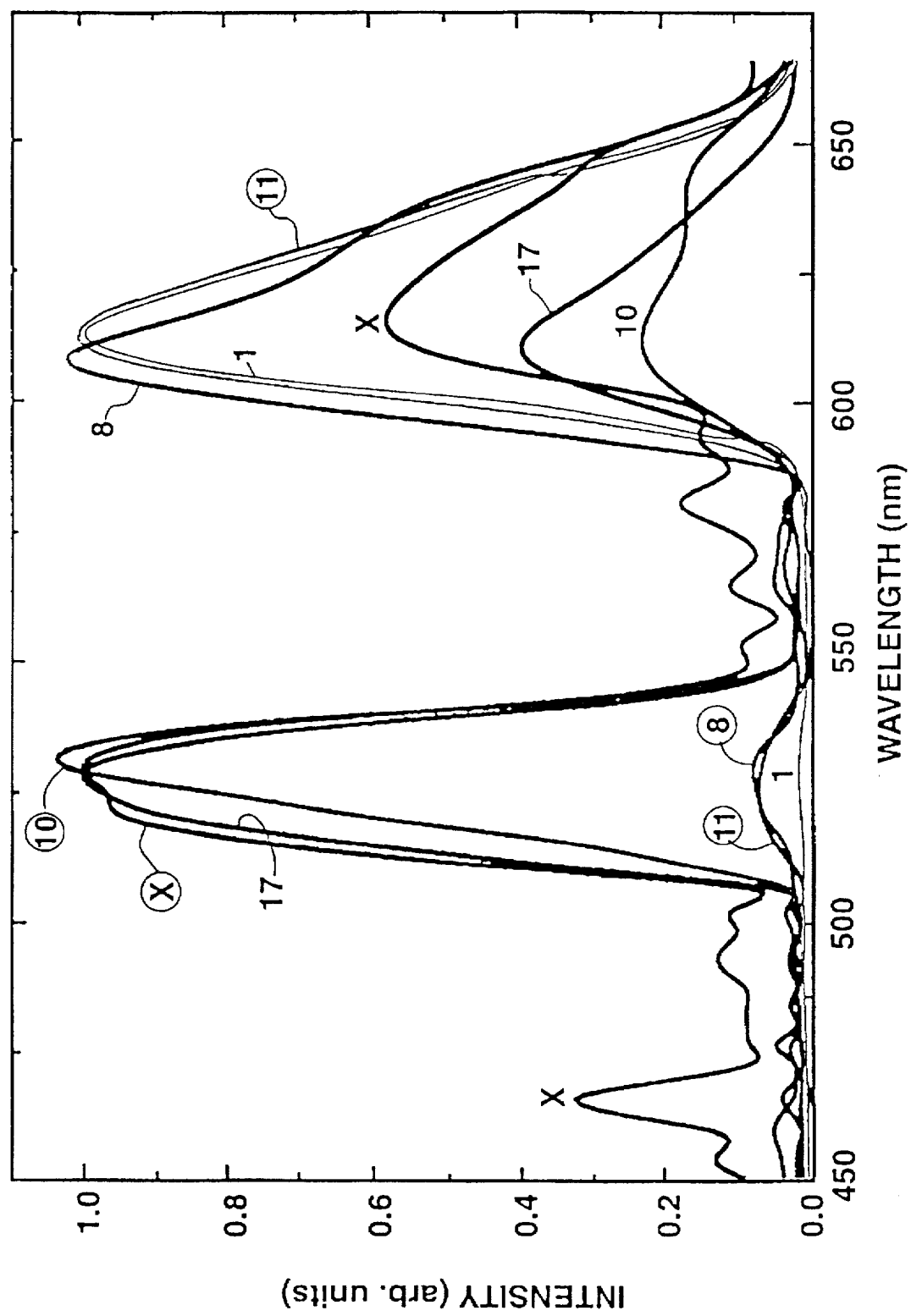

From the normalized spectral signatures of each of the six fluorophores shown in FIG. 27c, it is clear that a system based on filters measuring at a few relatively wide spectral ranges, is not able to differentiate reliably between the different probes species, because of the large overlap between the spectra. Such a system is more dependent on the absolute measurement of the intensity of each probe, and therefore it is more affected by background signals and noise. It should be further noted that spectral overlapping sometimes occurs also with auto-fluorescence originating from the cell itself. In this case too, the availability of spectral information for each pixel enables the elimination of the auto-fluorescence contribution, and yields more accurate results.

Having measured the full spectrum of each point on the image, may also help overcome specificity problems of the probes. In fact in some cases, a probe that matches a certain chromosomal DNA sequence, has also a lower specificity to a different (usually similar) sequence, and it hybridizes with a lower probability to the second sequence too. This leads to the spurious appearance of too many probes of a certain type. However, the fluorescence spectrum in the second case is very slightly shifted with respect to the first one, due to a small change in the chemical environmnent of the probe. The SpectraCube™ system, thanks to its spectral resolution and sensitivity, may eliminate this artifact. A similar artifact exists for probes which are not washed out during sample preparation, and contribute to false negative diagnosis. The SpectraCube™ system combined with the methods of the present invention, therefore, helps lowering the risk of wrong diagnosis.

Generalizing to a large number or similar dyes, the examples of FIGS. 26a–b and 27a–c show that it is possible to detect and distinguish a large number of probes, and, provided there are small spectral differences between them, the SpectraCube™ will detect and identify them in one measurement.

It is clear to one ordinarily skilled in the art that other and/or additional known and yet to be discovered or developed fluorophores and fluorophores combinations may be used in various FISH applications as detailed above to detect large number of loci simultaneously, to paint each chromosome of a karyotype in a distinguished color, etc. A list of flourophores used in state of the art cellular and molecular biology may be found in Kasten (1993) Introduction to fluorescent probes: Properties history and applications, in Fluorescent and luminescent probes for biological research, Mason Ed. Academic Press Limited, London, pp. 24–31. It is also clear to one ordinarily skilled in the art that other labeling techniques such as for example bioluminescent and chemoluminescent and also non-fluorescent labeling strategies may be similarly applied.

Thus, using the SpectraCube™ system for FISH analysis enjoys the following major advantage. The SpectraCube™ system, due to its high spectral resolution, enables simultaneous detection of numerous probes, whereas using conventional means to perform FISH (e.g., using a fluorescent microscope) limits the number of probes to be used in a single hybridization to two—four probes. Therefore, employing the SpectraCube™ system for FISH analysis saves effort and time. Furthermore, while employing the SpectraCube™ system for FISH analysis a smaller number of cells are required for full analysis, an important feature in cases where the number of cells to be analyzed is limited.

EXAMPLE 6

DIAGNOSIS OF RETINAL ABNORMALITIES USING THE SPECTRACUBE SYSTEM

Diabetic retinopathy is a potentially visually devastating condition that, in most cases, can be controlled with timely laser treatment [Ferris (1993) (commentary) JAMA 269:1290–1291]. The American Academy of Ophthalmology has suggested screening schedules to detect when patients develop clinical conditions which should be treated [Diabetic Retinopathy: American Academy of Ophthalmology Preferred Practice Patterns. San Francisco, Cal.: American Academy of Ophthalmology Quality of Care Committee Retinal Pane, American Academy of Ophthalmology, 1989].

However the suggested screening schedule is expensive, and for some individuals even the current expensive screening is not sufficient because occasional patients develop severe retinopathy between scheduled examinations. In spite of this, it has been shown that this screening is cost effective [Javitt et al. (1989) Ophthalmology 96:255–64]. This work shows that large amounts of money could be saved in health care follow up, if high and low risk patients could be more effectively identified. Therefore, any method that could increase the accuracy and reduce the cost of screening for diabetic retinopathy would be of high clinical value.

Currently, the recommended screening evaluation for diabetic retinopathy includes a detailed retinal evaluation and, in selected cases, color retinal photography [Diabetic Retinopathy: American Academy of Ophthalmology Preferred Practice Patterns. San Francisco, Cal.: American Academy of Ophthalmology Quality of Care Committee Retinal Pane, American Academy of Ophthalmology, 1989]. Fluorescein angiography of the retina is routinely performed today, but it is invasive, unpleasant, and causes occasional deaths. Furthermore, the additional information obtained by fluorescein angiography does not help categorize patients into those who may benefit from immediate laser treatment and those who will not [Ferris (1993) (commentary) JAMA 269:1290–1].

According to the present invention the SpectraCube™ technology, combined with specially developed algorithms, using spectroscopic data and imaging information at the same time, will be used to classify different stages of retinal ischemia, and therefore will be a clinical tool to allow a clinician to categorize most diabetic patients as either ischemic or non-ischemic.

The oxygen supply of the retina is provided by both the choroidal and retinal circulation. The choroid serves as the oxygen source for the photoreceptors in the avascular outer retina, whereas the retinal circulation plays a crucial role in maintaining the oxygen supply to the neural elements and nerve fibers in the inner retina. Because of the high oxygen needs of the retina, any alteration in circulation such as seen in diabetic retinopathy, hypertension, sickle cell disease, and vascular occlusive diseases results in functional impairment and extensive retinal tissue damage.

Noninvasive measurements of the oxygen saturation of blood in retinal vessels was first proposed by Hickham et al. [Hickham et al. (1963) Circulation 27, 375] using a two-wavelength photographic technique (560 and 640 nm) for retinal vessels crossing an optic disk. A more advanced approach based on the three wavelength method of Pittman and Duling is presented in Delori (1988) Applied Optics 27, 1113–1125.

The SpectraCube™ system, based on the spectral information that it provides, not only enables the noninvasive evaluation of the saturation level of hemoglobin in retinal blood vessels, but also, because of the imaging information that it provides, it can be used for the detection and mapping of retinal ischemia. Joined to principal component or neural network algorithms, it can also be used for classification of the different retinopathy stages, and treatment categorization of diabetic patients.

Many chemicals in the living tissue are related to the functioning of the vessels and metabolism. Therefore, even though the primary element for retinal ischemia is oxygen, which can be measured through the concentration of hemoglobin in the oxy- and deoxy forms, important information can be obtained also by measuring the concentration of other constituents, such as $NAD^+$, NADH, flavin, cytochromes, etc. There is a trade-off between the amount of time and computing resources that are necessary and can be afforded in a particular measurement, and the amount of information, sensitivity, reliability and specificity that can be achieved.

Considering the large amount of prior art that has been described for spectral detection of such chemical constituents of tissue, correlating the absorption peaks in reflectance, and the fluorescence peaks in UV or blue light, single or multiple wavelengths excitation, to their concentrations, it is conceived that the SpectraCube™ system combined with the methods of the present invention can be used to map concentrations of one or more of such constituents simultaneously. The particular hardware configuration in which the SpectraCube™ will be operated, will dictate the type and amount of information obtained.

For example, the simplest and most straightforward configuration is when the SpectraCube™ is attached to the CCD port of a fundus camera, so that the retina is imaged, and the same wide band white light source of the fundus camera is used to measure the reflected light from the retina. In this case oxygen concentrations can be measured using Delori's algorithm [Delori (1995) Appl. Optics Vol. 27, 1113, 1988, and Appl Optics, Vol. 28, 1061; and, Delori et al. (1980) Vision Research, Vol. 20, 1099], or similar, extended to all pixels of the imaged retina. More complicated systems based on SpectraCube™ are: (1) auto-fluorescence spectral imaging; (2) spectral imaging using UV or blue light fluorescence excitation lamp; (3) spectral imaging using laser excited fluorescence, singly, simultaneously, or in succession, at the following wavelengths: 650, 442, 378, 337, 325, 400, 448, 308, 378, 370, 355, or any other equivalent wavelengths which give similar information.

These configurations can be built in several ways, either separately or combined in any number of combinations in the same instrument: the instrument is made of the light source(s), the fundus camera and the SpectraCube™, including a computer and software to interpret the data and display it in a useful way for the ophthalmologist.

In all cases of white light reflection, auto-fluorescence, single wavelength continuous wave laser excitation fluorescence, or multiple wavelength laser excitation fluorescence, the sample is illuminated and a spectral image is measured.

In the case of pulsed laser(s) illumination, the method of work of the SpectraCube™ system is slightly modified and requires some hardware changes which are not basic and substantial, but important for the instrument to operate. These changes are the following:

For single pulsed laser excited fluorescence spectral imaging, the laser pulses and the frame grabbing of the CCD of the SpectraCube™ are synchronized with the scanning angle of the interferometer, so that at each pulse the interferometer performs a step, and a new frame is collected by the computer (several pulses can also be used in general for each frame, as long as this number does not change from frame to frame). In this way, at each OPD value the interferogram value corresponds to the same number (but different) of pulses of the laser. This is necessary to ensure that each frame is taken with the same total illumination intensity, otherwise, each frame measures the fluorescence resulting from a different number of laser pulses and the interferogram will be distorted.

For several pulsed lasers induced fluorescence spectral imaging, the method of work can be in two ways: (1) collect a whole spectral cube for each laser separately as above, in succession; this means that during a measurement only one laser is activated, and at the end there is one spectral cube measured for each laser wavelength; and, (b) pulse each laser in succession in synchronization with the interferometer and the frame grabbing, so that all the lasers are switched in succession before the next step of the interferometer and the next frame is taken; at the end, only one spectral cube is measured.

At the end of course all the information must be analyzed and interpreted. The most important algorithms are going to be the ones that compare the resulting intensities between different wavelengths and between different pixels on the image. These algorithms should consider variations of intensities, and ratios between different regions in the tissue and between different wavelengths. The method will be very sensitive, and may replace slit lamp imaging (white light or filtered light), because it will provide a large quantitative information.

Other applications will be apparent to one skilled in the art. These include visual loss due to choroidal ischemia, acute sectorial choroidal ischemia, ischemic optic neuropathy, corneal and iris problems, etc., and many others which are analyzed today by imaging techniques, either using white light or fluorescence of different origins.

EXAMPLE 7

MAPPING CANCEROUS TISSUE IN VIVO IN COLON, BLADDER, LUNGS, CERVIX AND OTHER INTERNAL ORGANS.

Since the SpectraCube™ system can be attached to any imaging optics including endoscopes and laparoscopes, it can be used as an aid to the surgeon before, during or after surgery to accurately define the diseased tissue to be removed, to aid in the decision where to start cutting, where to stop, and to judge whether all diseased tissue has been removed in an operation. The SpectraCube™ system is intrinsically suitable to analyze the nature of the tissue through the chemical composition, related in turn to its spectral characteristics, and to provide a visual map (usually enhanced), for a user to grasp, take decisions and act.

In the case of cancerous tissues detection in vivo, both the hardware configurations and the types of analysis and display algorithms involved are very similar to the above described ophthalmologic examples (see Example 6). The differences are in the collecting optics (endoscopes of different types instead of fundus camera), in the types of some basic molecular components involved in the detection: some of these are probably common, such as oxygen concentration, additional others are collagen and elastin, genetic material in the cell nuclei, such as DNA chromatin, etc. The illumination and synchronization requirements in the case of multiple wavelengths or pulsed excitation are similar as well [Pitris et al., Paper presented at European Biomedical Optics Week by SPIE, 12–16 Sep. 1995, Barcelona Spain]

EXAMPLE 8

AID TO DIAGNOSTIC PATHOLOGY BY CELL AND TISSUE CLASSIFICATION USING PRINCIPAL COMPONENT ANALYSIS

Today many diagnoses and surgical decisions are taken on the basis of microscopic examinations of cells and tissues. The examinations are done on cell smears, such as blood, vaginal and cervical smears and urine samples or on stained and/or fixated tissue sections. A typical example is the widespread Pap smear done today on very large numbers of cervical smears to test for Papilloma virus cervical cancer.

The analysis is done by a pathologist who has learned over many years of practice to recognize and classify cells he sees through the microscope, by their shapes, color, relative sizes of nucleus and cytoplasm, cells clustering and various other spatial features. The pathologist has also learned to disregard debris material and artifacts appearing in the smear.

These tests however suffer from a fairly large degree of subjectivity, and because of the large numbers of tests to be made daily, a prescreening is often performed by technicians to indicate to the pathologist only the suspicious cells or tissues to be analyzed in-depth. These prescreening tests suffer in turn from a certain degree of lack of reliability, because of human errors and fatigue.

It is a widely recognized need within the pathology community to increase the objectivity and reliability of these tests significantly, and to automate the prescreening stage. Nowadays pathologists are required to make the final diagnosis, but it is not inconceivable that in the future the screening as well as the diagnosis will be performed automatically.

SpectraCube™ technology, including clever interpretation and display algorithms, can be used in all these stages of pathologic diagnosis: in the screening, as an aid to increase objectivity and reliability of the diagnosis by the pathologist, and eventually in the completely automatic diagnosis.

It is well known that cells of diseased tissue undergo extensive chemical changes, depending on the specific disease and its specific stage. As a consequence, these changes show up in the spectroscopic data, in transmission of stained cells or tissue, in auto-fluorescence, in tagging probes fluorescence, or in reflection contrast microscopy. The SpectraCube™ system, combining spectroscopy and imaging, being able to work in all of these modes, is a very good instrument to detect and quantitatively measure these features, and to present them to the pathologist or to the surgeon for decision making, after appropriate mathematical treatments.

The algorithms employed for display and interpretation can be any of the above mentioned ones, e.g., similarity mapping and classification of different types, principal component analysis, neural network, and others all evident to one ordinarily skilled in the art.

Figure 28:
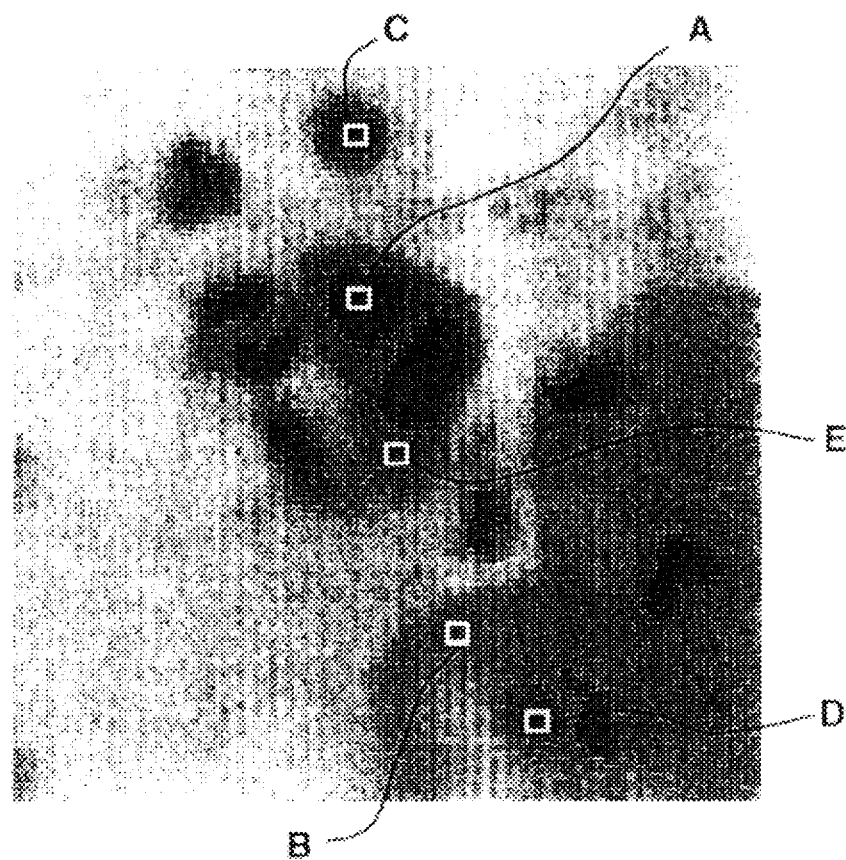
FIG. 28 shows an RGB-image of Haematoxylin-Eosin stained cells as routinely prepared for a Papanicolaou test (i.e., Pap smear); the cell marked A is a HPV (human Papilloma virus) cancerous cervical cell, whereas the cell marked B is a normal cervical cell; C, D and E denote a polymorphonuclear (i.e., neutrofil) cell, the nucleus of squamous cell and the cytoplasm of the cell marked A.
Figure 29:
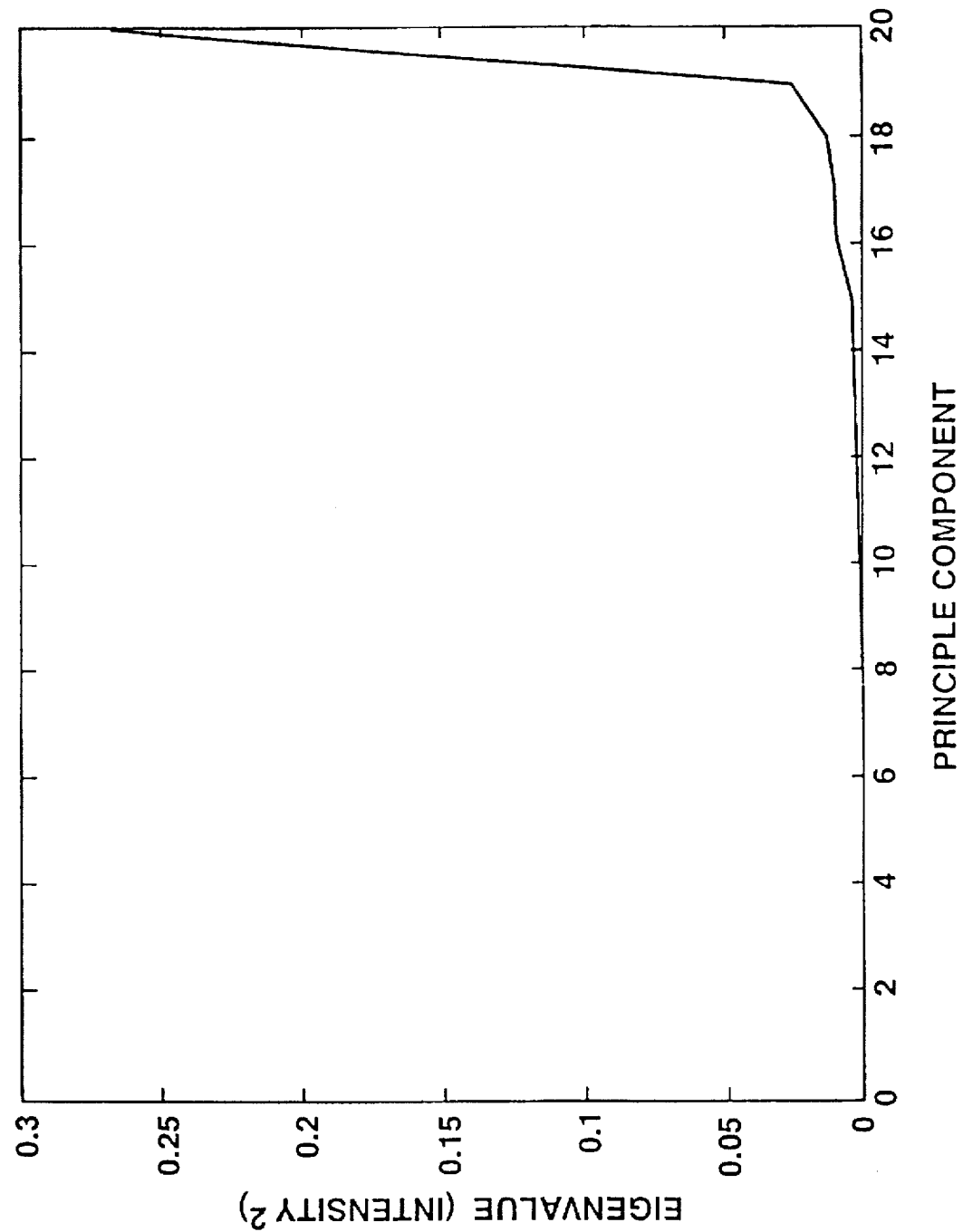
FIG. 29 shows a principal component analysis in which the eigenvalues $\mu_i$ are plotted as a function of twenty different principal components i.e., wavelength ranges (i=1, ... .20)

FIGS. 28 through 30 demonstrate the way the present invention is used in the field of diagnostic pathology. FIG. 28 is a transmission microscopy RGB-image acquired using the methods of the present invention, of cervical smear Haematoxylin-Eosin stained cells as routinely prepared for a Papanicolaou test (i.e., Pap smear). The cell in the center of the image (marked A, pointed to the nucleus of the cell) is a HPV (human Papilloma virus) cell (i.e., cancerous cervical cell), whereas the cell (marked B, pointed to the cytoplasm of the cell) on the lower right portion of the image is a normal cervical cell. C, D and E denote a polymorphonuclear (i.e., neutrofil) cell, the nucleus of squamous cell marked B, and the cytoplasm of the cancerous cell marked A, respectively. Since the cells are presented in black and white (originally in color) and are therefore less clear, their borders are demarcated by a manually applied artificial line.

Figure 30A:
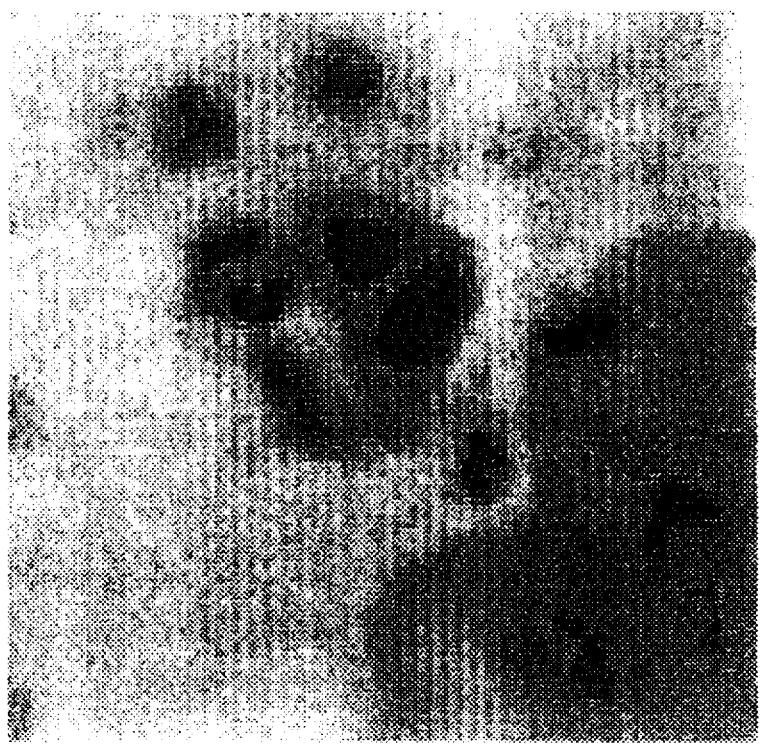

The acquired spectral cube was subjected to a principal component analysis as described above. For this purpose, the whole spectral range (450 nm–800 nm) was divided into twenty narrow wavelength ranges, i.e., N=20, each of which is referred to now as a black and white image based on the intensity of light for each of the pixels at each of the one through twenty wavelength ranges, or in other words to a specific principal component of which twenty exist. These twenty images were used to form the columns of matrix B' as defined above. Matrices B and C and then the eigenvectors $V_i$ and eigenvalues $\mu_i$ of matrix C were calculated in accordance with the above description. In FIG. 29, the eigenvalues $\mu_i$ are plotted as a function of the twenty different principal components i.e., the wavelength ranges (i=1, ..., 20). FIG. 30a presents a black and white intensity image obtained by using the values of the vector product $BV_{20}$ as pixel intensities, and is very similar to the original image as seen through a black and white camera and to FIG. 28 when presented in black and white. As seen however it does not carry important spectral information intrinsic to the sample, but mainly the microscope lamp spectrum as affected by the transmission of light through the sample. On the other hand, as shown in FIGS. 30b–c, black and white intensity images obtained similarly yet with other eigenvectors, for example $BV_{10}$ and $BV_{13}$, show a new effect: pixels located around the edge of the cancerous cell (A in FIG. 28) and only the cancerous cell show areas of higher intensity (white zones in FIGS. 30b and 30c, circled) than all the rest of the image, whereas, the normal cell (B in FIG. 28) appears with an intensity which is lower than the rest of the image (dark black zones in FIGS. 30b and 30c). Therefore, it is concluded that what ever substance or structure responsible for principal components 10 and 13, which as can be seen in FIG. 29 have very low abundance in the examined field of view, are unique to the cancerous cell and are under represented in some regions of the normal cell. Hence, the fact that only a certain type of cell or part of a cell shows up in one or more of the images constructed with matrix B and the eigenvectors $V_i$, can be used to classify the different types of cells when measured by the methods of the present invention.

To summarize, in a previous U.S. patent application Ser. No. 08/392,019, a unique spectral imaging system was described, based on a specially sensitive interferometric method combined with a two-dimensional CCD sensor and electronics, to measure and memorize in the computer tens and hundreds of thousands of spectra simultaneously in a spatially organized way. The present invention describes how that hardware can be used for biology research, medical therapy and diagnostics. The combination of spectroscopy and imaging in the proposed methodology gives rise to a new field, termed herein spectral bio-imaging.

The great power of the present invention is that, since it allows the spectroscopic measurements and data to be collected for every point (i.e., pixel) of a sample independently and simultaneously, it provides both information on materials and molecule types and concentrations as function of position in the sample (which allows mapping of material presence and concentration), and also all the conventional imaging (which allows conventional morphological analysis (see, for example U.S. Pat. No. 4,965,725 to Rutenberg) at the same time. Hence, the present invention can be used for both the detection of spatial organization and quantification of cellular and tissue components, structures, organelles, genetic material, administered fluorescent tagging probes, and the distribution within cells and tissues of administered drugs, using light transmission, reflection, scattering and fluorescence strategies with high spatial and spectral resolution.

An additional advantage of the present invention is in the increased simplicity of interpretation of the spectroscopic data. The very fact that the data according to the present invention are collected not point by point, but in an imaging organized way, and not at few wavelengths but in a large number of wavelengths, it allows (1) comparisons to be made between, for example, cancerous and non cancerous tissue surfaces of the same patient thereby automatically eliminating pigmentation effects which differ from person to person; (2) comparisons to be made between intensities at different wavelengths, thereby automatically eliminating spectral effects which are independent of the sought feature; and, (3) a user to easily visualize and find the sought features and their borders in the image, once the system software has performed proper feature enhancement (e.g. using artificial colors or other means) and has presented the resulting enhanced image on an appropriate display (e.g. a computer screen or a dedicated video screen).

An additional advantage of the present invention is the well known Fellgett or multiplex advantage of Fourier transform spectroscopy over filters, gratings and other types of dispersion techniques, which expresses itself in an increased signal-to-noise ratio in spectral measurements, when the noise level is independent of signal (background or system limited performance), and when the noise is proportional to the square root of the signal (photon noise limitation) and the signal is higher than the signal averaged over the whole spectral range.

An additional advantage of the present invention is that the special optical configuration described in details in the previous U.S. patent application Ser. No. 08/392,019, allow this system concept and the system hardware itself to be used on any sample surface that can be imaged, and to be attached to any imaging optics which produces an image, either existing or to be developed in the future.

An integral part of the present invention are also a number of mathematical algorithms that the computer software employs to interpret and display the data in a meaningful way. It is apparent that many types of algorithms can be used in the same instrument (mostly for research users, enabling a very versatile work), or in separate instruments (for practitioners, enabling dedicated, fast work), or any combinations and levels of versatility that may be required for different applications. The algorithms can be strictly based on interpretation of spectral information (known in the state of the art or future), such as spectral absorption or emission peaks of specific single chemical elements or molecules, mostly used for concentration mapping of such chemicals, or strictly morphological, using image shapes and existing or future image processing algorithms, or combinations of spectral and imaging information, such as comparisons between the different spectra of all pixels, by principal component analysis, arithmetical operations, background subtraction or ratioing of different types, between different pixels or spatial regions, and between different wavelengths or spectral regions.

It will be apparent to any skilled in the art that many other types of applications can be envisaged which are similar or related to the ones described above, either by using the above mentioned imaging devices or other existing ones attached to the imaging spectrometer system, or by using any other such imaging devices which will exist in the future.

While the invention has been described with respect to a limited number of embodiments, it will be appreciated that many variations, modifications and other applications of the invention may be made.

What is claimed is:

1. A spectral bio-imaging method characterized by high spatial and high spectral resolutions, the method comprising the steps of:

(a) preparing a sample to be spectrally imaged;
(b) viewing said sample through an optical device, said optical device being optically connected to an imaging spectrometer, said optical device and said imaging spectrometer being for obtaining a spectrum of each pixel of said sample by:

(i) collecting incident light simultaneously from all pixels of said sample using collimating optics;
(ii) passing said incident collimated light through an interferometer system having a number of elements, so that said light is first split into two coherent beams which travel in different directions inside said interferometer and then said two coherent beams recombine to interfere with each other to form an exiting light beam;
(iii) passing said exiting light beam through a focusing optical system which focuses said exiting light beam on a detector having a two-dimensional an-ay of detector elements, so that at each instant each of said detector elements is the image of one and always the same pixel of said sample for the entire duration of the measurement, so that the real image of the sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
(iv) rotating one or more of said elements of said interferometer system, so that said optical path difference between said two coherent beams generated by said interferometer system is scanned simultaneously for all said pixels of said sample; and
(v) recording signals of each of said detector elements as function of time using a recording device to form a first spectral cube of data; and (c) interpreting said first spectral cube of data using a mathematical algorithm.

2. A method as in claim 1, further comprising the step of:
(d) displaying a map of said interpreted spectral cube of data.

3. A method as in claim 1, wherein said optical device is selected from the group consisting of a microscope, a camera lens, an endoscope, a fundus camera and a funduscope.

4. A method as in claim 3, wherein said microscope is selected from the group consisting of a reflection microscope, a transmission microscope, a fluorescence microscope, an upright microscope, an inverted microscope, a dark field microscope, a confocal microscope, a standing wave confocal microscope and a reflection contrast microscope.

5. A method as in claim 1, wherein said collimated light is selected from the group consisting of light transmitted through said sample, light reflected from said sample, light scattered from said sample and light emitted from said sample.

6. A method as in claim 5, wherein said light emitted from said sample is selected from the group consisting of administered probe fluorescence, administered probe induced fluorescence and auto-fluorescence.

7. A method as in claim 1, wherein said light originates from a source selected from the group consisting of laser, white light, filtered light, ultraviolet light and a light having a small wavelength range.

8. A method as in claim 1, wherein said light originates from a multiplicity of light sources, said sources operate simultaneously.

9. A method as in claim 1, wherein said light originates from a multiplicity of light sources, said sources operate successively.

10. A method as in claim 1, wherein said two-dimensional array is selected from the group consisting of a video rate CCD, a cooled high dynamic range CCD, an intensified CCD and a time gated intensified CCD.

11. A method as in claim 1, wherein said sample is selected from the group consisting of a cell, a tissue and an organism.

12. A method as in claim 11, wherein said cell and said tissue are from a human.

13. A method as in claim 11, wherein said cell is selected from the group consisting of a cell collected by a Pap smear, a blood cell, a fetal cell, a cell suspected of being malignant, a cell during interphase, a cell during mitosis and a cell during meiosis.

14. A method as in claim 11, wherein said tissue is selected from the group consisting of eye retina, a retinal blood vessel, a tumor, skin, cornea, hair, lungs, stomach, intestines, bladder, colon, prostate, cervix, arteries, veins and heart.

15. A method as in claim 1, wherein said sample is the eye retina, the method is for detecting oxygenated and deoxygenated hemoglobin in the retinal blood vessels.

16. A method as in claim 1, wherein said sample is the eye retina, the method is for detecting melanin pigmentation level in the retina.

17. A method as in claim 1, wherein said sample is selected from the group consisting of a cell, a tissue section and an organism; said light is induced by a probe, said probe binds to a specific cellular constituent, the method is for detecting the presence or the level of said cellular constituent.

18. A method as in claim 17, wherein said probe includes a conjugated fluorescent moiety and said induction is a fluorescence light emission of said fluorescent moiety.

19. A method as in claim 18, wherein said probe further includes a nucleic acid molecule, the method is for detecting the presence or the level of a cellular nucleic acid hybridizing with said nucleic acid molecule.

20. A method as in claim 19, wherein said cellular nucleic acid is selected from the group consisting of deoxyribonucleic acid and ribonucleic acid.

21. A method as in claim 17, wherein said probe includes an antibody, the method is for detecting the presence or the level of a cellular protein recognized by said antibody.

22. A method as in claim 18, wherein said fluorescent moiety is selected from the group consisting of Aqua, Texas-Red, FITC, rhodamine, rhodamie derivative, fluorescein, fluorescein derivative, cascade blue and any combination thereof.

23. A method as in claim 1, wherein said mathematical algorithm is a point operation analysis of said spectrum of each of said pixels in said sample.

24. A method as in claim 23, wherein said point operation analysis includes mapping said spectrum of each of said pixels in said sample into a scalar according to a transformation function.

25. A method as in claim 23, wherein said point operation analysis includes mapping said spectrum of each of said pixels of said sample into another spectrum according to a transformation function.

26. A method as in claim 1, wherein said mathematical algorithm is a morphological analysis.

27. A method as in claim 1, wherein said mathematical algorithm is a similarity mapping analysis for computing for each of said pixels in said sample a spectral difference from a reference spectrum.

28. A method as in claim 27, wherein said similarity mapping analysis results in generating a gray level or a pseudocolor image, in which bright pixels correspond to a small spectral difference and dark pixels correspond to a large spectral difference.

29. A method as in claim 27, wherein said similarity mapping analysis results in generating a gray level or a pseudocolor image, in which bright pixels correspond to a large spectral difference and dark pixels correspond to a small spectral difference.

30. A method as in claim 27, wherein said spectral difference is a scalar defined as the integral over a predefined wavelength range of the absolute value of the difference between said spectrum of each of said pixels and said reference spectrum.

31. A method as in claim 1 wherein said mathematical algorithm is a classification mapping analysis computing for said spectrum of each of said pixels a spectral difference from several reference spectra.

32. A method as in claim 31, wherein said classification mapping analysis results in generating a pseudocolors image, in which groups of pixels having a predetermined maximal spectral differences from one of said several reference spectra are colored with a predetermined pseudocolor.

33. A method as in claim 31, wherein said spectral difference is a scalar defined as the integral over a predefined wavelength range of the absolute value of the difference between said spectrum of each of said pixels and one of said several reference spectra.

34. A method as in claim 1, wherein said mathematical algorithm is a principal component analysis.

35. A method as in claim 34, wherein said principal component analysis includes:

(a) building a covariant matrix for all of said pixels and said wavelengths of said measurement, including wavelengths of exciting sources when multiple wavelengths are used;

(b) diagonalizing said covariant matrix and finding all independent orthogonal spectral base elements;

(c) finding which of said base elements tag certain features in said sample.

36. A method as in claim 1, wherein said mathematical algorithm is a linear combination analysis.

37. A method as in claim 36, wherein said linear combination analysis includes applying an arithmetical function between corresponding wavelengths of corresponding pairs of pixels belonging to said first spectral cube of data and to a second spectral cube of data, to obtain a resulting third spectral cube of data.

38. A method as in claim 36, wherein said linear combination analysis is for a purpose selected from the group consisting of averaging two spectral cubes of data, time changes follow-up and spectral normalization.

39. A method as in claim 36, wherein said linear combination analysis includes applying a given scalar to every wavelength of said spectra of each of said pixels by an arithmetical function, said function is selected from the group consisting of addition, subtraction, multiplication, division and combinations thereof.

40. A method as in claim 36, wherein said linear combination analysis is for background subtraction in which a spectrum of a pixel located in a background region of said sample is subtracted from said spectra of said pixels of said sample.

41. A method as in claim 36, wherein said linear combination analysis is for a calibration procedure in which a spectrum measured prior to said viewing said sample is for dividing said spectra of said pixels of said sample.

42. A method as in claim 1, wherein said mathematical algorithm is an optical density analysis.

43. A method as in claim 42, wherein said optical density analysis is for obtaining an interpreted image which is an optical density map.

44. A method as in claim 1, wherein said mathematical algorithm computes a Red-Green-Blue color image using predefined wavelength ranges.

45. A method as in claim 1, wherein said mathematical algorithm computes a ratio between intensities at two different wavelengths for each of said spectra of said pixels.

46. A method as in claim 1, wherein said mathematical algorithm computes a ratio between intensities at two different wavelengths for each of said spectra of said pixels and paints each of said pixels in a lighter or darker artificial color, according to said computed ratio.

47. A method as in claim 1, wherein the method is for spectral identification of multiple fluorophores administered to said sample.

48. A method as in claim 1, wherein the method is for detecting micro-environmental changes in said sample.

49. A method as in claim 48, wherein said micro-environmental changes are selected from the group consisting of local electrical potential, pH level and intracellular ions concentration.

50. A method as in claim 49, wherein said ions are selected from the group consisting of hydrogen ions, sodium ions, magnesium ions, zinc ions and calcium ions.

51. A method as in claim 1, wherein the method is for measuring auto-fluorescence from a natural constituent in said sample.

52. A method as in claim 1, wherein said natural constituent is selected from the group consisting of chlorophyll, porphyrins and cytoplasmic proteins.

53. A method as in claim 51, wherein said sample is selected from the group consisting of eye retina, a retinal blood vessel, a tumor, skin, cornea, hair, lungs, stomach, intestines, bladder, colon, prostate, cervix, arteries, veins, heart and cells obtained by smears.

54. A method as in claim 1, wherein the method is for an application selected from the group of applications consisting of biology research, drug development industry, cell and tissue classification in pathology, hematology, urine analysis, gene identification and mapping in chromosomes, genetic disease diagnosis, cell organelles anatomy and physiology, chromatin distribution and condensation in a cell nuclei, cytoplasm organelles and constituents mapping, cell membrane mapping, nuclear membrane mapping mapping of skin cancers, differentiating between melanoma and nevi, port wine stains mapping and, skin imaging before, during, and after a photodynamic therapy treatment.

55. A method as in claim 54, wherein said cytoplasm constituents are selected from the group consisting of $NAD^+$, NADH, flavin and cytochromes.

56. A method as in claim 1, wherein the method is for measuring fluorescence resonance energy transfer to determine spatial separation between at least two fluorophores in said sample.

57. A method as in claim 56, wherein at least one of said fluorophores is externally administered to said sample.

58. A method as in claim 1, wherein said sample is selected from the group consisting of a cell, a tissue and an organism, the method is for identifying and mapping cellular and subcellular details in said sample.

59. A method as in claim 58, wherein said sample is stained using a method selected from the group consisting of Romanowsky-Giemsa staining, Haematoxylin-Eosin staining and May-Grunwald-Giemsa staining.

60. A method as in claim 59, wherein said subcellular details are types of chromatin organization in the nucleus, said types are selected from the group consisting of heterochromatin and euchromatin.

61. A method as in claim 1, wherein said sample is selected from the group consisting of a cell, tissues and organisms, the method is for monitoring life processes in said sample as function of time.

62. A fluorescent in situ hybridization method comprising the steps of:
   (a) labeling with at least one fluorescent dye at least one nucleic acid molecule to obtain at least one fluorescently tagged nucleic acid probe;
   (b) hybridizing said probe in situ with cellular nucleic acids of a biological sample;
   (c) viewing said biological sample through a fluorescence microscope, said fluorescence microscope being optically connected to an imaging spectrometer, said fluorescence microscope and said imaging spectrometer being for obtaining a spectrum of each pixel of said biological sample by:
      (i) collecting incident light simultaneously from all pixels of said biological sample using collimating optics;
      (ii) passing said incident collimated light through an interferometer system having a number of elements, so that said light is first split into two coherent beams which travel in different directions inside said interferometer and then said two coherent beams recombine to interfere with each other to form an exiting light beam;
      (iii) passing said exiting light beam through a focusing optical system which focuses said exiting light beam on a detector having a two-dimensional allay of detector elements, so that at each instant each of said detector elements is the image of one and always the same pixel of said biological sample for the entire duration of the measurement, so that the real image of the biological sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
      (iv) rotating one or more of said elements of said interferometer system, so that said optical path difference between said two coherent beams generated by said interferometer system is scanned simultaneously for all said pixels of said biological sample; and
      (v) recording signals of each of said detector elements as function of time using a recording device to form a first spectral cube of data; and
   (d) interpreting said first spectral cube of data using a mathematical algorithm.

63. A fluorescent in situ hybridization method comprising the steps of:
   (a) hybridizing at least one nucleic acid probe in situ with cellular nucleic acids of a biological sample;
   (b) labeling each of said at least one probe with at least one fluorescent dye;
   (c) viewing said biological sample tough a fluorescence microscope, said fluorescence microscope being optically connected to an imaging spectrometer, said fluorescence microscope and said imaging spectrometer being for obtaining a spectrum of each pixel of said biological sample by:

(i) collecting incident light simultaneously from all pixels of said biological sample using collimating optics;

(ii) passing said incident collimated light through an interferometer system having a number of elements, so that said light is first split into two coherent beams which travel in different directions inside said interferometer and then said two coherent beams recombine to interfere with each other to form an exiting light beam;

(iii) passing said exiting light beam through a focusing optical system which focuses said exiting light beam on a detector having a two-dimensional array of detector elements, so that at each instant each of said detector elements is the image of one and always the same pixel of said biological sample for the entire duration of the measurement, so that the real image of the biological sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;

(iv) rotating one or more of said elements of said interferometer system, so that said optical path difference between said two coherent beams generated by said interferometer system is scanned simultaneously for all said pixels of said biological sample; and (v) recording signals of each of said detector elements as function of time using a recording device to form a first spectral cube of data; and (d) interpreting said first spectral cube of data using a mathematical algorithm.

64. A method as in claim 62, wherein said mathematical algorithm is a classification mapping analysis, said analysis computing for said spectrum of each of said pixels a spectral difference from at least one reference spectrum.

65. A method as in claim 62, wherein said mathematical algorithm is a linear combination analysis, said analysis is for a background subtraction.

66. A method as in claim 65, further comprising the step of using an additional mathematical algorithm being a classification mapping analysis, said additional mathematical algorithm computing for said spectrum of each of said pixels a spectral difference from at least one reference spectrum.

67. A method as in claim 64, wherein said classification mapping analysis includes computing for said spectrum of each of said pixels a spectral difference from at least one reference spectrum.

68. A method as in claim 66, wherein said classification mapping analysis includes computing for said spectrum of each of said pixels a spectral difference from at least one reference spectrum.

69. A cell classification method comprising the steps of:

(a) preparing a smear of cells for analysis;

(b) viewing said smear of cells through a transmission microscope, said transmission microscope being optically connected to an imaging spectrometer, transmission microscope and said imaging spectrometer being for obtaining a spectrum of each pixel of said smear of cells by:

(i) collecting incident light simultaneously from all pixels of said smear of cells using collimating optics;

(ii) passing said incident collimated light through an interferometer system having a number of elements, so that said light is first split into two coherent beams which travel in different directions inside said interferometer and then said two coherent beams recombine to interfere with each other to form an exiting light beam;

(iii) passing said exiting light beam through a focusing optical system which focuses said exiting light beam on a detector having a two-dimensional array of detector elements, so that at each instant each of said detector elements is the image of one and always the same pixel of said smear of cells for the entire duration of the measurement, so that the real image of the smear of cells is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;

(iv) rotating one or more of said elements of said interferometer system, so that said optical path difference between said two coherent beams generated by said interferometer system is scanned simultaneously for all said pixels of said smear of cells; and (v) recording signals of each of said detector elements as function of time using a recording device to form a first spectral cube of data; and (c) interpreting said first spectral cube of data using a principal component algorithm.

* * * * *